United States Patent
Gibbings et al.

(10) Patent No.: US 10,851,372 B2
(45) Date of Patent: Dec. 1, 2020

(54) EXOSOME PACKAGING OF NUCLEIC ACIDS

(71) Applicant: University of Ottawa, Ottawa (CA)

(72) Inventors: Derrick Gibbings, Ottawa (CA); James Andrew Taylor, Gatineau (CA)

(73) Assignee: University of Ottawa, Ottawa (CA)

( * ) Notice: Subject to any disclaimer, the term of this patent is extended or adjusted under 35 U.S.C. 154(b) by 0 days.

(21) Appl. No.: 15/760,874

(22) PCT Filed: Sep. 30, 2016

(86) PCT No.: PCT/CA2016/051140
§ 371 (c)(1),
(2) Date: Mar. 16, 2018

(87) PCT Pub. No.: WO2017/054085
PCT Pub. Date: Apr. 6, 2017

(65) Prior Publication Data
US 2019/0093105 A1    Mar. 28, 2019

Related U.S. Application Data

(60) Provisional application No. 62/236,057, filed on Oct. 1, 2015.

(51) Int. Cl.
| | |
|---|---|
| *C12N 15/113* | (2010.01) |
| *C12Q 1/6881* | (2018.01) |
| *C12N 15/87* | (2006.01) |
| *C12N 15/10* | (2006.01) |
| *C12N 15/11* | (2006.01) |
| *A61K 35/12* | (2015.01) |
| *A61K 9/00* | (2006.01) |
| *A61K 9/50* | (2006.01) |
| *A61K 31/7105* | (2006.01) |

(52) U.S. Cl.
CPC .......... *C12N 15/113* (2013.01); *A61K 9/0019* (2013.01); *A61K 9/5068* (2013.01); *A61K 31/7105* (2013.01); *A61K 35/12* (2013.01); *C12N 15/10* (2013.01); *C12N 15/111* (2013.01); *C12N 15/87* (2013.01); *C12Q 1/6881* (2013.01); *C12N 2310/141* (2013.01); *C12N 2310/20* (2017.05); *C12N 2310/531* (2013.01); *C12N 2310/533* (2013.01); *C12N 2320/32* (2013.01); *C12Q 2600/178* (2013.01)

(58) Field of Classification Search
None
See application file for complete search history.

(56) References Cited

U.S. PATENT DOCUMENTS

| 8,273,871 B2 | 1/2012 | Hannon et al. | |
| 2012/0021516 A1* | 1/2012 | Hannon | C12N 15/111 435/375 |
| 2016/0137716 A1* | 5/2016 | El Andaloussi | F01C 1/3442 424/450 |

FOREIGN PATENT DOCUMENTS

| WO | WO 2015/002956 A1 | 1/2015 | |
| WO | WO-2015002956 A1 * | 1/2015 | ............. C12N 15/88 |

OTHER PUBLICATIONS

Khan et al. (Circ. Res. (Apr. 2015); 117:52-64). (Year: 2015).*
Katakowski (Cancer Letters (2013) 335:201-204). (Year: 2013).*
Lindner et al. (Transfus Med Hemother (2010) 37:75-83). (Year: 2010).*
Shelke et al. (J. Extracellular Vesicles (2014) vol. 3, #24783, pp. 1-9). (Year: 2014).*
International Serach Report and Written Opinion for PCT/CA2016/051140, dated Dec. 7, 2016.
International Preliminary Report on Patentability for PCT/CA2016/051140, mailed Apr. 12, 2018.
Amendola et al., Regulated and Multiple miRNA and siRNA Delivery Into Primary Cells by a Lentiviral Platform. Molecular Therapy 2009;17(6):1039-1052. DOI: https://doi.org/10.1038/mt.2009.48.
Guduric-Fuchs et al., Selective extracellular vesicle-mediated export of an overlapping set of microRNAs from multiple cell types. BMC Genomics. Aug. 1, 2012;13:357. doi: 10.1186/1471-2164-13-357.
Haley et al., A simplified miRNA-based gene silencing method for Drosophila melanogaster. Dev Biol. Sep. 15, 2008;321(2):482-490. Published online Jun. 19, 2008. doi: 10.1016/j.ydbio.2008.06.015.
Ma et al., Designing Ago2-specific siRNA/shRNA to Avoid Competition with Endogenous miRNAs. Molecular Therapy—Nucleic Acids 2014;3:e176. ISSN 2162-2531. https://doi.org/10.1038/mtna.2014.27.
EP16849987.9, Feb. 15, 2019, Extended European Search Report.
Extended European Search Report for Application No. EP16849987.9, dated Feb. 15, 2019.
Cifuentes et al., A novel miRNA processing pathway independent of Dicer requires Argonaute2 catalytic activity. Science. Jun. 25, 2010;328(5986):1694-8. doi: 10.1126/science.1190809. Epub May 6, 2010.

(Continued)

*Primary Examiner* — J. E Angell
(74) *Attorney, Agent, or Firm* — Wolf, Greenfield & Sacks, P.C.

(57) ABSTRACT

A method for preparing exosomes or exosome-like vesicles packaged with a nucleic acid of interest is provided. In certain embodiments, the method may comprise: introducing into an exosome-producing cell a nucleic acid construct comprising the nucleic acid sequence of interest incorporated in a pre-miR-451 structural mimic, and allowing the cell to produce exosomes. Nucleic acid constructs, compositions, and uses thereof are also provided.

15 Claims, 28 Drawing Sheets

Specification includes a Sequence Listing.

(56) References Cited

OTHER PUBLICATIONS

Lasser, Exosomal RNA as biomarkers and the therapeutic potential of exosome vectors. Expert Opin Biol Ther. Jun. 2012;12 Suppl 1:S189-97. doi: 10.1517/14712598.2012.680018. Epub Apr. 16, 2012.

Montecalvo et al., Mechanism of transfer of functional microRNAs between mouse dendritic cells via exosomes.Blood. Jan. 19, 2012;119(3):756-66. doi: 10.1182/blood-2011-02-338004. Epub Oct. 26, 2011.

PCT/CA2016/051140, Dec. 7, 2016, International Search Report and Written Opinion.

PCT/CA2016/051140, Apr. 12, 2018, International Preliminary Report on Patentability.

Liu et al., Towards Antiviral shRNAs Based on the AgoshRNA Design. PLoS One. 2015;10(6):e0128618. Published Jun. 18, 2015. doi:10.1371/journal.pone.0128618.

* cited by examiner

SEQ ID NO: 1

5' – AAACCGUUACCAUUACUGAGUUUAGUAAUGGUAAUGGUUCUC – 3'

SEQ ID NO: 2

5' – CUU GGG AAU GGC AAG <u>GAA ACC GUU ACC AUU ACU GAG UUU AGU AAU GGU AAU GGU UCU C</u>UU GCU AUA CCC AGA – 3'

(pre-miR-451 miRNA region underlined)

SEQ ID NO: 3

5' – AA ACC GUU ACC AUU ACU <u>GAG UUU</u> AGU AAU GGU AAU GGU UCU C – 3' (loop region underlined)

SEQ ID NO: 4

5' – AA ACC GUU ACC AUU ACU GAG UUU AGU AAU GG – 3'

SEQ ID NO: 5

5' – AA ACC GUU ACC AUU ACU GAG UUU – 3'

SEQ ID NO: 6

5' – CUUGGGAAUGGCAAGG<u>UUAAUGCUAAUCGUGAUAG</u>GGGG<u>U</u>AUCACGAUUAGCAUUACUCUUGCUAUACCCAGA – 3'

(miR-155 targeting sequence shown in underline; loop shown in bold).

FIGURE 13 (Continued)

SEQ ID NO: 7

5' – CUUGGGAAUGGCAAGG<u>AAAAGUGCUUACAGUGCAGGUA</u>UGCACUGUAAGCACUUUCUCUUGCUAUACCCAGA – 3'

(miR-106 targeting sequence shown in underline; loop shown in bold)

SEQ ID NO: 8

5' – CUUGGGAAUGGCAAGG<u>ACAGUAGUCUGCACAUUGGUUA</u>AUGUGCAGACUACUGUCUCUUGCUAUACCCAGA – 3'

(miR-199 targeting sequence shown in underline; loop shown in bold)

SEQ ID NO: 9

AAACCGTTACCATTACTGAGTT

SEQ ID NO: 10

ACCCCTATCACGATTAGCATTAA

SEQ ID NO: 11

TAACCAATGTGCAGACTACTGT

SEQ ID NO: 12

CTACCTGCACTGTAAGCACTTTT

FIGURE 13 (Continued)

SEQ ID NO: 13

TGAGGTAGTAGGTTGTATAGTT

SEQ ID NO: 14 aaaccgttaccattactgagtt

SEQ ID NO: 15 tgaggtagtaggttgtatagtt

SEQ ID NO: 16 tagcagcacgtaaatattggcg

SEQ ID NO: 17

5' – CUUGGGAAUGGCAAGG<u>UUCAGUCAGUCCUUUAAUGCUU</u>UUUAAAGGACUGACUGACUCUUGCUAUACCCAGA – 3'

SEQ ID NO: 18

TTAAGAATAGTTTTTGCTGTACTTTCTATAGTGAATAGAGTTAGGCAGGGATATTCACCATTATCGTTTCAGACCCACCT

CCCAACCCCGAGGGGACCCGACAGGCCCGAAGGAATAGAAGAAGAAGGTGGAGAG

FIGURE 13 (Continued)

AGAGACAGAGACAGATCCATTCGAT

TAGTGAACGGATCGGCACTGCGTGCGCCAATTCTGCAGACAAATGGCAGTATTCATC
CACAATTTTAAAAGAAAAGGGGG

GATTGGGGGGTACAGTGCAGGGGAAAGAATAGTAGACATAATAGCAACAGACATA
CAAACTAAAGAATTACAAAAACAAA

TTACAAAAATTCAAAATTTTCGGGTTTATTACAGGGACAGCAGAGATCCAGTTTGGT
TAGTACCGGGCCCGCTCTAGTCC

GGAATCAGTCCTGCTCCTCGGCCACGAAGTGCACGCAGTTGCCGGCCGGGTCGCGC
AGGGCGAACTCCCGCCCCACGGC

TGCTCGCCGATCTCGGTCATGGCCGGCCCGGAGGCGTCCCGGAAGTTCGTGGACAC
GACCTCCGACCACTCGGCGTACAG

CTCGTCCAGGCCGCGCACCCACACCCAGGCCAGGGTGTTGTCCGGCACCACCTGGTC
CTGGACCGCGCTGATGAACAGGG

TCACGTCGTCCCGGACCACACCGGCGAAGTCGTCCTCCACGAAGTCCCGGGAGAAC
CCGAGCCGGTCGGTCCAGAACTCG

ACCGCTCCGGCGACGTCGCGCGCGGTGAGCACCGGAACGGCACTGGTCAACTTGGC
CATGGTGGCCCTCCTATAGTGAGT

CGTATTATACTATGCCGATATACTATGCCGATGATTAATTGTCAACACGTGCTGCAG
GTCCGAGGTTCTAGACGTATTAC

CGCCATGCATTAGTTATTAATAGTAATCAATTACGGGGTCATTAGTTCATAGCCCAT
ATATGGAGTTCCGCGTTACATAA

CTTACGGTAAATGGCCCGCCTGGCTGACCGCCCAACGACCCCGCCCATTGACGTCA
ATAATGACGTATGTTCCCATAGT

FIGURE 13 (Continued)

AACGCCAATAGGGACTTTCCATTGACGTCAATGGGTGGAGTATTTACGGTAAACTGC
CCACTTGGCAGTACATCAAGTGT

ATCATATGCCAAGTACGCCCCTATTGACGTCAATGACGGTAAATGGCCCGCCTGGC
ATTATGCCCAGTACATGACCTTA

TGGGACTTTCCTACTTGGCAGTACATCTACGTATTAGTCATCGCTATTACCATGGTGA
TGCGGTTTTGGCAGTACATCAA

TGGGCGTGGATAGCGGTTTGACTCACGGGGATTTCCAAGTCTCCACCCCATTGACGT
CAATGGGAGTTTGTTTTGGCACC

AAAATCAACGGGACTTTCCAAAATGTCGTAACAACTCCGCCCCATTGACGCAAATG
GGCGGTAGGCGTGTACGGTGGGAG

GTCTATATAAGCAGAGCTCGTTTAGTGAACCGTCAGATCGCCTGGAGACGCCATCCA
CGCTGTTTTGACCTCCATAGAAG

ACACCGACTCTACTAGAGGATCTGCCACCATGGAGAGCGACGAGAGCGGCCTGCCC
GCCATGGAGATCGAGTGCCGCATC

ACCGGCACCCTGAACGGCGTGGAGTTCGAGCTGGTGGGCGGCGGAGAGGGCACCCC
CGAGCAGGGCCGCATGACCAACAA

GATGAAGAGCACCAAAGGCGCCCTGACCTTCAGCCCCTACCTGCTGAGCCACGTGA
TGGGCTACGGCTTCTACCACTTCG

GCACCTACCCCAGCGGCTACGAGAACCCCTTCCTGCACGCCATCAACAACGGCGGC
TACACCAACACCCGCATCGAGAAG

TACGAGGACGGCGGCGTGCTGCACGTGAGCTTCAGCTACCGCTACGAGGCCGGCCG
CGTGATCGGCGACTTCAAGGTGAT

GGGCACCGGCTTCCCCGAGGACAGCGTGATCTTCACCGACAAGATCATCCGCAGCA
ACGCCACCGTGGAGCACCTGCACC

FIGURE 13 (Continued)

CCATGGGCGATAACGATCTGGATGGCAGCTTCACCCGCACCTTCAGCCTGCGCGACG
GCGGCTACTACAGCTCCGTGGTG

GACAGCCACATGCACTTCAAGAGCGCCATCCACCCCAGCATCCTGCAGAACGGGGG
CCCCATGTTCGCCTTCCGCCGCGT

GGAGGAGGATCACAGCAACACCGAGCTGGGCATCGTGGAGTACCAGCACGCCTTCA
AGACCCCGGATGCAGATGCCGGTG

AAGAATAATGTACAAGTAGCGGCCGCAAATTCCGCCCCTCTCCCTCCCCCCCCCCTA
ACGTTACTGGCCGAAGCCGCTTG

GAATAAGGCCGGTGTGCGTTTGTCTATATGTTATTTTCCACCATATTGCCGTCTTTTG
GCAATGTGAGGGCCCGGAAACC

TGGCCCTGTCTTCTTGACGAGCATTCCTAGGGGTCTTTCCCCTCTCGCCAAAGGAATG
CAAGGTCTGTTGAATGTCGTGA

AGGAAGCAGTTCCTCTGGAAGCTTCTTGAAGACAAACAACGTCTGTAGCGACCCTTT
GCAGGCAGCGGAACCCCCCACCT

GGCGACAGGTGCCTCTGCGGCCAAAAGCCACGTGTATAAGATACACCTGCAAAGGC
GGCACAACCCCAGTGCCACGTTGT

GAGTTGGATAGTTGTGGAAAGAGTCAAATGGCTCTCCTCAAGCGTATTCAACAAGG
GGCTGAAGGATGCCCAGAAGGTAC

CCCATTGTATGGGATCTGATCTGGGGCCTCGGTGCACATGCTTTACATGTGTTTAGTC
GAGGTTAAAAAAACGTCTAGGC

CCCCCGAACCACGGGGACGTGGTTTTCCTTTGAAAAACACGATAATACCATGGCCAC
CGAGTACAAGCCCACGGTGCGCC

TCGCCACCCGCGACGACGTCCCCCGGGCCGTACGCACCCTCGCCGCCGCGTTCGCCG
ACTACCCCGCCACGCGCCACACC

FIGURE 13 (Continued)

GTCGACCCGGACCGCCACATCGAGCGGGTCACCGAGCTGCAAGAACTCTTCCTCAC
GCGCGTCGGGCTCGACATCGGCAA

GGTGTGGGTCGCGGACGACGGCGCCGCGGTGGCGGTCTGGACCACGCCGGAGAGCG
TCGAAGCGGGGGCGGTGTTCGCCG

AGATCGGCTCGCGCATGGCCGAGTTGAGCGGTTCCCGGCTGGCCGCGCAGCAACAG
ATGGAAGGCCTCCTGGCGCCGCAC

CGGCCCAAGGAGCCCGCGTGGTTCCTGGCCACCGTCGGCGTCTCGCCCGACCACCA
GGGCAAGGGTCTGGGCAGCGCCGT

CGTGCTCCCCGGAGTGGAGGCGGCCGAGCGCGCTGGGGTGCCCGCCTTCCTGGAGA
CCTCCGCGCCCCGCAACCTCCCCT

TCTACGAGCGGCTCGGCTTCACCGTCACCGCCGACGTCGAGGTGCCCGAAGGACCG
CGCACCTGGTGCATGACCCGCAAG

CCCGGTGCCTGAGTTTGTTTGAATGAGGCTTCAGTACTTTACAGAATCGTTGCCTGC
ACATCTTGGAAACACTTGCTGGG

ATTACTTCTTCAGGTTAACCCAACAGAAGGCTCGAGGTAACCGGATCCTGATCAGAA
TTCAAGGGGCTACTTTAGGAGCA

ATTATCTTGTTTACTAAAACTGAATACCTTGCTATCTCTTTGATACATTTTTACAAAG
CTGAATTAAAATGGTATAAATT

AAATCACTTTTTTCAATTGGAAGACTAATGCGGCCGGCCATTACTCCGTCTCGTGTCT
TGTTGCATATGTCTGCTGGTTT

GTTTGATGTTGTTTGCGGGCGGGCCCTATAGTGAGTCGTATTACCTAGGACGCGTCT
GGAACAATCAACCTCTGGATTAC

AAAATTTGTGAAAGATTGACTGGTATTCTTAACTATGTTGCTCCTTTTACGCTATGTG
GATACGCTGCTTTAATGCCTTT

FIGURE 13 (Continued)

GTATCATGCTATTGCTTCCCGTATGGCTTTCATTTTCTCCTCCTTGTATAAATCCTGGT
TGCTGTCTCTTTATGAGGAGT

TGTGGCCCGTTGTCAGGCAACGTGGCGTGGTGTGCACTGTGTTTGCTGACGCAACCC
CCACTGGTTGGGGCATTGCCACC

ACCTGTCAGCTCCTTTCCGGGACTTTCGCTTTCCCCCTCCCTATTGCCACGGCGGAAC
TCATCGCCGCCTGCCTTGCCCG

CTGCTGGACAGGGGCTCGGCTGTTGGGCACTGACAATTCCGTGGTGTTGTCGGGGAA
GCTGACGTCCTTTCCATGGCTGC

TCGCCTGTGTTGCCACCTGGATTCTGCGCGGGACGTCCTTCTGCTACGTCCCTTCGGC
CCTCAATCCAGCGGACCTTCCT

TCCCGCGGCCTGCTGCCGGCTCTGCGGCCTCTTCCGCGTCTTCGCCTTCGCCCTCAGA
CGAGTCGGATCTCCCTTTGGGC

CGCCTCCCCGCCTGGAATTAATTCTGCAGTCGAGACCTAGAAAAACATGGAGCAAT
CACAAGTAGCAATACAGCAGCTAC

CAATGCTGATTGTGCCTGGCTAGAAGCACAAGAGGAGGAGGAGGTGGGTTTTCCAG
TCACACCTCAGGTACCTTTAAGAC

CAATGACTTACAAGGCAGCTGTAGATCTTAGCCACTTTTTAAAAGAAAAGAGGGGA
CTGGAAGGGCTAATTCACTCCCAA

CGAAGACAAGATCTGCTTTTTGCTTGTACTGGGTCTCTCTGGTTAGACCAGATCTGA
GCCTGGGAGCTCTCTGGCTAACT

AGGGAACCCACTGCTTAAGCCTCAATAAAGCTTGCCTTGAGTGCTTCAAGTAGTGTG
TGCCCGTCTGTTGTGTGACTCTG

GTAACTAGAGATCCCTCAGACCCTTTTAGTCAGTGTGGAAAATCTCTAGCAGTAGTA
GTTCATGTCATCTTATTATTCAG

FIGURE 13 (Continued)

TATTTATAACTTGCAAAGAAATGAATATCAGAGAGTGAGAGGCCTTGACATTGTTTA
AACCCGCTGATCAGCCTCGACTG

TGCCTTCTAGTTGCCAGCCATCTGTTGTTTGCCCCTCCCCCGTGCCTTCCTTGACCCT
GGAAGGTGCCACTCCCACTGTC

CTTTCCTAATAAAATGAGGAAATTGCATCGCATTGTCTGAGTAGGTGTCATTCTATTC
TGGGGGGTGGGGTGGGGCAGGA

CAGCAAGGGGGAGGATTGGGAAGACAATAGCAGGCATGCTGGGGATGCGGTGGGC
TCTATGGCTTCTGAGGCGGAAAGAA

CCAGCTGGGGCTCTAGGGGGTATCCCCACGCGCCCTGTAGCGGCGCATTAAGCGCG
GCGGGTGTGGTGGTTACGCGCAGC

GTGACCGCTACACTTGCCAGCGCCCTAGCGCCCGCTCCTTTCGCTTTCTTCCCTTCCT
TTCTCGCCACGTTCGCCGGCTT

TCCCCGTCAAGCTCTAAATCGGGGGCTCCCTTTAGGGTTCCGATTTAGTGCTTTACGG
CACCTCGACCCCAAAAAACTTG

ATTAGGGTGATGGTTCACGTAGTGGGCCATCGCCCTGATAGACGGTTTTTCGCCCTT
TGACGTTGGAGTCCACGTTCTTT

AATAGTGGACTCTTGTTCCAAACTGGAACAACACTCAACCCTATCTCGGTCTATTCTT
TTGATTTATAAGGGATTTTGCC

GATTTCGGCCTATTGGTTAAAAAATGAGCTGATTTAACAAAAATTTAACGCGAATTA
ATTCTGTGGAATGTGTGTCAGTT

AGGGTGTGGAAAGTCCCCAGGCTCCCCAGCAGGCAGAAGTATGCAAAGCATGCATC
TCAATTAGTCAGCAACCAGGTGTG

GAAAGTCCCCAGGCTCCCCAGCAGGCAGAAGTATGCAAAGCATGCATCTCAATTAG
TCAGCAACCATAGTCCCGCCCCTA

FIGURE 13 (Continued)

ACTCCGCCCATCCCGCCCCTAACTCCGCCCAGTTCCGCCCATTCTCCGCCCCATGGCT
GACTAATTTTTTTATTTATGC

AGAGGCCGAGGCCGCCTCTGCCTCTGAGCTATTCCAGAAGTAGTGAGGAGGCTTTTT
TGGAGGCCTAGGCTTTTGCAAAA

AGCTCCCGGGAGCTTGTATATCCATTTTCGGATCTGATCAGCACGTGATGAAAAGC
CTGAACTCACCGCGACGTCTGTC

GAGAAGTTTCTGATCGAAAAGTTCGACAGCGTCTCCGACCTGATGCAGCTCTCGGAG
GGCGAAGAATCTCGTGCTTTCAG

CTTCGATGTAGGAGGGCGTGGATATGTCCTGCGGGTAAATAGCTGCGCCGATGGTTT
CTACAAGATCGTTATGTTTATC

GGCACTTTGCATCGGCCGCGCTCCCGATTCCGGAAGTGCTTGACATTGGGGAATTCA
GCGAGAGCCTGACCTATTGCATC

TCCCGCCGTGCACAGGGTGTCACGTTGCAAGACCTGCCTGAAACCGAACTGCCCGCT
GTTCTGCAGCCGGTCGCGGAGGC

CATGGATGCGATCGCTGCGGCCGATCTTAGCCAGACGAGCGGGTTCGGCCCATTCG
GACCGCAAGGAATCGGTCAATACA

CTACATGGCGTGATTTCATATGCGCGATTGCTGATCCCCATGTGTATCACTGGCAAA
CTGTGATGGACGACACCGTCAGT

GCGTCCGTCGCGCAGGCTCTCGATGAGCTGATGCTTTGGGCCGAGGACTGCCCCGAA
GTCCGGCACCTCGTGCACGCGGA

TTTCGGCTCCAACAATGTCCTGACGGACAATGGCCGCATAACAGCGGTCATTGACTG
GAGCGAGGCGATGTTCGGGGATT

CCCAATACGAGGTCGCCAACATCTTCTTCTGGAGGCCGTGGTTGGCTTGTATGGAGC
AGCAGACGCGCTACTTCGAGCGG

FIGURE 13 (Continued)

AGGCATCCGGAGCTTGCAGGATCGCCGCGGCTCCGGGCGTATATGCTCCGCATTGGT
CTTGACCAACTCTATCAGAGCTT

GGTTGACGGCAATTTCGATGATGCAGCTTGGGCGCAGGGTCGATGCGACGCAATCG
TCCGATCCGGAGCCGGGACTGTCG

GGCGTACACAAATCGCCCGCAGAAGCGCGGCCGTCTGGACCGATGGCTGTGTAGAA
GTACTCGCCGATAGTGGAAACCGA

CGCCCCAGCACTCGTCCGAGGGCAAAGGAATAGCACGTGCTACGAGATTTCGATTC
CACCGCCGCCTTCTATGAAAGGTT

GGGCTTCGGAATCGTTTTCCGGGACGCCGGCTGGATGATCCTCCAGCGCGGGGATCT
CATGCTGGAGTTCTTCGCCCACC

CCAACTTGTTTATTGCAGCTTATAATGGTTACAAATAAAGCAATAGCATCACAAATT
TCACAAATAAAGCATTTTTTTCA

CTGCATTCTAGTTGTGGTTTGTCCAAACTCATCAATGTATCTTATCATGTCTGTATAC
CGTCGACCTCTAGCTAGAGCTT

GGCGTAATCATGGTCATAGCTGTTTCCTGTGTGAAATTGTTATCCGCTCACAATTCCA
CACAACATACGAGCCGGAAGCA

TAAAGTGTAAAGCCTGGGGTGCCTAATGAGTGAGCTAACTCACATTAATTGCGTTGC
GCTCACTGCCCGCTTTCCAGTCG

GGAAACCTGTCGTGCCAGCTGCATTAATGAATCGGCCAACGCGCGGGGAGAGGCGG
TTTGCGTATTGGGCGCTCTTCCGC

TTCCTCGCTCACTGACTCGCTGCGCTCGGTCGTTCGGCTGCGGCGAGCGGTATCAGC
TCACTCAAAGGCGGTAATACGGT

TATCCACAGAATCAGGGGATAACGCAGGAAAGAACATGTGAGCAAAAGGCCAGCA
AAAGGCCAGGAACCGTAAAAGGCC

FIGURE 13 (Continued)

GCGTTGCTGGCGTTTTTCCATAGGCTCCGCCCCCTGACGAGCATCACAAAAATCGA
CGCTCAAGTCAGAGGTGGCGAAA

CCCGACAGGACTATAAAGATACCAGGCGTTTCCCCCTGGAAGCTCCCTCGTGCGCTC
TCCTGTTCCGACCCTGCCGCTTA

CCGGATACCTGTCCGCCTTTCTCCCTTCGGGAAGCGTGGCGCTTTCTCATAGCTCACG
CTGTAGGTATCTCAGTTCGGTG

TAGGTCGTTCGCTCCAAGCTGGGCTGTGTGCACGAACCCCCGTTCAGCCCGACCGC
TGCGCCTTATCCGGTAACTATCG

TCTTGAGTCCAACCCGGTAAGACACGACTTATCGCCACTGGCAGCAGCCACTGGTAA
CAGGATTAGCAGAGCGAGGTATG

TAGGCGGTGCTACAGAGTTCTTGAAGTGGTGGCCTAACTACGGCTACACTAGAAGA
ACAGTATTTGGTATCTGCGCTCTG

CTGAAGCCAGTTACCTTCGGAAAAAGAGTTGGTAGCTCTTGATCCGGCAAACAAAC
CACCGCTGGTAGCGGTGGTTTTT

TGTTTGCAAGCAGCAGATTACGCGCAGAAAAAAGGATCTCAAGAAGATCCTTTGA
TCTTTTCTACGGGGTCTGACGCTC

AGTGGAACGAAAACTCACGTTAAGGGATTTTGGTCATGAGATTATCAAAAGGATC
TTCACCTAGATCCTTTTAAATTAA

AAATGAAGTTTTAAATCAATCTAAAGTATATATGAGTAAACTTGGTCTGACAGTTAC
CAATGCTTAATCAGTGAGGCACC

TATCTCAGCGATCTGTCTATTTCGTTCATCCATAGTTGCCTGACTCCCCGTCGTGTAG
ATAACTACGATACGGGAGGGCT

TACCATCTGGCCCCAGTGCTGCAATGATACCGCGAGACCCACGCTCACCGGCTCCAG
ATTTATCAGCAATAAACCAGCCA

FIGURE 13 (Continued)

GCCGGAAGGGCCGAGCGCAGAAGTGGTCCTGCAACTTTATCCGCCTCCATCCAGTCT
ATTAATTGTTGCCGGGAAGCTAG

AGTAAGTAGTTCGCCAGTTAATAGTTTGCGCAACGTTGTTGCCATTGCTACAGGCAT
CGTGGTGTCACGCTCGTCGTTTG

GTATGGCTTCATTCAGCTCCGGTTCCCAACGATCAAGGCGAGTTACATGATCCCCA
TGTTGTGCAAAAAAGCGGTTAGC

TCCTTCGGTCCTCCGATCGTTGTCAGAAGTAAGTTGGCCGCAGTGTTATCACTCATG
GTTATGGCAGCACTGCATAATTC

TCTTACTGTCATGCCATCCGTAAGATGCTTTTCTGTGACTGGTGAGTACTCAACCAAG
TCATTCTGAGAATAGTGTATGC

GGCGACCGAGTTGCTCTTGCCCGGCGTCAATACGGGATAATACCGCGCCACATAGC
AGAACTTTAAAAGTGCTCATCATT

GGAAAACGTTCTTCGGGGCGAAAACTCTCAAGGATCTTACCGCTGTTGAGATCCAGT
TCGATGTAACCCACTCGTGCACC

CAACTGATCTTCAGCATCTTTTACTTTCACCAGCGTTTCTGGGTGAGCAAAAACAGG
AAGGCAAAATGCCGCAAAAAAGG

GAATAAGGGCGACACGGAAATGTTGAATACTCATACTCTTCCTTTTTCAATATTATT
GAAGCATTTATCAGGGTTATTGT

CTCATGAGCGGATACATATTTGAATGTATTTAGAAAAATAAACAAATAGGGGTTCCG
CGCACATTTCCCCGAAAAGTGCC

ACCTGACGTCGACGGATCGGGAGATCAACTTGTTTATTGCAGCTTATAATGGTTACA
AATAAAGCAATAGCATCACAAAT

TTCACAAATAAAGCATTTTTTTCACTGCATTCTAGTTGTGGTTTGTCCAAACTCATCA
ATGTATCTTATCATGTCTGGAT

FIGURE 13 (Continued)

CAACTGGATAACTCAAGCTAACCAAAATCATCCCAAACTTCCCACCCCATACCCTAT
TACCACTGCCAATTACCTGTGGT

TTCATTTACTCTAAACCTGTGATTCCTCTGAATTATTTTCATTTTAAAGAAATTGTATT
TGTTAAATATGTACTACAAAC

TTAGTAGT

SEQ ID NO: 19

5' – CUUGGGAAUGGCAAGG<u>AUGAACUUCAGGGUCAGCUUGC</u>GCUGACCCUGAAG
UUCAUUCUUGCUAUACCCAGA

SEQ ID NO: 20

5' – CUUGGGAAUGGCAAGG<u>UCUUGAUCUUCCAAUACGCAAC</u>CGUAUUGGAAGAU
CAAGAUCUUGCUAUACCCAGA

SEQ ID NO: 21

5' – atgaacttcagggtcagcttgc

SEQ ID NO: 22

5' – tcttgatcttccaatacgcaac

FIGURE 13 (Continued)

SEQ ID NO: 23

5' – ttcagtcagtcctttaatgctt

SEQ ID NO: 24 tagcagcacgtaaatattggcg

SEQ ID NO: 25 augaacuucagggucagcuugcgcugaccc

SEQ ID NO: 26

AUGAACUUCAGGGUCAGCUUGCGCUGACCCUGAAGUUCAUUC

SEQ ID NO: 27

AUGAACUUCAGGGUCAGCUUGC

SEQ ID NO: 28

AAGCUGACCCUGAAGUUCAUUC

SEQUENCE LISTING

```
<160> NUMBER OF SEQ ID NOS: 28

<210> SEQ ID NO 1
<211> LENGTH: 42
<212> TYPE: RNA
<213> ORGANISM: Homo Sapiens

<400> SEQUENCE: 1
aaaccguuac cauuacugag uuuaguaaug guaaugguuc uc                      42

<210> SEQ ID NO 2
<211> LENGTH: 72
<212> TYPE: RNA
<213> ORGANISM: Homo Sapiens

<400> SEQUENCE: 2
cuugggaaug gcaaggaaac cguuaccauu acugaguuua guaaugguaa ugguucucuu    60
gcuauaccca ga                                                       72

<210> SEQ ID NO 3
<211> LENGTH: 42
<212> TYPE: RNA
<213> ORGANISM: Homo Sapiens

<400> SEQUENCE: 3
aaaccguuac cauuacugag uuuaguaaug guaaugguuc uc                      42

<210> SEQ ID NO 4
<211> LENGTH: 31
<212> TYPE: RNA
<213> ORGANISM: Homo Sapiens

<400> SEQUENCE: 4
aaaccguuac cauuacugag uuuaguaaug g                                  31
```

```
<210> SEQ ID NO 5
<211> LENGTH: 23
<212> TYPE: RNA
<213> ORGANISM: Homo Sapiens

<400> SEQUENCE: 5
aaaccguuac cauuacugag uuu                                               23

<210> SEQ ID NO 6
<211> LENGTH: 72
<212> TYPE: RNA
<213> ORGANISM: Artificial Sequence
<220> FEATURE:
<223> OTHER INFORMATION: pre-miR-451 structural mimic comprising miR-155
      targeting sequence

<400> SEQUENCE: 6
cuugggaaug gcaagguuaa ugcuaaucgu gauagggua ucacgauuag cauuacucuu        60
gcuauaccca ga                                                           72

<210> SEQ ID NO 7
<211> LENGTH: 72
<212> TYPE: RNA
<213> ORGANISM: Artificial Sequence
<220> FEATURE:
<223> OTHER INFORMATION: pre-miR-451 structural mimic comprising miR-106
      targeting sequence

<400> SEQUENCE: 7
cuugggaaug gcaaggaaaa gugcuuacag ugcagguaug cacuguaagc acuuucucuu        60
gcuauaccca ga                                                           72

<210> SEQ ID NO 8
<211> LENGTH: 71
<212> TYPE: RNA
<213> ORGANISM: Artificial Sequence
<220> FEATURE:
<223> OTHER INFORMATION: pre-miR-451 structural mimic comprising miR-199
      targeting sequence

<400> SEQUENCE: 8
cuugggaaug gcaaggacag uagucugcac auugguuaau gugcagacua cugucucuug        60
cuauacccag a                                                            71

<210> SEQ ID NO 9
<211> LENGTH: 22
<212> TYPE: DNA
<213> ORGANISM: Artificial Sequence
<220> FEATURE:
<223> OTHER INFORMATION: miR-451 primer

<400> SEQUENCE: 9
aaaccgttac cattactgag tt                                                22

<210> SEQ ID NO 10
<211> LENGTH: 23
<212> TYPE: DNA
<213> ORGANISM: Artificial Sequence
<220> FEATURE:
<223> OTHER INFORMATION: miR-155 primer

<400> SEQUENCE: 10
acccctatca cgattagcat taa                                               23
```

```
<210> SEQ ID NO 11
<211> LENGTH: 22
<212> TYPE: DNA
<213> ORGANISM: Artificial Sequence
<220> FEATURE:
<223> OTHER INFORMATION: miR-199 primer

<400> SEQUENCE: 11
taaccaatgt gcagactact gt                                              22

<210> SEQ ID NO 12
<211> LENGTH: 23
<212> TYPE: DNA
<213> ORGANISM: Artificial Sequence
<220> FEATURE:
<223> OTHER INFORMATION: miR-106a primer

<400> SEQUENCE: 12
ctacctgcac tgtaagcact ttt                                             23

<210> SEQ ID NO 13
<211> LENGTH: 22
<212> TYPE: DNA
<213> ORGANISM: Artificial Sequence
<220> FEATURE:
<223> OTHER INFORMATION: let-7a primer

<400> SEQUENCE: 13
tgaggtagta ggttgtatag tt                                              22

<210> SEQ ID NO 14
<211> LENGTH: 22
<212> TYPE: DNA
<213> ORGANISM: Artificial Sequence
<220> FEATURE:
<223> OTHER INFORMATION: miR-451 primer

<400> SEQUENCE: 14
aaaccgttac cattactgag tt                                              22

<210> SEQ ID NO 15
<211> LENGTH: 22
<212> TYPE: DNA
<213> ORGANISM: Artificial Sequence
<220> FEATURE:
<223> OTHER INFORMATION: let-7a primer

<400> SEQUENCE: 15
tgaggtagta ggttgtatag tt                                              22

<210> SEQ ID NO 16
<211> LENGTH: 22
<212> TYPE: DNA
<213> ORGANISM: Artificial Sequence
<220> FEATURE:
<223> OTHER INFORMATION: miR-16 primer

<400> SEQUENCE: 16
tagcagcacg taaatattgg cg                                              22

<210> SEQ ID NO 17
<211> LENGTH: 72
<212> TYPE: RNA
<213> ORGANISM: Artificial Sequence
<220> FEATURE:
<223> OTHER INFORMATION: pre-miR-451 structural mimic targeting SOD1
```

<400> SEQUENCE: 17

```
cuugggaaug gcaagguuca gucaguccuu uaaugcuuuu uaaaggacug acugacucuu      60
gcuauaccca ga                                                         72
```

<210> SEQ ID NO 18
<211> LENGTH: 9848
<212> TYPE: DNA
<213> ORGANISM: Artificial Sequence
<220> FEATURE:
<223> OTHER INFORMATION: pGIPZ sequence with inserted pre-miR-451
      structural mimic targeting S0D1

<400> SEQUENCE: 18

```
ttaagaatag ttttgctgt actttctata gtgaatagag ttaggcaggg atattcacca       60
ttatcgtttc agaccacct cccaacccg aggggacccg acaggcccga aggaatagaa      120
gaagaaggtg gagagagaga cagagacaga tccattcgat tagtgaacgg atcggcactg    180
cgtgcgccaa ttctgcagac aaatggcagt attcatccac aattttaaaa gaaaaggggg    240
gattgggggg tacagtgcag gggaaagaat agtagacata atagcaacag acatacaaac    300
taaagaatta caaaaacaaa ttacaaaaat tcaaatttt cgggtttatt acagggacag    360
cagagatcca gtttggttag taccgggccc gctctagtcc ggaatcagtc ctgctcctcg    420
gccacgaagt gcacgcagtt gccggccggg tcgcgcaggg cgaactcccg ccccacggc     480 tgctcgccga tctcggtcat ggccggcccg gaggcgtccc ggaagttcgt ggacacgacc    540
tccgaccact cggcgtacag ctcgtccagg ccgcgcaccc acaccaggc cagggtgttg    600 tccggcacca cctggtcctg gaccgcgctg atgaacaggg tcacgtcgtc ccggaccaca    660
ccggcgaagt cgtcctccac gaagtccgg gagaaccga gccggtcggt ccagaactcg    720
accgctccgg cgacgtcgcg cgcggtgagc accggaacgg cactggtcaa cttggccatg    780
gtggccctcc tatagtgagt cgtattatac tatgccgata tactatgccg atgattaatt    840
gtcaacacgt gctgcaggtc cgaggttcta gacgtattac cgccatgcat tagttattaa    900
tagtaatcaa ttacgggggtc attagttcat agcccatata tggagttccg cgttacataa    960
cttacggtaa atgccccgcc tggctgaccg cccaacgacc cccgcccatt gacgtcaata   1020
atgacgtatg ttcccatagt aacgccaata gggactttcc attgacgtca atggtggag   1080 tatttacggt aaactgccca cttggcagta catcaagtgt atcatatgcc aagtacgccc   1140
cctattgacg tcaatgacgg taaatggccc gcctggcatt atgcccagta catgaccta    1200 tgggactttc ctacttggca gtacatctac gtattagtca tcgctattac catggtgatg   1260
cggttttggc agtacatcaa tgggcgtgga tagcggtttg actcacgggg atttccaagt   1320 ctccaccca ttgacgtcaa tgggagtttg ttttggcacc aaaatcaacg ggactttcca   1380
aaatgtcgta caactccgc cccattgacg caaatgggcg gtaggcgtgt acggtgggag    1440
gtctatataa gcagagctcg tttagtgaac cgtcagatcg cctggagacg ccatccacgc   1500
tgttttgacc tccatagaag acaccgactc tactagagga tctgccacca tggagagcga   1560
cgagagcggc ctgccgcca tggagatcga gtgccgcatc accggcaccc tgaacggcgt   1620
ggagttcgag ctggtgggcg gcggagaggg caccccgag cagggccgca tgaccaacaa   1680
gatgaagagc accaaggcg ccctgacctt cagcccctac ctgctgagcc acgtgatggg   1740
ctacggcttc taccacttcg gcacctaccc cagcggctac gagaaccctt tcctgcacgc   1800
catcaacaac ggcggctaca ccaacacccg catcgagaag tacgaggacg gcggcgtgct   1860
```

```
gcacgtgagc ttcagctacc gctacgaggc cggccgcgtg atcggcgact tcaaggtgat   1920
gggcaccggc ttccccgagg acagcgtgat cttcaccgac aagatcatcc gcagcaacgc   1980
caccgtggag cacctgcacc ccatgggcga taacgatctg gatggcagct tcacccgcac   2040
cttcagcctg cgcgacggcg gctactacag ctccgtggtg gacagccaca tgcacttcaa   2100
gagcgccatc cacccccagca tcctgcagaa cggggggcccc atgttcgcct ccgccgcgt   2160
ggaggaggat cacagcaaca ccgagctggg catcgtggag taccagcacg ccttcaagac   2220
cccggatgca gatgccggtg aagaataatg tacaagtagc ggccgcaaat ccgcccctc   2280
tccctccccc ccccctaacg ttactggccg aagccgcttg gaataaggcc ggtgtgcgtt   2340
tgtctatatg ttattttcca ccatattgcc gtcttttggc aatgtgaggg cccggaaacc   2400
tggccctgtc ttcttgacga gcattcctag gggtctttcc cctctcgcca aggaatgca   2460
aggtctgttg aatgtcgtga aggaagcagt tcctctggaa gcttcttgaa gacaaacaac   2520
gtctgtagcg accctttgca ggcagcggaa ccccccacct ggcgacaggt gcctctgcgg   2580
ccaaaagcca cgtgtataag atacacctgc aaaggcggca caaccccagt gccacgttgt   2640
gagttggata ttgtggaaaa gagtcaaatg gctctcctca agcgtattca acaaggggct   2700
gaaggatgcc cagaaggtac cccattgtat gggatctgat ctggggcctc ggtgcacatg   2760
ctttacatgt gtttagtcga ggttaaaaaa acgtctaggc ccccgaacc acggggacgt   2820
ggttttcctt tgaaaacac gataatacca tggccaccga gtacaagccc acggtgcgcc   2880
tcgccacccg cgacgacgtc ccccgggccg tacgcaccct cgccgccgcg ttcgccgact   2940
accccgccac gcgccacacc gtcgaccggg accgccacat cgagcgggtc accgagctgc   3000
aagaactctt cctcacgcgc gtcgggctcg acatcggcaa ggtgtgggtc gcggacgacg   3060
gcgccgcggt ggcggtctgg accacgccgg agagcgtcga agcgggggcg gtgttcgccg   3120
agatcggctc gcgcatggcc gagttgagcg gttcccggct ggccgcgcag caacagatgg   3180
aaggcctcct ggccgccgcac cggcccaagg agcccgcgtg gttcctggcc accgtcggcg   3240
tctcgcccga ccaccagggc aagggtctgg gcagcgccgt cgtgctcccc ggagtggagg   3300
cggccgagcg cgctggggtg cccgccttcc tggagacctc cgcgccccgc aacctcccct   3360
tctacgagcg gctcggcttc accgtcaccg ccgacgtcga ggtgcccgaa ggaccgcgca   3420
cctggtgcat gacccgcaag cccggtgcct gagtttgttt gaatgaggct tcagtacttt   3480
acagaatcgt tgcctgcaca tcttggaaac acttgctggg attacttctt caggttaacc   3540
caacagaagg ctcgaggtaa ccggatcctg atcagaattc aagggctac tttaggagca   3600
attatcttgt ttactaaaac tgaataccct tgctatctct tgatacattt ttacaaagct   3660
gaattaaaat ggtataaatt aaatcacttt tttcaattgg aagactaatg cggccggcca   3720
ttactccgtc tcgtgtcttg ttgcatatgt ctgctggttt gtttgatgtt gtttgcgggc   3780
gggccctata gtgagtcgta ttacctagga cgcgtctgga acaatcaacc tctgattac   3840
aaaatttgtg aaagattgac tggtattctt aactatgttg ctccttttac gctatgtgga   3900
tacgctgctt taatgccttt gtatcatgct attgcttccc gtatggcttt cattttctcc   3960
tccttgtata aatcctggtt gctgtctctt tatgaggagt tgtggcccgt tgtcaggcaa   4020
cgtggcgtgg tgtgcactgt gtttgctgac gcaacccccca ctggttgggg cattgccacc   4080
acctgtcagc tccttttccgg gactttcgct ttcccctcc ctattgccac ggcggaactc   4140
atcgccgcct gccttgcccg ctgctggaca ggggctcggc tgttgggcac tgacaattcc   4200
gtggtgttgt cggggaagct gacgtccttt ccatggctgc tcgcctgtgt tgccacctgg   4260
```

```
attctgcgcg ggacgtcctt ctgctacgtc ccttcggccc tcaatccagc ggaccttcct    4320
tcccgcggcc tgctgccggc tctgcggcct cttccgcgtc ttcgccttcg ccctcagacg    4380
agtcggatct cccttttgggc cgcctccccg cctggaatta attctgcagt cgagacctag    4440
aaaaacatgg agcaatcaca agtagcaata cagcagctac caatgctgat tgtgcctggc    4500
tagaagcaca agaggaggag gaggtgggtt ttccagtcac acctcaggta cctttaagac    4560
caatgactta caaggcagct gtagatctta gccactttt aaaagaaaag aggggactgg    4620
aagggctaat tcactcccaa cgaagacaag atctgctttt tgcttgtact gggtctctct    4680
ggttagacca gatctgagcc tgggagctct ctggctaact agggaaccca ctgcttaagc    4740
ctcaataaag cttgccttga gtgcttcaag tagtgtgtgc ccgtctgttg tgtgactctg    4800
gtaactagag atccctcaga ccctttagt cagtgtggaa aatctctagc agtagtagtt    4860
catgtcatct tattattcag tatttataac ttgcaaagaa atgaatatca gagagtgaga    4920
ggccttgaca ttgtttaaac ccgctgatca gcctcgactg tgccttctag ttgccagcca    4980
tctgttgttt gccccctcccc cgtgccttcc ttgaccctgg aaggtgccac tcccactgtc    5040
ctttcctaat aaaatgagga aattgcatcg cattgtctga gtaggtgtca ttctattctg    5100
gggggtgggg tggggcagga cagcaagggg gaggattggg aagacaatag caggcatgct    5160
ggggatgcgg tgggctctat ggcttctgag gcggaaagaa ccagctgggg ctctagggg    5220
tatccccacg cgccctgtag cggcgcatta agcgcggcgg gtgtggtggt tacgcgcagc    5280
gtgaccgcta cacttgccag cgccctagcg cccgctcctt tcgctttctt cccttccttt    5340
ctcgccacgt tcgccggctt tccccgtcaa gctctaaatc gggggctccc tttagggttc    5400
cgatttagtg ctttacggca cctcgacccc aaaaaacttg attagggtga tggttcacgt    5460
agtgggccat cgccctgata acggttttt cgcccttga cgttggagtc cacgttcttt    5520
aatagtggac tcttgttcca aactggaaca cactcaacc ctatctcggt ctattctttt    5580
gatttataag ggattttgcc gatttcggcc tattggttaa aaaatgagct gatttaacaa    5640
aaatttaacg cgaattaatt ctgtggaatg tgtgtcagtt agggtgtgga aagtccccag    5700
gctccccagc aggcagaagt atgcaaagca tgcatctcaa ttagtcagca accaggtgtg    5760
gaaagtcccc aggctcccca gcaggcagaa gtatgcaaag catgcatctc aattagtcag    5820
caaccatagt cccgccccta actccgccca tcccgcccct aactccgccc agttccgccc    5880
attctccgcc ccatggctga ctaattttt ttatttatgc agaggccgag gccgcctctg    5940
cctctgagct attccagaag tagtgaggag gctttttgg aggcctaggc ttttgcaaaa    6000
agctcccggg agcttgtata tccatttcg gatctgatca gcacgtgatg aaaaagcctg    6060
aactcaccgc gacgtctgtc gagaagtttc tgatcgaaaa gttcgacagc gtctccgacc    6120
tgatgcagct ctcggagggc gaagaatctc gtgctttcag cttcgatgta ggagggcgtg    6180
gatatgtcct gcgggtaaat agctgcgccg atggtttcta caaagatcgt tatgtttatc    6240
ggcactttgc atcggccgcg ctcccgattc cggaagtgct tgacattggg gaattcagcg    6300
agagcctgac ctattgcatc tcccgccgtg cacagggtgt cacgttgcaa gacctgcctg    6360
aaaccgaact gcccgctgtt ctgcagccgg tcgcggaggc catggatgcg atcgctgcgg    6420
ccgatcttag ccagacgagc gggttcggcc cattcggacc gcaaggaatc ggtcaataca    6480
ctacatggcg tgatttcata tgcgcgattg ctgatcccca tgtgtatcac tggcaaactg    6540
tgatggacga caccgtcagt gcgtccgtcg cgcaggctct cgatgagctg atgctttggg    6600
```

```
ccgaggactg ccccgaagtc cggcacctcg tgcacgcgga tttcggctcc aacaatgtcc    6660
tgacggacaa tggccgcata acagcggtca ttgactggag cgaggcgatg ttcggggatt    6720
cccaatacga ggtcgccaac atcttcttct ggaggccgtg gttggcttgt atggagcagc    6780
agacgcgcta cttcgagcgg aggcatccgg agcttgcagg atcgccgcgg ctccgggcgt    6840
atatgctccg cattggtctt gaccaactct atcagagctt ggttgacggc aatttcgatg    6900
atgcagcttg ggcgcagggt cgatgcgacg caatcgtccg atccggagcc gggactgtcg    6960
ggcgtacaca aatcgcccgc agaagcgcgg ccgtctggac cgatggctgt gtagaagtac    7020
tcgccgatag tggaaaccga cgccccagca ctcgtccgag ggcaaaggaa tagcacgtgc    7080
tacgagattt cgattccacc gccgccttct atgaaaggtt gggcttcgga atcgttttcc    7140
gggacgccgg ctggatgatc ctccagcgcg ggatctcat gctggagttc ttcgcccacc     7200
ccaacttgtt tattgcagct tataatggtt acaaataaag caatagcatc acaaatttca    7260
caaataaagc attttttca ctgcattcta gttgtggttt gtccaaactc atcaatgtat     7320
cttatcatgt ctgtataccg tcgacctcta gctagagctt ggcgtaatca tggtcatagc    7380
tgtttcctgt gtgaaattgt tatccgctca caattccaca acatacga gccggaagca     7440 taaagtgtaa agcctggggt gcctaatgag tgagctaact cacattaatt gcgttgcgct    7500
cactgcccgc tttccagtcg ggaaacctgt cgtgccagct gcattaatga atcggccaac    7560 gcgcgggag aggcggtttg cgtattgggc gctcttccgc ttcctcgctc actgactcgc     7620
tgcgctcggt cgttcggctg cggcgagcgg tatcagctca ctcaaaggcg gtaatacggt    7680
tatccacaga atcaggggat aacgcaggaa agaacatgtg agcaaaaggc cagcaaaagg    7740
ccaggaaccg taaaaaggcc gcgttgctgg cgttttcca taggctccgc cccctgacg     7800 agcatcacaa aaatcgacgc tcaagtcaga ggtggcgaaa cccgacagga ctataaagat    7860
accaggcgtt ccccctgga agctccctcg tgcgctctcc tgttccgacc ctgccgctta    7920
ccggatacct gtccgccttt ctcccttcgg gaagcgtggc gctttctcat agctcacgct    7980
gtaggtatct cagttcggtg taggtcgttc gctccaagct gggctgtgtg cacgaacccc    8040
ccgttcagcc cgaccgctgc gccttatccg gtaactatcg tcttgagtcc aacccggtaa    8100
gacacgactt atcgccactg gcagcagcca ctggtaacag gattagcaga gcgaggtatg    8160
taggcggtgc tacagagttc ttgaagtggt ggcctaacta cggctacact agaagaacag    8220
tatttggtat ctgcgctctg ctgaagccag ttaccttcgg aaaaagagtt ggtagctctt    8280
gatccggcaa acaaaccacc gctggtagcg gtggtttttt tgtttgcaag cagcagatta    8340
cgcgcagaaa aaaggatct caagaagatc ctttgatctt ttctacgggg tctgacgctc     8400
agtggaacga aaactcacgt taagggattt tggtcatgag attatcaaaa aggatcttca    8460
cctagatcct tttaaattaa aaatgaagtt ttaaatcaat ctaaagtata tatgagtaaa    8520
cttggtctga cagttaccaa tgcttaatca gtgaggcacc tatctcagcg atctgtctat    8580
ttcgttcatc catagttgcc tgactccccg tcgtgtagat aactacgata cgggagggct    8640
taccatctgg ccccagtgct gcaatgatac cgcgagaccc acgctcaccg gctccagatt    8700
tatcagcaat aaaccagcca gccggaaggg ccgagcgcag aagtggtcct gcaactttat    8760
ccgcctccat ccagtctatt aattgttgcc gggaagctag agtaagtagt tcgccagtta    8820
atagtttgcg caacgttgtt gccattgcta caggcatcgt ggtgtcacgc tcgtcgtttg    8880
gtatggcttc attcagctcc ggttcccaac gatcaaggcg agttacatga tcccccatgt    8940
tgtgcaaaaa agcggttagc tccttcggtc ctccgatcgt tgtcagaagt aagttggccg    9000
```

-continued

```
cagtgttatc actcatggtt atggcagcac tgcataattc tcttactgtc atgccatccg   9060
taagatgctt ttctgtgact ggtgagtact caaccaagtc attctgagaa tagtgtatgc   9120
ggcgaccgag ttgctcttgc ccggcgtcaa tacgggataa taccgcgcca catagcagaa   9180
ctttaaaagt gctcatcatt ggaaaacgtt cttcggggcg aaaactctca aggatcttac   9240
cgctgttgag atccagttcg atgtaaccca ctcgtgcacc caactgatct tcagcatctt   9300
ttactttcac cagcgtttct gggtgagcaa aaacaggaag gcaaaatgcc gcaaaaaagg   9360
gaataagggc gacacggaaa tgttgaatac tcatactctt cctttttcaa tattattgaa   9420
gcatttatca gggttattgt ctcatgagcg gatacatatt tgaatgtatt tagaaaaata   9480
aacaaatagg ggttccgcgc acatttcccc gaaaagtgcc acctgacgtc gacggatcgg   9540
gagatcaact tgtttattgc agcttataat ggttacaaat aaagcaatag catcacaaat   9600
ttcacaaata aagcattttt ttcactgcat tctagttgtg gtttgtccaa actcatcaat   9660
gtatcttatc atgtctggat caactggata actcaagcta accaaaatca tcccaaactt   9720 cccacccccat accctattac cactgccaat tacctgtggt ttcatttact ctaaacctgt   9780
gattcctctg aattattttc attttaaaga aattgtattt gttaaatatg tactacaaac   9840
ttagtagt                                                             9848

<210> SEQ ID NO 19
<211> LENGTH: 72
<212> TYPE: RNA
<213> ORGANISM: Artificial Sequence
<220> FEATURE:
<223> OTHER INFORMATION: pre-miR-451 structural mimic targeting eGFP

<400> SEQUENCE: 19
cuugggaaug gcaaggauga acuucagggu cagcuugcgc ugaccugaa guucauucuu    60 gcuauaccca ga                                                        72

<210> SEQ ID NO 20
<211> LENGTH: 72
<212> TYPE: RNA
<213> ORGANISM: Artificial Sequence
<220> FEATURE:
<223> OTHER INFORMATION: pre-miR-451 structural mimic targeting tetR

<400> SEQUENCE: 20
cuugggaaug gcaaggucuu gaucuuccaa uacgcaaccg uauuggaaga ucaagaucuu    60
gcuauaccca ga                                                        72

<210> SEQ ID NO 21
<211> LENGTH: 22
<212> TYPE: DNA
<213> ORGANISM: Artificial Sequence
<220> FEATURE:
<223> OTHER INFORMATION: eGFP primer

<400> SEQUENCE: 21
atgaacttca gggtcagctt gc                                              22

<210> SEQ ID NO 22
<211> LENGTH: 22
<212> TYPE: DNA
<213> ORGANISM: Artificial Sequence
<220> FEATURE:
<223> OTHER INFORMATION: TetR primer
```

```
<400> SEQUENCE: 22
tcttgatctt ccaatacgca ac                                              22

<210> SEQ ID NO 23
<211> LENGTH: 22
<212> TYPE: DNA
<213> ORGANISM: Artificial Sequence
<220> FEATURE:
<223> OTHER INFORMATION: SOD1 primer

<400> SEQUENCE: 23
ttcagtcagt cctttaatgc tt                                              22

<210> SEQ ID NO 24
<211> LENGTH: 22
<212> TYPE: DNA
<213> ORGANISM: Artificial Sequence
<220> FEATURE:
<223> OTHER INFORMATION: miR-16 primer

<400> SEQUENCE: 24
tagcagcacg taaatattgg cg                                              22

<210> SEQ ID NO 25
<211> LENGTH: 30
<212> TYPE: RNA
<213> ORGANISM: Artificial Sequence
<220> FEATURE:
<223> OTHER INFORMATION: pre-miR-451 mimic targeting GFP, Ago2 processed

<400> SEQUENCE: 25
augaacuuca ggducagcuu gcgcugaccc                                      30

<210> SEQ ID NO 26
<211> LENGTH: 42
<212> TYPE: RNA
<213> ORGANISM: Artificial Sequence
<220> FEATURE:
<223> OTHER INFORMATION: pre-miR-451 mimic targeting GFP, Drosha
      processed

<400> SEQUENCE: 26
augaacuuca gggucagcuu gcgcugaccc ugaaguucau uc                        42

<210> SEQ ID NO 27
<211> LENGTH: 22
<212> TYPE: RNA
<213> ORGANISM: Artificial Sequence
<220> FEATURE:
<223> OTHER INFORMATION: GFP siRNA targeting strand

<400> SEQUENCE: 27
augaacuuca gggucagcuu gc                                              22

<210> SEQ ID NO 28
<211> LENGTH: 22
<212> TYPE: RNA
<213> ORGANISM: Artificial Sequence
<220> FEATURE:
<223> OTHER INFORMATION: GFP siRNA targeting strand complement

<400> SEQUENCE: 28
aagcugaccc ugaaguucau uc                                              22
```

EXOSOME PACKAGING OF NUCLEIC ACIDS

RELATED APPLICATIONS

This application is a national stage filing under 35 U.S.C. § 371 of international PCT application, PCT/CA2016/051140, filed Sep. 30, 2016, which claims priority under 35 U.S.C. § 119(e) to U.S. Provisional Application, U.S. Ser. No. 62/236,057, filed on Oct. 1, 2015, each of which is incorporated herein by reference.

FIELD OF INVENTION

The present invention relates generally to exosomal packaging. More specifically, the present invention relates to methods and nucleic acid constructs for generating exosomes enriched with a nucleic acid of interest.

BACKGROUND

In 2006 the Nobel Prize in Medicine was awarded for the discovery of RNA interference (RNAi). Early research showed that RNAi triggers, such as small interfering RNAs (siRNAs), could be readily designed to silence virtually any gene in a specific and potent manner. This suggested that gene silencing nucleic acids such as siRNAs could be used to treat a wide variety of diseases. Discovery of the antisense oligonucleotide (AON) and RNA interference (RNAi) gene silencing pathways provided researchers with tools for silencing the expression of genes of interest. These pathways are both triggered by the introduction of small nucleic acid molecules into cells. These small nucleic acid molecules are typically designed to be at least partially complementary to the mRNA transcribed from the gene or genes of interest, and recognition/binding of the mRNA by the small nucleic acid molecules (i.e. the gene silencing nucleic acids) generally triggers degradation of the mRNA through either steric blocking/prevention of translation, or enzymatic degradation or cleavage of the mRNA.

Generally, RNA interference is a mechanism whereby approximately 21 nucleotide long double-stranded RNA molecules can potently silence or repress expression of specific genes having complementary mRNA sequence. Organisms from plants to worms and humans have endogenous RNA silencing systems wherein Argonaute (AGO) proteins bind small RNAs to silence gene expression. In humans, gene expression is reduced by cleaving and degrading RNA perfectly complementary to the gene silencing nucleic acid (i.e. siRNA guide strand), or repressing the translation of imperfectly complementary mRNA (such as in the case of miRNA gene silencing nucleic acids). In humans, the primary class of small RNA gene silencers are termed microRNAs (miRNA), which regulate large gene networks by repressing translation of mRNA with partially complementary binding sites (Fabian, 2010, Annu Rev Biochem, 79:351). miRNA are essential regulators of development, tumorigenesis and neurodegenerative disease (Penchcva, 2013, Nat Cell Biol, 15:546; Crocc, 2009, Nat Rev Genet, 10:704; Abe, 2013, Trends Cell Biol, 23:30). These critical roles of miRNAs have caused several companies to develop RNA-based drugs inhibiting or replacing miRNAs. For example, miRNA-based therapeutics in phase II clinical trials for hepatitis C have shown clear clinical benefit. Other miRNA therapeutics are in development for cancer, heart disease and inflammatory disorders like inflammatory bowel disease and arthritis, among others.

Perfectly complementary siRNAs elicit the enzymatic cleavage and degradation of target RNAs, eliciting a profound, rapid and specific silencing of a single gene. These perfectly complementary small RNAs, often called siRNAs or RNAi, are frequently used in research to study functions of specific genes, and are in development for therapeutic treatment of patients. For instance, in pre-clinical studies a single dose of siRNA can eliminate >80% of gene expression for six weeks in the liver with only minor off-target effects (Coelho, 2013, N Engl J Med, 369:819; Kanasty, 2013, Nature Materials, 12:967). The ability to almost completely eliminate expression of a specific gene with a single siRNA, or a select group of genes with a pool of siRNA, has enormous therapeutic potential for many diseases starting with those caused by viruses or genetically mutated proteins that cause pathology, such as in Huntington's disease and cancers. Near elimination of viral RNA, or cellular RNA before it produces disease-causing proteins, may represent a powerful therapeutic strategy for these diseases. RNAi may also be used to increase the efficacy of existing drugs by tailoring cellular responses or augmenting combinatorial effects on given pathways or physiological processes.

The strong potential of RNA silencing led to rapid development of several large RNAi therapeutic programs. Drug delivery of these therapeutics, however, has presented a significant challenge (Kanasty, 2013, Nature Materials, 12:967; Whitehead, 2009, Nat Rev Drug Discov, 8:129). Delivery to the liver now appears to be clinically robust. miRNA and RNAi/siRNA therapeutics targeted at the liver are in several phase 11 clinical trials. Challenges with delivery to other organs and cell types, however, has slowed the advancement of other promising small RNA therapeutics for cancer, heart disease, inflammatory and neurodegenerative diseases, among others (Kanasty, 2013, Nature Materials, 12:967; Whitehead, 2009, Nat Rev Drug Discov, 8:129).

Many strategies to deliver RNAi therapeutics have been tested, including lipid particles, siRNA-modifications, nanoparticles, and aptamers (Kanasty, 2013, Nature Materials, 12:967; Whitehead, 2009, Nat Rev Drug Discov, 8:129). Large, charged drugs readily permeate the liver due to its fenestrated endothelium. Efficient delivery to the liver has been achieved using advanced liposome technologies, such as Stable Nucleic Acid Lipid Particles (SNALP) and next-generation liposome technologies (Zimmerman, 2006, Nature, 441:111; Haussecker, 2012, Molecular Therapy Nucleic Acids, 1:e8). Liver delivery may also be achieved clinically with miRNA molecules chemically modified with GalNAc, or using complex polymers. Delivery to other tissues with similar approaches has been less successful, and has been a roadblock to bringing other RNAi therapeutics into clinical trials and therapeutic use (Coelho, 2013, N Engl J Med, 369:819; Kanasty, 2013, Nature Materials, 12:967; Haussecker, 2012, Molecular Therapy Nucleic Acids, 1:e8).

Recent research has demonstrated that an endogenous system which transports large molecules between cells may be appropriated as a drug delivery vehicle for certain therapeutics such as siRNA (Raposo, 2013, J Cell Biol, 200:373; Validi, 2007, Nat Cell Biol, 9:654). Extracellular vesicles called exosomes, which are tiny vesicles (40-120 nm), communicate molecules including RNA between cells, and a series of studies has demonstrated that if drugs, including RNAi therapeutics, can be packaged into exosomes, exosomes deliver them to multiple tissues including heart, liver, and lung, and even across the blood-brain barrier into neurons (Zhuang, 2011, Mol Ther, 19:1769; Alvarez-Erviti, 2011, Nat Biotechnology, 29:341). For example, exosomes delivered drugs like curcumin into the brain when injected intranasally in mice (Thery, 2006, Cur Protoc Cell Biol, Chapter 3, Unit 3 22). Exosomes injected intravenuously in the periphery may deliver RNAi therapeutics into the brain and achieve 60% reduction in expression of targets in the brain (Alvarez-Erviti, 2011, Nat Biotechnol, 29:341). These findings demonstrate the strong potential of exosomes as drug delivery vehicles for RNAi therapeutics and other drugs. Packaging of gene silencing nucleic acids into exosomes, however, remains a particularly difficult challenge.

Scaled-up production of GMP clinical grade exosomes has previously been studied (Lamparski, 2002, J Immunol Methods, 270:211). Exosomes have been investigated as potential cancer therapeutics, based initially on their potential ability to change antigen presentation and immune responses. However, attempts to maximize immunogenicity of exosomes resulted in only minimal effects on tumor responses in cancer patients in several clinical trials (Vlaud, 2011, J Immunother, 34:65). The evidence indicates that clinical grade exosomes may be manufactured, and that exosomes are generally non toxic and minimally immunogenic. The knowledge gained from the establishment of these processes may facilitate production of clinical-grade exosomes for drug delivery. Indeed, exosomes derived even from highly immunogenic dendritic cells had negligible effects on tumor responses in cancer patients in several clinical trials, so exosomes from other cell types may be minimally immunogenic when used for drug delivery. Evidence suggests that clinical use of suitable exosomes may be both feasible and safe as drug delivery vehicles.

Exosomes are 40-120 nm vesicles that have a subset of plasma membrane receptors on their surface and cytoplasmic contents in their interior. Exosomes are produced by budding of vesicles into the lumen of endosomes called multivesicular endosomes. Fusion of multivesicular endosomes with the plasma membrane releases the enclosed vesicles, exosomes, to the extracellular space (Colombo, 2014, Annu Rev Cell Dev Biol, 30:255). Due to this unique biogenesis process, exosomes contain a unique subset of plasma membrane receptors on their surface. Several properties of plasma membrane receptors that can cause their strong enrichment on exosomes have been uncovered. This knowledge can and has been used to engineer exosomes to target specific cells and tissues. Properties of receptors enriched on exosomes (e.g. myristolylation (Fang, 2007. PLoS Biol, 5:e158), C1C2 domains (Zeelenberg, 2008, Cancer Res, 68:1228), LAMP2 cytoplasmic domain (Alvarez-Erviti, 2011, Nat Biotechnol, 29:341) may be used to engineer the enrichment of new receptors on the exosome surface to target specific tissues like brain or breast cancer (Alvarez-Erviti, 2011, Nat Biotechnol. 29:341; Ohno, 2013, Mol Ther, 21:185). Indeed, specific domains (e.g. C1C2, LAMP2 cytoplasmic domain) may be attached onto plasma membrane receptors, that cause them to be selectively sorted onto exosomes. As such, two of the major hurdles to using exosomes as drug delivery vehicles (mass production and tissue-specific targeting) may addressable in such a manner.

However, perhaps the major remaining roadblock to using exosomes or exosome-like vesicles as drug delivery vehicles for therapeutic nucleic acids such as gene silencing nucleic acids may be the ability to package siRNA/RNAi/miRNA, or other nucleic acids of interest, into exosomes. Exosomes have a highly selective content of both proteins and RNA as compared to the cells that produce them. For example, some miRNAs are virtually undetectable in cells and abundant in exosomes. Unfortunately, the opposite is frequently true, where a cellular miRNA is undetectable in exosomes produced therefrom. Therefore, a technical strategy for packaging desired nucleic acid sequences, such as gene silencing nucleic acids, into exosomes, as well as their enrichment within exosomes, is desirable.

Several attempts have been made to identify strategies to enrich miRNA or other RNAs in exosomes. Searches for sequence motifs that cause enrichment of RNAs in exosomes have had mixed results. Initial searches turned up several putative short motifs but the ability of these motifs to cause sorting of RNA into exosomes was not tested (Batagov, 2011, BMC Genomics, 12(3):S8; Villarroya-Beltri, 2013, Nat Commun, 4:2980). A recent article suggests that a hexanucleotide motif in miRNAs can promote their enrichment 2-5-fold in exosomes (Villarroya-Beltri, 2013, Nat Commun, 4:2980). Whether this relatively modest effect is maintained in other cell types was not tested. This is particularly important because emerging evidence suggests that exosomes produced by distinct cell types, such as those most adapted for production of clinical grade exosomes, may not consistently share biogenesis mechanisms and other properties. Some studies have used electroporation or related methods to putatively introduce RNAi therapeutics into exosomes (Alvarez-Erviti et al., Nat Biotechnol, 29:341 (2011)). Many doubts were raised about the ability to consistently generate holes of 5-10 nm (RNAi therapeutics~5 nm) in the membrane of vesicles with a diameter of 100 nm in a manner that would retain consistent exosome function in mass production for clinical use. Indeed, subsequent investigation demonstrated that the majority of RNAi therapeutics precipitated when electroporated using identical techniques (Kooijmans, 2013. J Control Release, 172:229). This suggests that physical introduction of RNAi therapeutics into exosomes is unlikely to generate a consistent, pure exosome product. To date, there has been no widely applicable and robust mechanism for packaging nucleic acids of interest within exosomes described.

An alternative, additional, and/or improved method for packaging nucleic acids of interest in exosomes, and/or for delivering nucleic acids of interest to cells is desirable.

SUMMARY OF INVENTION

In an embodiment, there is provided herein a method for producing exosomes or exosome-like vesicles comprising a gene silencing nucleic acid, a nucleic acid of interest, or a precursor thereof, said method comprising:

introducing into an exosome-producing cell, or expressing in an exosome-producing cell, a nucleic acid construct comprising the gene silencing nucleic acid, nucleic acid of interest, or a precursor thereof, incorporated within a pre-miR-451 structural mimic; and producing exosomes or exosome-like vesicles from the cell.

In another embodiment of the method above, the method may further comprise an optional step of collecting or enriching the produced exosomes or exosome-like vesicles.

In still another embodiment of the above method or methods, the pre-miR-451 structural mimic may comprise a stem-loop secondary structure.

In yet another embodiment of the above method or methods, the pre-miR-451 structural mimic may comprise a stem-loop secondary structure having a blunt end, a 5' overhang, a 3' overhang, or 5' and 3' loose ends.

In yet another embodiment of the above method or methods, the pre-miR-451 structural mimic may comprise a stem-loop secondary structure having an overall length of about 25-54 nucleotides (nt).

In still another embodiment of the above method or methods, the pre-miR-451 structural mimic may comprise a stem-loop secondary structure having an overall length of about 40, 41, 42, 43, 44, 45, 46, 47, 48, 49, 50, 51, or 52 nucleotides (nt).

In still another embodiment of the above method or methods, the pre-miR-451 structural mimic may comprise a stem-loop secondary structure having an overall loop length of about 4, 5, 6, 7, or 8 nt.

In yet another embodiment of the above method or methods, the pre-miR-451 structural mimic may comprise a stem-loop secondary structure having at least one base pair mismatch in the stem.

In still another embodiment of the above method or methods, the pre-miR-451 structural mimic may comprise a stem-loop secondary structure having at least one base pair mismatch in the stem positioned within the first three base pairs adjacent a Drosha cleavage site.

In another embodiment of the above method or methods, the pre-miR-451 structural mimic may comprise a stem-loop secondary structure with a 3' end which extends to, or before, or after an Ago2 cleavage position, such that the pre-miR-451 structural mimic includes a 5' overhang portion and a 3' base-paired portion. By way of example, in certain embodiments, the pre-miR-451 structural mimic may comprise a stem-loop secondary structure with a 5' overhang portion and a 3' base-paired (or substantially base-paired, or partially base-paired) portion which is shortened from full-length, and may fall at or between full length minus one (−1) nucleotide and mature lengths.

In yet another embodiment of the above method or methods, the pre-miR-451 structural mimic may comprise a single-stranded structure including a 3' portion, which is optionally loop-derived sequence, mimicking mature miR-451. In certain further embodiments, the pre-miR-451 structural mimic may be about 22-35 nt in length. In certain further embodiments, the pre-miR-451 structural mimic may be about 23-24 nt in length.

In another embodiment of the method or methods above, the cell may be a cell which naturally produces exosomes enriched with miR-451.

In yet another embodiment of the above method or methods, the cell may be a primary human mesenchymal stem cell, a primary mouse macrophage, a human breast cancer cell line such as MDA-MB-231, a mouse or human neuronal cell line such as Neuro2a or SHSY, a mouse astrocytec cell line such as C8 Da or SIM, a mouse microglia cell line such as BV2, a mouse motor neuron cell line such as NSC-34 or MN-1, a HeLa, mouse embryonic fibroblast, or a mouse dendritic cell such as JAWS II. In certain embodiments, the cell may be an MEF or JAWSII cell.

In an embodiment of the above method or methods, the gene silencing nucleic acid may be a gene silencing nucleic acid which is not mature miR-451.

In a further embodiment of any method as described above, the cell may be an embryonic stem cell (ESC) clone H1 or H9 cell, a mesenchymal stem cell (MSC), or a cell having low Ago2 expression or activity levels. By way of example, a cell having low Ago2 expression or activity levels may include melanoma cell lines, HepG2 cell lines, MCF-7 cell lines, a cell treated with lenalidomide, or derived cells with genetic deletions of Ago2 using technologies such as Crispr, TALEN zinc fingers, or other methods known to the skilled person. In certain embodiments, the cell may be an Ago2 knockout cell.

In still a further embodiment of any method as described above, the cell may be an embryonic stem cell (ESC) clone H9 cell.

In yet another embodiment of any method as described above, the gene silencing nucleic acid may be, may be a precursor of, or may be derived from, a miRNA, shRNA, Crispr Guide RNA, or an siRNA.

In a further embodiment of any method as described above, the cell may be cultured in serum-free media, or in the absence of serum, or in a scrum specifically treated to eliminate or remove exosomes and/or exosome-like vesicles from it (i.e., an exosome-depleted serum media), while producing the exosomes or exosome-like vesicles.

In yet another embodiment of any method as described above, the method may further comprise purifying or concentrating exosomes produced by the cell.

In still another embodiment of any method as described above, the exosomes or exosome-like vesicles may be purified or concentrated from serum-free media, or from serum media which has been previously treated or processed to remove or reduce exosomal content and/or exosome-like vesicle content (i.e. exosome-depleted serum media).

In yet another embodiment of any of the method or methods above, the method may further comprise a step of treating the exosome-producing cell with a lysosomal or autophagy inhibitor. By way of non-limiting example, such inhibitors may include bafilomycin A1, concanamycin, or chloroquine, for example.

In still another embodiment of any of the method or methods above, the method may further comprise a step of inhibiting expression or activity of Ago2 in the exosome-producing cell. In certain embodiments, Ago2 may be inhibited using, for example, a gene silencing nucleic acid such as but not limiting to an siRNA, miRNA, shRNA, or antisence oligonucleotide. In certain embodiments. Ago2 may be inhibited using BCI-137 or another suitable Ago2 inhibitor, for example.

In another embodiment, there is provided herein a composition comprising:
  an exosome or an exosome-like vesicle; and
  a nucleic acid construct comprising a gene silencing nucleic acid incorporated in a pre-miR-451 structural mimic, or a precursor or cleavage fragment (such as, but not limited to, an enzymatic cleavage fragment) thereof;
  wherein the nucleic acid construct, or precursor or enzymatic cleavage fragment thereof, is within the exosome or exosome-like vesicle, on the exterior of the exosome or exosome-like vesicle, or a combination thereof.

In an embodiment of a composition as described above, the gene silencing nucleic acid may be a gene silencing nucleic acid which is not mature miR-451.

In a further embodiment of any composition as described above, the composition may further comprise one or more exosome-producing cells.

In still another embodiment of any composition as described above, the composition may further comprise a serum-free medium which does not contain exosomes and/or exosome-like vesicles, or a serum medium which has been previously treated or processed to remove or reduce exosomal content and/or exosome-like vesicle content, such as an exosome-depleted serum media.

In yet another embodiment of any of the composition or compositions above, the composition may further comprise at least one of a lysosomal inhibitor, an autophagy inhibitor, or an inhibitor of Ago2 expression or activity.

In another embodiment, them is provided herein a use of a nucleic acid construct comprising a gene silencing nucleic acid incorporated within a pre-miR-451 structural mimic for packaging said gene silencing nucleic acid into an exosome or an exosome-like vesicle produced by an exosome-producing cell, wherein the nucleic acid construct is for introduction into, or expression in, said cell.

In still another embodiment of the above use, the pre-miR-451 structural mimic may comprise a stem-loop secondary structure.

In yet another embodiment of the above use or uses, the pre-miR-451 structural mimic may comprise a stem-loop secondary structure having an overall length of about 25-52 nucleotides (nt).

In still another embodiment of the above use or uses, the pre-miR-451 structural mimic may comprise a stem-loop secondary structure having an overall length of about 40, 41, 42, 43, 44, 45, 46, 47, 48, 49, 50, 51, or 52 nucleotides (nt).

In yet another embodiment of the above use or uses, the pre-miR-451 structural mimic may comprise a stem-loop secondary structure having an overall loop length of about 4, 5, 6, 7, or 8 nt.

In still another embodiment of the above use or uses, the pre-miR-451 structural mimic may comprise a stem-loop secondary structure having at least one base pair mismatch in the stem.

In yet another embodiment of the above use or uses, the pre-miR-451 structural mimic may comprise a stem-loop secondary structure having at least one base pair mismatch positioned within the first three base pairs adjacent a Drosha cleavage site.

In yet another embodiment of the above use or uses, the pre-miR-451 structural mimic may comprise a stem-loop secondary structure with a 3' end which extends to, or before, or after an Ago2 cleavage position, such that the pre-miR-451 structural mimic includes a 5' overhang portion and a 3' base-paired portion.

In another embodiment of the above use or uses, the pre-miR-451 structural mimic may comprise a single-stranded structure including a 3' portion, which is optionally loop-derived sequence, mimicking mature miR-451. In certain embodiments, the pre-miR-451 structural mimic may be about 22-35 nt in length, or may be 22 nt in length, 35 nt in length, or any individual integer value therebetween. In certain embodiments, the pre-miR-451 structural mimic may be about 23-24 nt in length.

In another embodiment of the above use or uses, the cell may be a cell which naturally produces exosomes enriched with miR-451.

In still another embodiment of the above use or uses, the cell may be a primary human mesenchymal stem cell, a primary mouse macrophage, a human breast cancer cell line such as MDA-MB-231, a mouse or human neuronal cell line such as Neuro2a or SHSY, a mouse astrocyte cell line such as C8 Da or SIM, a mouse microglia cell line such as BV2, a mouse motor neuron cell line such as NSC-34 or MN-1, a HeLa, mouse embryonic fibroblast, or a mouse dendritic cell such as JAWS II. In certain embodiments, the cell may be an MEF or JAWSII cell.

In an embodiment of any use as described above, the gene silencing nucleic acid may be a gene silencing nucleic acid which is not mature miR-451.

In a further embodiment of any use as described above, the cell may be an embryonic stem cell (ESC) clone H1 or H9 cell, a mesenchymal stem cell (MSC), or a cell having low Ago2 expression or activity levels.

In still a further embodiment of any use as described above, the cell may be an embryonic stem cell (ESC) clone H9 cell.

In yet another embodiment of any use as described above, the gene silencing nucleic acid may be, or may be derived from, a miRNA, shRNA. CRISPR guide RNA, or siRNA.

In a further embodiment of any use as described above, the cell may be cultured in serum-free media, or in a serum media which has been previously treated or processed to remove or reduce exosomal content and/or exosome-like vesicle content (i.e. an exosome-depleted serum media).

In still another embodiment of any of the use or uses above, the nucleic acid construct may be for use in combination with at least one of a lysosomal inhibitor, an autophagy inhibitor, or an inhibitor of Ago2 expression or activity.

In another embodiment, there is provided herein a nucleic acid construct comprising a gene silencing nucleic acid incorporated within a pre-miR-451 structural mimic.

In a further embodiment of a nucleic acid construct as described above, the nucleic acid construct may be for packaging the gene silencing nucleic acid, or a precursor thereof, into an exosome or an exosome-like vesicle produced by an exosome-producing cell, wherein the nucleic acid construct is for introduction into, or expression in, the cell.

In a further embodiment of any nucleic acid construct as described above, the gene silencing nucleic acid may be a gene silencing nucleic acid which is not mature miR-451.

In another embodiment, there is provided herein a method for preparing exosomes or exosome-like vesicles enriched with a nucleic acid sequence of interest, or a precursor thereof, said method comprising:
  introducing into an exosome-producing cell, or expressing in an exosome-producing cell, a nucleic acid construct comprising the nucleic acid sequence of interest incorporated within a pre-miR-451 structural mimic; and
  allowing the cell to produce exosomes or exosome-like vesicles.

In another embodiment of the above method, the method may further comprise an optional step of collecting or enriching the produced exosomes or exosome-like vesicles.

In yet another embodiment of the above method or methods, the gene silencing nucleic acid may be a gene silencing nucleic acid which is not mature miR-451.

In an embodiment, there is provided herein a nucleic acid delivery composition comprising:
  an exosome or an exosome-like vesicle; and
  a nucleic acid construct comprising a gene silencing nucleic acid incorporated in a pre-miR-451 structural mimic, or a precursor or cleavage fragment thereof;
  wherein the nucleic acid construct, or a precursor or cleavage fragment thereof, is contained or packaged within the exosome or the exosome-like vesicle, carried on the exterior of the exosome or the exosome-like vesicle, or a combination thereof.

In an embodiment of a nucleic acid delivery composition as described above, the gene silencing nucleic acid may be a gene silencing nucleic acid which is not mature miR-451.

In a further embodiment of a nucleic acid delivery composition as described above, the exosome or exosome-like vesicle may be produced by an embryonic stem cell (ESC) clone H1 or H9 cell, or a mesenchymal stem cell (MSC), or another cell as described herein.

In still another embodiment of a nucleic acid delivery composition as described above, the exosome or exosome-like vesicle may be produced by cells cultured in serum-free media, or in serum media which has been previously treated or processed to remove or reduce exosomal content and/or exosome-like vesicle content (i.e. an exosome-depleted serum media).

In another embodiment, there is provided herein a use of a nucleic acid delivery composition as described above for silencing the cellular expression of a gene targeted by the gene silencing nucleic acid.

In another embodiment, there is provided herein a method for identifying whether a candidate exosome-producing cell is an exosome-producing cell which is suitable for producing enriched exosomes or exosome-like vesicles using a nucleic acid construct comprising a gene silencing nucleic acid, nucleic acid of interest, or a precursor thereof, incorporated within a pre-miR-451 structural mimic, said method comprising:

quantitating miR-451 content of exosomes produced by said candidate exosome-producing cell and determining whether miR-451 is exosomally enriched;

wherein exosomal enrichment of miR-451 indicates that the candidate exosome-producing cell is suitable for producing the enriched exosomes or exosome-like vesicles.

In yet another embodiment of the above method, exosomal enrichment of miR-451 may be determined by comparing miR-451 exosomal levels with exosomal levels of a reference endogenously expressed miRNA which is not miR-451.

In still another embodiment of the above method, the reference endogenously expressed miRNA may be miR-16 or let-7a, or a combination thereof.

In another embodiment of any of the above method or methods for producing exosomes, the method may further comprise a step of treating the exosome-producing cell with a lysosomal or autophagy inhibitor.

In still another embodiment of any of the above method or methods for producing exosomes, the method may further comprise a step of inhibiting expression or activity of Ago2 in the exosome-producing cell. In certain embodiments, Ago2 may be inhibited using an siRNA, antisense oligonucleotide, or other gene silencing nucleic acid.

It will be appreciated that embodiments are provided for illustrative purposes intended for those skilled in the art, and are not meant to be limiting in any way.

BRIEF DESCRIPTION OF DRAWINGS

FIG. 13 provides nucleic acid sequences of select nucleic acids described herein.

Figure 1:
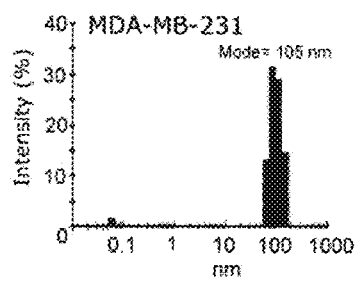
FIG. 1 shows a demonstration of exosome enrichment from media of MDA-MB-231 (breast cancer epithelial line) or mouse embryonic fibroblast (MEF). (A) Dynamic light scattering analysis of size (x-axis) of exosome preparations from MDA-MB-231 and MEF cells. (B) Nanosight particle tracking analysis of the size of vesicles in exosome preparations from MDA-MB-231 and MEF cells. (C) Western blot analysis of equivalent amounts (µg protein) of total cell lysate and exosome preparations from MDA-MB-231 and MEF cells for exosome markers (Flottilin2, Tsg101, Alix), markers of other compartments (Tom20, mitochondria). (D) Representative electron microscopy images of exosome preparations from MDA-MB-231 and MEF cells.
Figure 1:
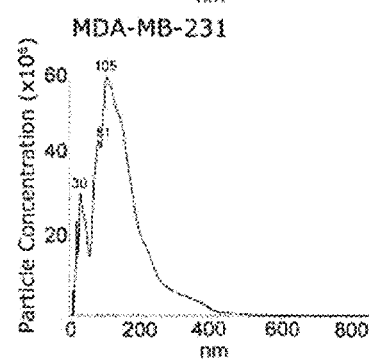
Figure 1:
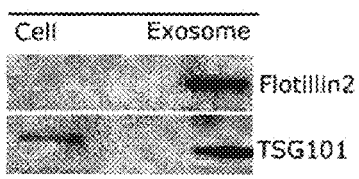
Figure 1:
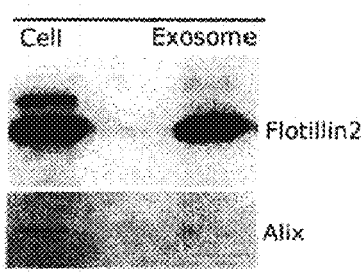
Figure 1:
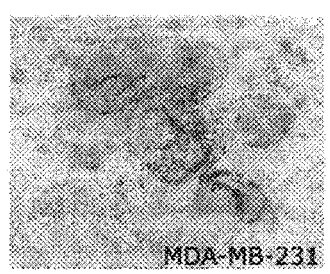
Figure 1:
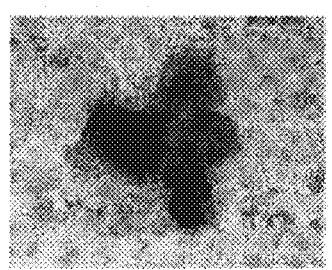

It will be appreciated that the above Figures are provided for illustrative purposes intended for those skilled in the art, and are not meant to be limiting in any way.

DETAILED DESCRIPTION

Described herein are compounds, compositions, nucleic acid constructs, nucleic acid backbones, tags, nucleic acid structural mimics, and methods for packaging nucleic acids of interest, such as (but not limited to) gene silencing nucleic acids, into exosomes. By way of non-limiting example, the present invention provides methods for packaging gene silencing nucleic acids (for example, but not limited to, siRNA, miRNA, shRNA, and others) into exosomes for use as a delivery vehicle, nucleic acid-packaged exosomes, and compositions comprising said packaged exosomes. In certain embodiments, a nucleic acid construct is provided which may be used to effect packaging of a nucleic acid of interest within an exosome by incorporating the nucleic acid of interest into said nucleic acid construct.

It will be appreciated that embodiments and examples are provided for illustrative purposes intended for those skilled in the art, and are not meant to be limiting in any way.

In certain embodiments, there is provided herein a method for producing or preparing exosomes enriched with, or comprising, a gene silencing nucleic acid, a nucleic acid of interest, or a precursor thereof, said method comprising:
  introducing into an exosome-producing cell, or expressing in an exosome-producing cell, a nucleic acid construct comprising the gene silencing nucleic acid, nucleic acid of interest, or a precursor thereof, incorporated within a pre-miR-451 structural mimic; and
  producing exosomes from the cell.

In certain embodiments, the above method may, optionally, include a further step of collecting or enriching the produced exosomes or exosome-like vesicles. As will be understood, exosomes or exosome-like vesicles may be purified by any of several suitable methods known to those skilled in the art having regard to the teachings provided herein. For example, exosomes may be purified by differential centrifugation in which cells and larger vesicles or debris are eliminated in preliminary centrifugation steps of up to 10 to 20 000 g, and exosomes may be subsequently enriched from the resulting supernatant by centrifugation at or above 70 000 g for 1 h in a SW28 or SW32 rotor (or an equivalent in other rotor types). Exosomes may also be purified by precipitation using reagents such as Systems Biosciences Exoquick, Exiqon miRCURY exosome isolation kit, or Total exosome isolation kit from Thermofisher, or similar techniques. Exosomes may also be enriched using size based filtration using vacuum pumps, tangential flow filtration, or centrifugal filtration. In such methods cells and larger vesicles or debris may be eliminated by filtering through a filter with pores larger than 100 nm and typically of 0.22 um. Exosomes may then be concentrated using filters with pores smaller than 100 nm by tangential flow filtration or other filtering methods. Exosomes may also be purified by affinity purification. In such methods, antibodies or other ligands which bind to exosomes may be coupled to beads or other fixed supports to allow capture, purification and concentration of exosomes from liquids. The person of skill in the art having regard to the teachings herein will be able to select a suitable collection or enriching technique suitable for a particular application.

It will be understood that, in certain embodiments, a nucleic acid construct may refer to any suitable RNA-based (or partially RNA-based) nucleic acid sequence, or a suitable DNA-modified and/or chemically-modified analogue thereof, which comprises a gene silencing nucleic acid, a nucleic acid of interest, or a precursor thereof, which is incorporated within a pre-miR-451 structural mimic sequence such that at least a portion of the nucleic acid construct adopts a secondary structure which includes the gene silencing nucleic acid/nucleic acid of interest/precursor thereof and substantially structurally mimics that of pre-miR-451. It will be understood that, in certain non-limiting embodiments, a nucleic acid construct as described herein may structurally resemble pre-miR-451, or pri-miR-451, secondary structure. In further non-limiting embodiments, suitable nucleic acid constructs may include nucleic acid constructs which are precursors of a nucleic acid which structurally mimics pre-miR-451 secondary structure (i.e. a nucleic acid which may be enzymatically processed to produce a pre-miR-451 secondary structure mimic).

A secondary structure predicted to be adopted by pre-miR-451 is a stem-loop structure as follows:

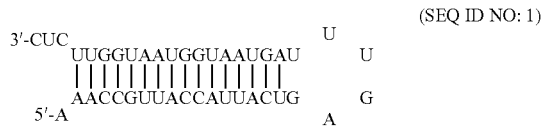

(SEQ ID NO: 1)

This predicted secondary structure is provided for non-limiting, illustrative purposes. It will be understood that other, similar, secondary structures may be possible. By way of non-limiting example, Yang and Lai, R N A, 2012, predict a 2-nt loop (Yang. Maurin, Lai, RNA, 18, 945, 2012), whereas Cifuentes et al., Science, 2010 predict a 4 nt loop section. Each of these references are herein incorporated by reference in their entirety.

Ohno et al., Development of Novel Small Hairpin RNAs that do not Require Processing by Dicer or Ago2, Molecular Therapy, doi:10.1038/mt.2016.81, herein incorporated by reference in its entirety, further describes modifications of pre-miR-451 structure which allow processing into miRNA, and describes shortening of the stem to about 14-15 nt while keeping the loop, with the miR-451 processing pathway still functional.

A pre-miR-451 structural mimic may be any suitable nucleic acid which comprises a sequence which adopts a secondary structure which is substantially structurally and/or functionally similar to that of pre-miR-451 as shown above or as described in further detail herein. In certain embodiments, a pre-miR-451 structural mimic may be a nucleic acid which comprises a stem-loop structure having a 12-21 nt long stem, and a 2-12 nt long loop. In an embodiment, the stem-loop may include any individual combination of a 12, 13, 14, 15, 16, 17, 18, 19, 20, or 21 nt in length stem, and a 2, 3, 4, 5, 6, 7, 8, 9, 10, 11, or 12 nt in length loop. It is not necessary that the pre-miR-451 structural mimic include any of the pre-miR-451 primary sequence, although this may be possible in non-limiting embodiments.

In certain embodiments, a pre-miR-451 structural mimic may comprise a stem-loop secondary structure. In certain further embodiments, the stem-loop secondary structure may have a blunt end, a 5' overhang, a 3' overhang, or 5' and 3' loose ends, for example. In certain non-limiting embodiments, an overhang may be an extension of one arm of the stem loop over the other. In certain non-limiting embodiments, an overhang may be up to about 3 nt in length, for example.

In certain embodiments, a pre-miR-451 structural mimic may comprise a stem-loop secondary structure having an overall length of about 25-54 nucleotides (nt). In certain embodiments, the stem-loop secondary structure may have an overall length of about 40, 41, 42, 43, 44, 45, 46, 47, 48, 49, 50, 51, or 52 nucleotides (nt). In certain embodiments, a pre-miR-451 structural mimic may comprise a stem-loop secondary structure having an overall loop length of about 4, 5, 6, 7, or 8 nucleotides. In certain embodiments, a pre-miR-451 structural mimic may comprise a stem-loop secondary structure having one or more base pair mismatch(es) in the stem. In certain embodiments, a pre-miR-451 structural mimic may comprise a stem loop secondary structure having one or more base pair mismatch(es) positioned within the first 3 base pairs adjacent a pre-miR-451 Drosha cleavage site.

As will be further discussed below, in certain embodiments, the stem-loop structure of the pre-miR-451 structural mimic sequence may comprise the gene silencing nucleic acid/nucleic acid of interestiprecursor thereof, or at least a substantial portion thereof, or a suitable nucleic acid sequence derived therefrom. By way of non-limiting example, an siRNA may be incorporated within a pre-miR-451 structural mimic as follows: the 5' stem portion of the pre-miR-451 structural mimic (and, optionally, at least a part of the loop region and/or part of the 3' stem) may be replaced by a guide strand from, or derived from, an siRNA and, to remain a structural mimic of pre-miR-451, the 3' stem portion of the pre-miR-451 structural mimic may accordingly be replaced by a sequence which is at least substantially a reverse complement of the 5' stem portion, resulting in a pre-miR-451 structural mimic into which a gene silencing nucleic acid has been incorporated. Although the primary sequence of the pre-miR-451 structural mimic may not resemble that of pre-miR-451, the secondary structure of the pre-miR-451 maintains a stem-loop structure as described above.

In certain non-limiting embodiments, a suitable nucleic acid construct may have a sequence length of about 40-65 nt (approximately corresponding to the length of pre-miR-451, depending on the variant made) or a sequence length up to 300 nt or greater (approximately corresponding to the length of pri-miR-451). These nucleic acid constructs, or cleavage fragments thereof (such as, but not limited to, enzymatic cleavage fragments of 18-35 nt in length), may be packaged in exosomes and, in certain embodiments involving, for example, siRNA/miRNA packaging, processed into mature siRNA/miRNA prior to, during, or following packaging in the exosome, or afterwards in the target cell.

In additional non-limiting embodiments, examples of nucleic acids which may be incorporated within a pre-miR-451 structural mimic may include those having a length of about 12-32 nt, such as a nucleic acid of 12, 13, 14, 15, 16, 17, 18, 19, 20, 21, 22, 23, 24, 25, 26, 27, 28, 29, 30, 31, or 32 nt in length.

In addition to the nucleic acids of interest described above and below, nucleic acids of interest may, in certain embodiments, further include activating RNAs (e.g. promoter-associated), RNAs affecting splicing, RNAs affecting epigenetic states, or other suitable RNAs, DNAs, or chemically modified nucleic acids of interest having a length of about 12-32 nt which can be accommodated within a pre-miR-451 structural mimic.

It will be understood that a pre-miR-451 structural mimic as described herein may have significant sequence variation from that of endogenous pre-miR-451, so long as the pre-miR-451 stem-loop secondary structure is substantially retained and/or so long as the pre-miR-451 function is substantially retained. By way of non-limiting example, a suitable structural mimic pre-miR-451 may comprise a stem-loop sequence having a length similar to that of pre-miR-451, and a stem-loop type structure similar to that of the pre-miR-451 backbone, wherein the stem is about 12-21 nt long and the loop is about 4-12 nt long. In certain non-limiting examples, a smaller loop may be possible, such as a 2-3 nt loop.

Pre-miR-451 structural mimics may also include nucleic acids which structurally mimic pre-miR-451 mutants and variants which substantially retain endogenous properties/functions of pre-miR-451, such as enzymatic cleavage profile and/or exosomal packaging characteristics. Examples of suitable pre-miR-451 mimics may include, for example, suitable pre-miR-451 structural mimics as described in U.S. Pat. No. 8,273,871, which is herein incorporated by reference in its entirety.

Pre-miR-451 structural mimics may also include, in certain non-limiting embodiments, nucleic acids which structurally or functionally mimic pre-miR-451, or pre-miR-451 precursors, or partially processed intermediates of pre-miR-451. In certain embodiments, pre-miR-451 structural mimics may include mimics of nucleic acids resulting from downstream pre-miR-451 processing including Drosha cleavage, Ago2 cleavage, and/or 3' exonuclease cleavage products.

In certain embodiments a pre-miR-451 structural mimic may comprise a stem-loop secondary structure with a 3' end which extends to or before an Ago2 cleavage position, such that the pre-miR-451 structural mimic includes a 5' overhang portion and a 3' base-paired portion.

In certain other embodiments, a pre-miR-451 structural mimic may comprise a single-stranded structure including a 3' portion, which is optionally loop-derived sequence, mimicking mature miR-451. By way of example, such a pre-miR-451 structural mimic may comprise a single-stranded nucleic acid of about 22-35 nt in length, such as a single-stranded nucleic acid of about 23-24 nt in length.

It will be understood that, in certain non-limiting embodiments, a pre-miR-451 mimic may be any suitable nucleic acid sequence having a sequence/structure which mimics a miR-451 precursor. By way of non-limiting example, a pre-miR-451 mimic may be a nucleic acid sequence which is processed in a Dicer-independent, AGO-2 dependent manner similar to that of pre-miR-451 and/or which retains endogenous properties/functions of pre-miR-451 such as exosomal packaging characteristics. In a non-limiting embodiment, a pre-miR-451 structural mimic having a nucleic acid of interest, such as a gene silencing nucleic acid, incorporated therein, may be any suitable nucleic acid sequence which is processed in a Dicer-independent, AGO-2 dependent manner similar to that of pre-miR-451 so as to produce the nucleic acid of interest or a precursor thereof. In certain embodiments, non-limiting examples of suitable pre-miR-451 structural mimics may include those having suitable sequence and/or structural changes or variations which are tolerated by AGO2 and do not impair pre-miR-451-type enzymatic processing.

Not all cell types produce/release exosomes. As will also be understood, an exosome-producing cell may refer to any cell which produces/releases exosomes or exosome-like vesicles. In certain embodiments, an exosome-producing cell may be an exosome-producing cell which is naturally enriched in miR-451, or pre-miR-451, as compared to other exosome-producing cells, or exosome-producing cells in which Ago2 is deficient as compared to other exosome-producing cells. In further embodiments, exosome-producing cells may be cells which naturally produce exosomes or exosome-like vesicles enriched in endogenous miR-451, such as but not limited to human embryonic stem cell H9 or H1 cells, mesenchymal stem cells, primary dendritic cells, MDA-MB-231 cells, plasma cells (Cheng, 2014, Journal of extracellular vesicles, 3), serum cells (Cheng, 2014, Journal of extracellular vesicles, 3), mast cells (Valadi, 2007, Nat Cell Biol, 9:654), glioblastoma cells, B cells, cardiac progenitor cells, or MSC cells (Collino, 2010, PLos One, 5:e11803). In still further embodiments, an exosome-producing cell may be, but is not limited to, an embryonic stem cell, a mesenchymal stem cell, or any differentiated version of the two former stem cells, a dendritic cell, a macrophage, a monocyte, a T or B cell, a fibroblast, or a cell line such as but not limited to a HeLa, 2931, or MDA-MB-231 cell line.

In certain embodiments, an exosome-producing cell may be a cell which naturally produces exosomes enriched with miR-451. In certain further embodiments, the cell may be a primary human mesenchymal stem cell, a primary mouse macrophage, a human breast cancer cell line such as MDA-MB-231, a mouse or human neuronal cell line such as Neuro2a or SHSY, a mouse astrocyte cell line such as C8 Da or SIM, a mouse microglia cell line such as BV2, a mouse motor neuron cell line such as NSC-34 or MN-1, a HeLa, mouse embryonic fibroblast, or a mouse dendritic cell such as JAWS II. By way of example, the cell may be an MEF or JAWSII cell.

The further embodiments, an exosome-producing cell may be an embryonic stem cell (ESC) clone H1 or H9 cell, a mesenchymal stem cell (MSC), or a cell having low Ago2 expression or activity levels, or a cell in which Ago2 is knocked out or stably silenced. By way of example, a cell having low Ago2 expression or activity levels may include melanoma cell lines, HepG2 cell lines, MCF-7 cell lines, a cell treated with lenalidomide, or derived cells with genetic deletions of Ago2 using technologies such as Crispr, TALEN zinc fingers, or other methods known to the skilled person. Further discussion of cells having low Ago2 expression or activity levels may be found in Voller et al., Argonaute Family Protein Expression in Normal Tissue and Cancer Entities, PLOS One, 2016, 11(8):e0161165; and Xu et al., Expression of cereblon binding protein argonaute 2 plays an important role for multiple mycloma cell growth and survival, BMC Cancer, 2016, 16:297, each of which are herein incorporated by reference in their entirety.

In certain embodiments, Ago2 may be inhibited using, for example, BCI-137, or another suitable Ago2 inhibitor (further described in, for example, Masciarelli et al., A small-molecule targeting the microRNA binding domain of Argonaute 2 improves the retinoic acid differentiation response of the acute promyelocytic leukemia cell line NB4, ACS Chemical Biology, 2014, 9(8), 1674-1679; and Schmidt et al., MicroRNA-specific argonaute 2 protein inhibitors, ACS Chem Bio, 2013, 8(10), 2122-2126; and Xia et al., Small-molecule regulators of microRNAs in Biomedicine, Drug Development Research, 2015, 76(7), 375-381; each of which are herein incorporated by reference in their entirety).

It will be understood that, in certain non-limiting embodiments, it may be possible to use gene silencing agents such as siRNAs, or gene expression vectors, to improve the characteristics of the exosome-producing cells, or the exosomes produced by exosome producing cells. By way of non-limiting example, it may be possible to use siRNA agents to increase cellular exosome production, or to shape characteristics of the exosome-producing cells or the exosomes produced therefrom to, for example, reduce immunogenicity, oncogenicity, toxic, or otherwise undesirable properties. In certain non-limiting embodiments, it may be possible to use transcripts including pri-miR-144 and pri-miR-451 (or structural mimics thereof as described herein), wherein an alternative siRNA affecting cellular or exosomal characteristics is inserted into the pri-miR-144 sequence.

Examples of exosome-producing cells, in approximate order of exosome production from least to most in standard cell culture conditions, may include (but are not limited to):
  glioblastoma cell line U251-MG;
  epithelial and fibroblast cells like HeLa, MDA-MB-231, and HCT-116 cells (produce moderate amounts of exosomes); and
  neurons, immune and blood cells (including dendritic cells, macrophages, T cells, B cells, reticulocytes), mesenchymal stem cells, and embryonic stem cells (produce abundant exosomes).

In certain non-limiting embodiments, the exosome-producing cells may be human cells. Exosomes produced by human cells may have reduced immunogenicity as compared to exosomes from mouse cells when introduced into human patients, which may be due to decreased differences in histocompatibility complexes (Bach, 1987, N Engl J Med, 317:489).

In another non-limiting embodiment, the exosome-producing cells may be embryonic stem cell (ESC) clone H1 or H9 cells, or a mesenchymal stem cell (MSC).

In another non-limiting embodiment, an exosome-producing cell may be an induced pluripotent stem cell, such as an induced pluripotent stem cell derived from a patient to be treated.

In certain non-limiting embodiments, the exosome-producing cells may be cultured in serum-free media, or in serum media which has been previously treated or processed to remove or reduce exosomal content (i.e. exosome-depleted serum media), while producing exosomes or exosome-like vesicles, so as to prevent or reduce contamination of produced exosomes with exosomes typically present in typical serum-containing media.

In certain non-limiting embodiments involving cells which require serum-containing media for growth, it may also be possible to remove the serum media and culture the cells temporarily in serum-free media during production/harvest of produced exosomes being released into the serum-free media. In certain cases, however, abrupt removal of serum media may decrease exosome production in certain cells.

Generally speaking, exosomes are typically 40-150 nm vesicles released by a variety of cell types. Exosomes may be composed of a lipid bilayer and a luminal space containing a variety of proteins, RNAs and other molecules derived from the cytoplasm of the exosome-producing cell. Both the membrane and lumen contents of exosomes may be selectively enriched in subpopulations of lipids, proteins and RNA from the exosome-producing cell. The exosome membrane is frequently, but not necessarily, enriched in lipids including cholesterol and sphingomyelin and contain less phosphatidycholine. The membrane of exosomes may be enriched in particular proteins derived from the plasma membrane of cells such as tetraspanins (e.g. CD63, CD81 CD9), PrP and MHC class I, II. The exosome lumen may be enriched in proteins such as Flotillin1 and 2, annexin 1 and 2, heat shock proteins, Alix and Tsg101. Exosomes are frequently enriched in miR-451 or pre-miR-451.

It will be understood that exosomes as described herein may, in certain non-limiting embodiments, also encompass exosome-like vesicles. The person of skill in the art will recognize that references to exosomes herein may include other suitable exosome-like vesicles which may vary somewhat from typical exosomes, but are still functionally and/or structurally similar or related.

It will also be understood that exosome-producing cells as described herein may, in certain non-limiting embodiments, also encompass exosome-like vesicle-producing cells. The person of skill in the art will recognize that references to exosome-producing cells herein may include other suitable exosome-like vesicle-producing cells which produce exosome-like vesicles which may vary somewhat from typical exosomes but are still functionally and/or structurally similar or related.

As will be understood by the person of skill in the art, exosomes as described herein may also include, in certain non-limiting embodiments, other suitable exosome-like vesicles between 50-150 nm (which contain exosomal markers), and/or larger exosome-like vesicles of 100-600 nm.

It will be understood that a gene silencing nucleic acid may be any nucleic acid which reduces, prevents, or silences the expression of a target gene. Without wishing to be limiting, suitable gene silencing nucleic acids may include siRNAs, antisense oligonucleotides (AONs), short hairpin RNAs (shRNAs), microRNAs (miRNAs), or other RNA interference (RNAi) or antisense oligonucleotide (AON) gene silencing triggers, among others. For example, a gene silencing nucleic acid may comprise an siRNA antisense strand, or an antisense oligonucleotide, which is fully, substantially, or partially complementary to a target mRNA. By way of non-limiting example, an siRNA/miRNA may be fully, substantially, or partially complementary (i.e. have seed-region complementarity at nucleotides 2-7) to a region of the gene-expressed mRNA sequence to be silencing by triggering RISC.

It will further be understood that a gene silencing nucleic acid may be a nucleic acid which affects transcription rates or epigenetic control of gene expression. Gene silencing nucleic acids may include, by way of non-limiting example, small RNAs with gene expression regulatory properties. By way of further non-limiting example, a gene silencing nucleic acid may comprise a CRISPR nucleic acid, such as a CRISPR guide RNA.

When reviewing the various examples and/or embodiments outlined herein, the person of skill in the art will recognize that a gene silencing nucleic acid may be any nucleic acid which causes the expression of a particular gene within a cell to be reduced, prevented, or "silenced". By way of non-limiting example, a gene silencing nucleic acid may be, or may be derived from, an siRNA (small interfering RNA), an antisense oligonucleotide (AON), a short hairpin RNA (shRNA), a microRNA (miRNA), or another RNA interference (RNAi) or antisense gene silencing trigger, among others (see, for example, Gaynor et al., RNA interference: a chemist's perspective. Chem. Soc. Rev. (2010) 39, 4196-4184; Bennett et al., RNA Targeting Therapeutics: Molecular Mechanisms of Antisense Oligonucleotides as a Therapeutic Platform, Annual Review of Pharmacology and Toxicology, 50, 259-293). A gene silencing nucleic acid may decrease gene expression by any mechanism, for example but not limited to a pre- or post-transcriptional gene silencing technique as will be known in the art. Given a particular gene sequence, the person of skill in the art will be able to design gene silencing nucleic acids capable of targeting said gene sequence, reducing expression (either transcription, translation, or both) of the gene. Various software-based tools are available for designing siRNAs or AONs for targeting a particular gene, including those available from the Whitehead Institute (http://sirna.wi.mit.edu/), or those available from commercial providers of siRNAs and AONs. Gene silencing nucleic acids may be prepared as described in, for example, Current Protocols in Nucleic Acids Chemistry, published by Wiley.

It will be understood that, in certain non-limiting embodiments, a miRNA may include naturally expressed miRNA sequences, and also nucleic acids having a miRNA-like mechanism of action, but having a nucleic acid sequence which does not match a naturally expressed miRNA sequence.

It will also be understood that, in certain non-limiting embodiments, a nucleic acid as described herein may include one or more chemical modifications to the nucleic acid backbone, sugar, or nucleobase, as will be known to the person of skill in the art. By way of non-limiting example, a nucleic acid as described herein may be a modified nucleic acid comprising one or more chemical modifications which increase target binding affinity, specificity, stability, loading into Ago proteins, and/or resistance to nuclease degradation, and/or reduce off-target effects. Examples of chemical modifications to nucleic acids are well-known in the art, examples of which are described in, for example, Gaynor et al., RNA interference: a chemist's perspective. Chem. Soc. Rev. (2010) 39, 4196-4184 and Bennett et al., RNA Targeting Therapeutics: Molecular Mechanisms of Antisense Oligonucleotides as a Therapeutic Platform, Annual Review of Pharmacology and Toxicology, 50, 259-293.

In certain non-limiting embodiments, a gene silencing nucleic acid, such as a short hairpin RNA (shRNA)- or siRNA-type nucleic acid, or another miRNA or RNAi-type nucleic acid, or a suitable nucleic acid derived therefrom, may be used. The gene silencing nucleic acid may have full sequence complementarity to the mRNA or RNA target, partial sequence complementarity, or seed region complementarity. Sequences may have, by way of non-limiting example, 15 nt-, 16 nt-, 17 nt-, 18 nt-, 19 nt-, 20 nt-, 21 nt-, 22 nt-, 23 nt-, or 24 nt-sequence complementarity, either consecutively positioned or spread over the length of the nucleic acid sequence, or any range defined as spanning any two of these values, or any range defined as spanning any two of these values and excluding one or more of these values. By way of non-limiting example, a sequence may have full complementarity, such as 24 nt full complementarity, or 17-19 nt complementarity. In further non-limiting embodiments, sequence non-complementarity, or sequence mismatches, between the gene silencing nucleic acid, such as an shRNA or siRNA, and the mRNA or RNA target may occur at one or more sites, such as, for example, one or more of positions 3, 4, 5, 6, 7, 8, 9, 14, 15, 16, 17, 18, 19, 20, 21, 22, or 23, counting from the 5' end of the mature gene silencing nucleic acid, or any range defined as spanning any two of these values, or any range defined as spanning any two of these values and excluding one or more of these values.

It will also be understood that a precursor of a gene silencing nucleic acid may be any nucleic acid sequence which is capable of providing a gene silencing nucleic acid to a cell. By way of non-limiting example, a pre-miRNA may be considered as a precursor of a gene silencing nucleic acid, as pre-miRNA is enzymatically processed by cells to produce mature miRNA. Similarly, longer dsRNAs may be processed by cells to produce siRNAs. In certain non-limiting embodiments, a precursor of a gene silencing nucleic acid may be or may comprise a miRNA or siRNA incorporated within a pre-miR-451 nucleotide backbone sequence as described in further detail below, or an enzymatic cleavage product thereof.

Figure 2:
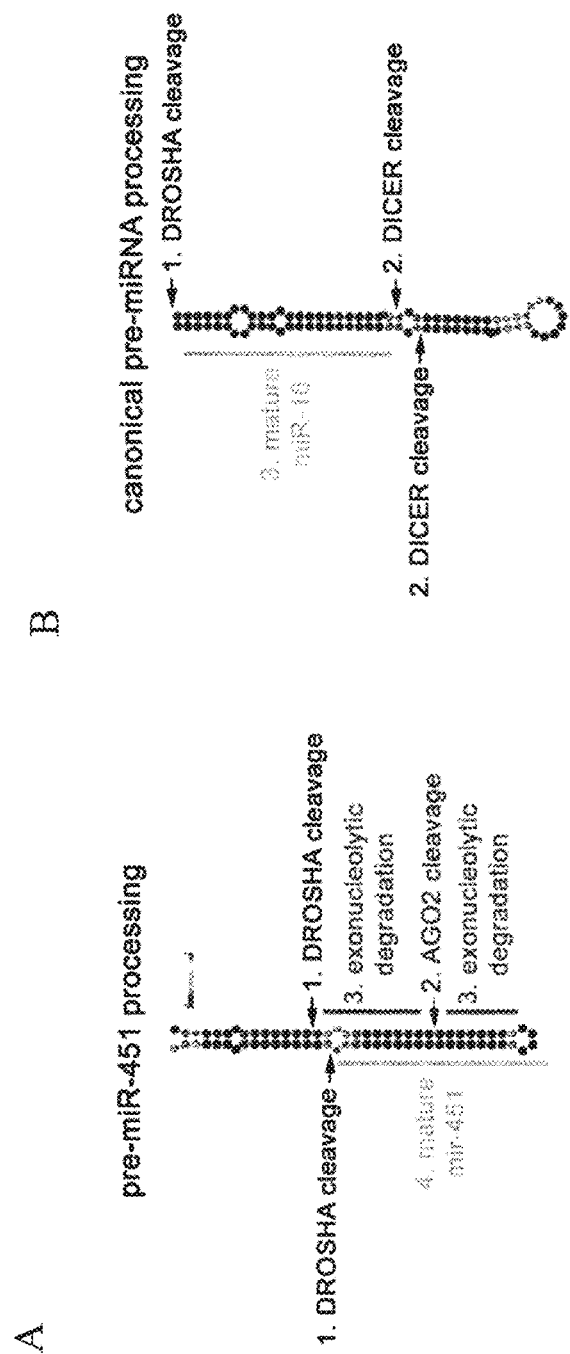
FIG. 2 shows the unique biogenesis pathway of miR-451. (A) Pre-miR-451 is a shorter hairpin structure that is cleaved in a DICER-independent and AGO2-dependent manner. Pre-miR-451 is a unique example of a miRNA that does not require cleavage by Dicer. After initial cleavage by Drosha, into a hairpin structure shorter than most pre-miRNA, pre-miR-451 is cleaved by Argonaute 2 (AGO2). Subsequent trimming of the 3' end of the resulting RNA generates mature miR-451. Several studies have demonstrated that a variety of other miRNAs or silencing RNAs may be inserted into the pre-miR-451 backbone and it will still be processed in a Dicer-independent, AGO2-dependent manner to become effective mature silencing RNAs (Cheloufi, Nature, 2010; Cifentes, Science, 2010; Yang, PNAS, 2010; Yang RNA 2012). Indeed, the sequence of mature miR-451 (item 4, in FIG. 2A) may be replaced with virtually any other suitable RNA sequence, and the processing may occur in generally the same manner. By way of example, data provided herein shows that mature-miR-451 may be replaced with miR-106 or miR-155, for example. (B) Canonical pre-miRNAs (typically ~70-120 nucleotides and having a double-stranded hairpin loop structure) are cleaved by DICER, after initial processing by DROSHA. The pre-miRNA is cleaved by DICER to generate a short ~21 nucleotide double-stranded RNA. After removal of one strand, a mature miRNA, such as for example miR-16 shown here, is generated. The sequential steps of biogenesis of each type of miRNA is numbered.

The pri-miR-451 nucleic acid sequence is shown in FIG. 2A, and is herein referred to as SEQ ID NO: 2. As shown in FIG. 2A, pri-miR-451 is processed by DROSHA to produce pre-miR-451 (the sequence of which is underlined in SEQ ID NO: 2 below, and is provided in SEQ ID NO: 3). Pre-miR-451 is then cleaved by Ago2 to generate SEQ ID NO:4. This RNA is then trimmed on its 3' end to generate processively shorter RNAs, most commonly SEQ ID NO: 5 (Cifuentes, Science, 2010).

SEQ ID NO: 2:    5'-CUU GGG AAU GGC AAG GAA ACC GUU ACC AUU ACU GAG UUU AGU AAU GGU AAU GGU UCU CUU GCU AUA CCC AGA-3' (pre-miR-451 miRNA region underlined)

SEQ ID NO: 3:    5'-AA ACC GUU ACC AUU ACU GAG UUU AGU AAU GGU AAU GGU UCU C-3' (loop region underlined)

SEQ ID NO: 4:    5'-AA ACC GUU ACC AUU ACU GAG UUU AGU AAU GG-3'

SEQ ID NO: 5:    5'-AA ACC GUU ACC AUU ACU GAG UUU-3'

In certain non-limiting embodiments, structural mimics of pre-miR-451 which incorporate a nucleic acid of interest, such as a gene silencing nucleic acid, may be designed based on a knowledge of the miR-451 enzymatic processing pathway outlined above. If, for example, an siRNA or miRNA guide strand is to be packaged in an exosome for delivery to a target cell for the purpose of silencing the expression of a target gene, then a pre-miR-451 structural mimic for this application may, by way of non-limiting illustrative example, be designed as follows:

- Identify an siRNA or miRNA guide strand sequence of interest;
- Use the siRNA or miRNA guide strand sequence in forming the 5' stem portion of the pre-miR-451 mimic and, optionally, in forming all or a portion of the pre-miR-451 mimic loop region and, optionally, extending partially into the 3' stem portion at the 5' side;
- Identify a sequence complementary, or substantially complementary, to the portion of the identified siRNA or miRNA guide strand sequence of interest which is present in the 5' stem portion of the pre-miR-451 mimic;
- Use the identified complementary sequence in forming the 3' stem portion of the pre-miR-451 mimic; and
- Optionally, confirm that the designed pre-miR-451 mimic is processed in a Dicer-independent, AGO-2 dependent manner similar to that of pre-miR-451, optionally using suitable methods such as, for example, those described in by Yang et al., PNAS, 2010, 107(34):15163-15168.

Further examples of "reprogramming" miR-451 mimics to target other genes may be found in Yang et al., PNAS, 2010, 107(34):15163-15168 and in U.S. Pat. No. 8,273,871, both of which are herein incorporated by reference in their entirety.

It will be understood that nucleic acid constructs as described herein may be chemically synthesized using, for example, solid phase synthesis, or other methods known in the art. Nucleic acid constructs may also be prepared by cellular or in vitro expression from a suitable expression vector as will be known in the art. Variants, chemically modified analogues, and structural mimics of nucleic acid constructs as described herein may also be possible. By way of example, some variants and structural mimics of pri- and/or pre-miR-451 are described in U.S. Pat. No. 8,273,871, which is herein incorporated by reference in its entirety.

It will be understood that a nucleic acid construct may be introduced into a cell, expressed in a cell, or caused to be produced by a cell, using any of a number of well-known methods. Introduction of a nucleic acid construct into a cell may include expression of the nucleic acid construct within a cell using a method as described herein, or using a suitable method known in the art, and/or may include direct introduction of the nucleic acid construct into the cell via, for example, transfection.

Expression vectors (either viral, plasmid, or other) may be transfected, electroporated, or otherwise introduced into cells, which may then express the nucleic acid construct(s). Alternatively, nucleic acid constructs themselves may be directly introduced into cells, for example via transfection or electroporation (i.e. using a transfection reagent such as but not limited to Lipofectamine™, Oligofectamine, or any other suitable delivery agent known in the art), or via targeted gene or nucleic acid delivery vehicles known in the art. Many delivery vehicles and/or agents are well-known in the art, several of which are commercially available. Delivery strategies for nucleic acids are described in, for example, Yuan et al., Expert Opin. Drug Deliv. (2011) 8:521-536; Juliano et al., (2012) Acc. Chem. Res. 45: 1067-1076; and Rettig et al. Mol. Ther. (2012) 20: 483-512. Examples of transfection methods are described in, for example, Ausubel et al. (1994) Current Protocols in Molecular Biology, John Wiley & Sons, New York. Expression vector examples are described in, for example, Cloning Vectors: A Laboratory Manual (Pouwels et al., 1985, Supp. 1987). Further examples are discussed in Example 11 below.

It will be understood that introduction of a nucleic acid construct into a cell may refer to the production of a nucleic acid within a cell from a gene (i.e. transcription), such an exogenous gene which has been introduced into the cell.

More generally, in terms of silencing gene expression, it will be understood that gene expression may include both transcription and translation processes, and so gene expression may refer to production of a nucleic acid sequence such as an mRNA (i.e. transcription), production of a protein (i.e. translation), or both.

Introduction of gene or a transcribed sequence into a cell may be accomplished using any of several methods known in the art. By way of example, a vector (either viral, plasmid, or other) comprising one or more copies of the particular gene each driven by a suitable promoter sequence (for example, a constitutive or inducible promoter), may be introduced into cells via transfection, electroporation, or viral infection, or another suitable method know in the art. Suitable expression vector techniques for overexpressing or introducing a particular gene into a cell are known in the art (see, for example, Molecular Cloning: A Laboratory Manual (4th Ed.), 2012, Cold Spring Harbor Laboratory Press).

Introduction of a gene (or a transcribed sequence/region), in the context of inserting a nucleic acid sequence into a cell, refers to "transfection", "transformation", or "transduction", and includes the incorporation or introduction of a nucleic acid sequence into a eukaryotic cell where the nucleic acid sequence may optionally be incorporated into the genome of the cell, or transiently expressed (for example, transfected mRNA).

It will be understood that compounds and/or compositions comprising or consisting of one or more of the nucleic acids and/or exosomes as described herein may be used. Compositions may additionally comprise one or more pharmaceutically acceptable diluents, carriers, excipients, or buffers.

As referenced herein, percent (%) identity or % sequence identity with respect to a particular sequence, or a specified portion thereof, may be defined as the percentage of nucleotides or amino acids in the candidate sequence identical with the nucleotides or amino acids in the subject sequence (or specified portion thereof), after aligning the sequences and introducing gaps, if necessary, to achieve the maximum percent sequence identity, as generated by the program WU-BLAST-2.0 with search parameters set to default values (Altschul et al., J. Mol. Biol. (1990) 215:403-410; website at blast.wustl.edu/blast/README.html).

By way of example, a % identity value may be determined by the number of matching identical nucleotides or amino acids divided by the sequence length for which the percent identity is being reported. Percent (%) amino acid sequence similarity may be determined by the same calculation as used for determining % amino acid sequence identity, but may, for example, include conservative amino acid substitutions in addition to identical amino acids in the computation. Oligonucleotide alignment algorithms such as, for example, BLAST (GenBank; using default parameters) may be used to calculate sequence identity %.

An alternative indication that two nucleic acid sequences may be substantially identical is that the two sequences hybridize to each other under moderately stringent, or preferably stringent, conditions. Hybridization to filter-bound sequences under moderately stringent conditions may, for example, be performed according to Ausubel, et al. (eds), 1989, Current Protocols in Molecular Biology, Vol. 1, Green Publishing Associates, Inc., and John Wiley & Sons, Inc., New York, at p. 2.10.3. Alternatively, hybridization to filter-bound sequences under stringent conditions may, for example, be performed according to Ausubel, et al. (eds), 1989, supra. Hybridization conditions may be modified in accordance with known methods depending on the sequence of interest (sec, for example, Tijssen, 1993, Laboratory Techniques in Biochemistry and Molecular Biology—Hybridization with Nucleic Acid Probes, Part 1, Chapter 2 "Overview of principles of hybridization and the strategy of nucleic acid probe assays", Elsevier, New York. Generally, by way of non-limiting example, stringent conditions may be about 5° C. lower than the thermal melting point for the specific sequence at a defined ionic strength and pH.

As will be known to one of skill in the art, nucleotide sequences for expressing a particular gene or transcribed sequence/region may encode or include features as described in "Genes VII", Lewin, B. Oxford University Press (2000) or "Molecular Cloning: A Laboratory Manual", Sambrook et al., Cold Spring Harbor Laboratory, 3rd edition (2001). A nucleotide sequence encoding a particular nucleic acid construct may be incorporated into a suitable vector, such as a commercially available vector. Vectors may also be individually constructed or modified using standard molecular biology techniques, as outlined, for example, in Sambrook et al. (Cold Spring Harbor Laboratory, 3rd edition (2001)). The person of skill in the art will recognize that a vector may include nucleotide sequences encoding desired elements that may be operably linked to a nucleotide sequence encoding a nucleic acid construct. Such nucleotide sequences encoding desired elements may include transcriptional promoters, transcriptional enhancers, transcriptional terminators, and/or an origin of replication. Selection of a suitable vector may depend upon several factors, including, without limitation, the size of the nucleic acid to be incorporated into the vector, the type of transcriptional and translational control elements desired, the level of expression desired, copy number desired, whether chromosomal integration is desired, the type of selection process that is desired, or the host cell or the host range that is intended to be transformed.

It will be understood that contemplated herein is a nucleic acid comprising a sequence:
a) encoding a nucleic acid as defined herein, or a fragment thereof;
b) that is the complement of a sequence encoding a nucleic acid as defined herein, or a fragment thereof,
c) that is capable of hybridizing to a nucleic acid as defined herein or fragment thereof under stringent hybridization conditions; or
d) that exhibits greater than or equal to about 70%, or greater than or equal to about 85%, sequence identity with the nucleic acid defined in a) or b) or another nucleic acid sequence as described herein, for example, but not limited to, 86%, 87%, 88%, 89%, 90%, 91%, 92%, 93%, 94%. 95%, 96%, 97%, 98%, 99%, or 100%. The nucleic acid may also be characterized by a range of identities, for example any two of the percentages outlined above.

The stringency of hybridization may be controlled by temperature, ionic strength, pH, and the presence of denaturing agents such as formamide during hybridization and washing. Conditions routinely used would be well known to those in the art (see, for example, Current Protocol in Molecular Biology, Vol. I, Chap. 2.10, John Wiley & Sons, Publishers (1994)).

The person of skill in the art will understand that biomolecules and/or compounds described herein may be provided in pharmaceutical compositions together with a pharmaceutically acceptable diluent, carrier, or excipient, and/or together with one or more separate active agents or drugs as part of a pharmaceutical combination or pharmaceutical composition. In certain embodiments, the biomolecules, compounds, and/or pharmaceutical compositions may be administered in a treatment regimen simultaneously, sequentially, or in combination with other drugs or pharmaceutical compositions, either separately or as a combined formulation or combination.

Biomolecules, compounds, and/or compositions as described herein may include one or more pharmaceutically acceptable excipients, diluents, and/or carriers. A pharmaceutically acceptable carrier, diluent, or excipient may include any suitable carrier, diluent, or excipient known to the person of skill in the art. Examples of pharmaceutically acceptable excipients may include, but are not limited to, cellulose derivatives, sucrose, and starch. The person of skill in the art will recognize that pharmaceutically acceptable excipients may include suitable fillers, binders, lubricants, buffers, glidants, and disintegrants known in the art (see, for example, Remington: The Science and Practice of Pharmacy (2006)). Examples of pharmaceutically acceptable carriers, diluents, and excipients may be found in, for example, Remington's Pharmaceutical Sciences (2000-20th edition) and in the United States Pharmacopeia: The National Formulary (USP 24 NF19) published in 1999.

In certain embodiments of methods as described herein, the methods may further comprise a step of treating the exosome-producing cell with a lysosomal or autophagy inhibitor. By way of example, exosome-producing cells may be treated with inhibitors of lysosomal acidification or VIV0 ATPase for 2 to 72 hours to increase production of exosomes. Examples of such inhibitors may include Bafilomycin A1, concanamycin, and/or chloroquine. It is contemplated that other compounds having similar effects on lysosomes (i.e. affecting pH or $Ca^{2+}$ balance) may have similar effects, such as NAADP, for example.

In certain further embodiments of methods as described herein, the method may further comprise a step of inhibiting expression or activity of Ago2 in the exosome-producing cell. Ago2 may be decreased on inhibited as already described herein above, for example. In certain embodiments, Ago2 may be inhibited using an siRNA, antisense oligonucleotide, or other gene silencing nucleic acid, for example.

In a further embodiment, there is provided herein a method for increasing a level of a gene silencing nucleic acid, or a precursor thereof, within (or otherwise associated with) exosomes produced by an exosome-producing cell, said method comprising:
 introducing into the cell, or expressing in the cell, a nucleic acid construct comprising the gene silencing nucleic acid incorporated within a pre-miR-451 structural mimic; and
 allowing the cell to produce exosomes.

It will be understood that references to enriching or increasing a level of a gene silencing nucleic acid or a precursor thereof within exosomes may refer to any increase in the amount of the gene silencing nucleic acid (which may or may not be incorporated within a larger sequence) present within exosomes produced by a cell, as compared to the level of the gene silencing nucleic acid found in a corresponding untreated or control cell.

In still another embodiment, there is provided herein a method for packaging a gene silencing nucleic acid, or a precursor thereof, with or into an exosome, said method comprising:

introducing into an exosome-producing cell a nucleic acid construct comprising the gene silencing nucleic acid incorporated in a pre-miR-451 structural mimic; and allowing the cell to produce exosomes.

In further embodiments, a cell used in a method as described above may be an embryonic stem cell (ESC) clone H1 or H9 cell, or a mesenchymal stem cell (MSC). In still another embodiment, the cell may be an embryonic stem cell (ESC) clone H1 cell. In still another embodiment, the cell may be an embryonic stem cell (ESC) clone H9 cell. Additional examples of cells have already been described hereinabove, and are further discussed in Example 8 below. Results described in further detail below indicate that such cells may be capable of producing large numbers of exosomes. In still another embodiment, the cell used in a method as described above may be a cell which is cultured in serum-free media, or in serum media which has been previously treated or processed to remove or reduce exosomal content, while producing exosomes, so as to avoid or reduce contamination of exosomes present in typical serum-containing media, or to facilitate purification of produced exosomes. Indeed, exosomes are highly abundant in fetal bovine serum used to culture most cells, therefore in certain embodiments it may be beneficial to grow cells in serum-free media or in serum media which has been previously treated or processed to remove or reduce exosomal content.

While it is possible to grow cells in media using fetal bovine serum depleted of exosomes by ultracentrifugation or other methods, in certain embodiments and examples it may be advantageous to use cells that grow in serum-free media, to avoid contamination of remaining exosomes. Further, it may, in certain embodiments, be advantageous to use cells that do not require other cells to grow (e.g. feeder layers), and/or cells that grow independent of coating of the cell culture surface (e.g. Matrigel), which may contaminate exosome preparations in certain conditions. Stem cells in general, including H1 and H9 human embryonic stem cells in particular, produce abundant exosomes in serum-free media.

In still a further embodiment, a method described above may optionally further comprise a step of purifying or concentrating exosomes produced by the cell. By way of non-limiting example for illustrative purposes, exosomes may be purified by a number of methods including those detailed in Thery et al. Isolation and characterization of exosomes from cell culture supernatants and biological fluids. Curr Protoc. Cell Biol. 2006 (herein incorporated by reference in its entirety). These methods may include differential centrifugation, which involves centrifuging media from cells at low speeds (e.g. 200-2000 g) to eliminate cells and larger debris, recovering the supernatant, centrifuging at approximately 10 000 g for 30 minutes, recovering the supernatant and centrifuging at 100 000 g for 1-2 h. Alternatively, supernatant may be filtered using 0.45 um or 0.22 um filters (or similar) to replace the second or first and second centrifugation steps. Alternative methods to purify exosomes may include precipitation methods, such as those used in the Systems Biosciences Exoquick kit or similar kits sold by companies such as Life Technologies or Qiagen. Exosomes may also be purified using affinity-purification, such as beads coated with antibodies recognizing elements of exosomes. Exosomes amy also be purified using density gradients (e.g. sucrose density gradients) based on their unusual density (Thery et al. above, Lamparski et al. J. Immunological Methods 2002; herein incorporated by reference in its entirety). As well, Exosomes may be purified by chromatography, such as by size exclusion chromatography or field-flow fractionation as will be known to those of skill in the art.

In yet another embodiment, there is provided herein a composition comprising:

an exosome or exosome-like vesicle; and
a nucleic acid construct comprising a gene silencing nucleic acid incorporated in a pre-miR-451 structural mimic, or a precursor or an enzymatic cleavage fragment thereof;
wherein the nucleic acid construct, or precursor or enzymatic cleavage fragment thereof, is contained within the exosome, or carried on the exterior of the exosome, or a combination thereof.

It will be understood that, in certain non-limiting embodiments, a suitable precursor may include a pri-miR-451 structural mimic, or another nucleic acid sequence which may be enzymatically cleaved to form a pre-miR-451 structural mimic.

It will further be understood that, in certain non-limiting embodiments, a suitable enzymatic cleavage product may include a mature miR-451 structural mimic, or an intervening sequence occurring in the maturation process of the pre-miR-451 structural mimic.

It will additionally be understood that, in certain non-limiting embodiments, pri-miR-451 or pre-miR-451 structural mimics may be fully or partially processed during exosomal packaging by exosome-producing cells. As such, in certain non-limiting examples, packaged exosomes may comprise (either internally, externally, or a combination thereof) nucleic acids which comprise a pri-miR-451 structural mimic, a pre-miR-451 structural mimic, a mature (i.e. fully processed) product of the pre-miR-451 structural mimic (i.e., a mature miRNA, for example), or an intervening intermediate sequence occurring during processing therebetween.

The composition may, in certain embodiments, further include one or more additional nucleic acid constructs comprising another gene silencing nucleic acid incorporated in a pre-miR-451 structural mimic, or a precursor or an enzymatic cleavage fragment thereof, within the exosome, such that the exosome contains gene silencing nucleic acids targeting more than one gene, or more than one region of the same gene.

The composition may, in certain embodiments, further include one or more additional exosomes containing another nucleic acid construct comprising another gene silencing nucleic acid incorporated in a pre-miR-451 structural mimic, or a precursor or an enzymatic cleavage fragment thereof, such that the composition contains exosomes containing gene silencing nucleic acids targeting more than one gene, or more than one region of the same gene.

The composition may, in still further embodiments, further comprise one or more exosome-producing cells.

In yet another embodiment, the composition may further comprise a serum-free media which does not comprise serum, or a serum media which has been previously treated or processed to remove or reduce exosomal content.

In yet another embodiment, there is provided herein a use of a nucleic acid construct comprising a gene silencing nucleic acid incorporated within a pre-miR-451 structural mimic for packaging a gene silencing nucleic acid (optionally incorporated within a larger nucleic acid), or a precursor thereof, into an exosome produced by a cell, wherein the nucleic acid construct is for introduction into the same or a different cell.

In still another embodiment, there is provided herein a nucleic acid construct comprising a gene silencing nucleic acid incorporated within a pre-miR-451 structural mimic, for packaging a gene silencing nucleic acid, or a precursor thereof, into an exosome produced by a cell, wherein the nucleic acid construct is for introduction into, or expression in, the cell.

In a further embodiment, there is provided herein a method for preparing exosomes enriched with a nucleic acid sequence of interest, or a precursor thereof, said method comprising:
  introducing into an exosome-producing cell a nucleic acid construct comprising the nucleic acid sequence of interest incorporated within a pre-miR-451 structural mimic; and
  allowing the cell to produce exosomes.

It will be understood that a nucleic acid sequence of interest may be any suitable small nucleic acid sequences, for example, but not limited to, those which produce a benefit when delivered into a cell. Examples may include, but are not limited to, gene silencing nucleic acid sequences as previously described herein, or triplex-forming nucleic acids or other non-coding RNAs or small nucleic acids of interest which are known in the art. By way of non-limiting example, a nucleic acid sequence of interest may be a suitable nucleic acid which affects transcription rates or epigenetic control of gene expression such as those described in Zhang et al., 2014, Cell, 158:607-619 and Kiani et al., 2013, PLOS Genetics, 9(5):e1003498. By way of further non-limiting example, a nucleic acid sequence of interest may comprise a suitable nucleic acid which is a riboswitch, ribozyme, aptamer. CRISPR guide RNA, or splice-switching nucleic acid, or any other suitable nucleic acid sequence of interest known in the art.

In still a further embodiment, there is provided herein a nucleic acid delivery composition comprising:
  an exosome or exosome-like vesicle; and
  a nucleic acid construct comprising a gene silencing nucleic acid incorporated in a pre-miR-451 structural mimic, or a precursor or enzymatic cleavage fragment thereof;
wherein the nucleic acid construct is contained within the exosome or exosome-like vesicle, or carried on the exterior of the exosome or exosome-like vesicle, or a combination thereof.

In a further embodiment of a nucleic acid delivery composition, the exosome may be an exosome produced by an embryonic stem cell (ESC) clone H1 or H9 cell or a mesenchymal stem cell (MSC), or another cell as described herein.

In still a further embodiment of a nucleic acid delivery composition, the exosome may be an exosome produced by cells cultured in serum-free media, or by cells cultured in serum media which has been previously treated or processed to remove or reduce exosomal content.

In yet another embodiment, the nucleic acid delivery composition may be for silencing cellular expression of a gene targeted by the gene silencing nucleic acid.

In yet another embodiment, the nucleic acid delivery composition may be for delivering silencing RNAs to cells being used to produce biotherapeutics. By way of non-limiting example, where cells are being used to produce antibodies, vaccines or oncolytic viruses, silencing RNAs may be delivered to improve production or purity from cells, or may provide improved safety of the product.

In another embodiment, there is provided herein a method for identifying whether a candidate exosome-producing cell is an exosome-producing cell which is suitable for producing enriched exosomes or exosome-like vesicles using a nucleic acid construct comprising a gene silencing nucleic acid, nucleic acid of interest, or a precursor thereof, incorporated within a pre-miR-451 structural mimic, said method comprising:
  quantitating miR-451 content of exosomes produced by said candidate exosome-producing cell and determining whether miR-451 is exosomally enriched;
wherein exosomal enrichment of miR-451 indicates that the candidate exosome-producing cell is suitable for producing the enriched exosomes or exosome-like vesicles.

In a further embodiment, exosomal enrichment of miR-451 may be determined by comparing miR-451 exosomal levels with exosomal levels of a reference endogenously expressed miRNA which is not miR-451. In certain embodiments, the reference endogenously expressed miRNA may be miR-16 or lct-7a, or another suitable RNA or other component which may be expected to be packaged into exosomes independently of pre-miR-451 structural mimics.

In certain embodiments, it is further contemplated herein that packaged exosomes as described herein may be used, for example, in the production of biologicals. For example, such exosomes may be used to deliver siRNA to cells being used to produce recombinant growth factors, antibodies, or vaccines, the siRNA being designed so as to increase yield or quality of such biologicals. For example, siRNAs which increase tolerance of ER stress may improve yields or quality of antibodies, or siRNA which inhibits anti-viral responses of cells may increase yield or quality of vaccines, for example. Such exosomes as described herein may, in certain embodiments, be used in drug discovery and/or target validation research in cells and/or in animal models, for example.

Packaging of Nucleic Acids within Exosomes for Cellular Delivery

Exosomes represent a particularly interesting delivery option for gene silencing nucleic acids. If efficient in vivo delivery of gene silencing nucleic acids can be achieved, treatment options for a variety of diseases may become available. As well, efficient in vivo delivery of gene silencing nucleic acids may facilitate therapeutic target validation in the drug discovery process, since the in vivo silencing of a gene of interest may be used to determine the phenotypic outcome without requiring the development of small-molecule drug inhibitors.

Evidence indicates that an exosome-mediated delivery approach may capitalize on, and repurpose, an endogenous system for intercellular communication with proven delivery in challenging tissues, like the brain. As well, evidence indicates that exosomes may be modified to target a variety of specific cell types and tissues, and that exosomes have minimal toxicity and immunogenicity. Exosomes from MSC and immature dendritic cells have been targeted to the liver, immune system, lung and heart (Lai, 2010, Stem Cell Res, 4:214; Takahashi, 2013, J Biotechnol, 165:77; Wiklander, 2015, Journal of extracellular vesicles, 4:26316). Exosomes may also target thyroid or other organs with fenestrated vasculature (Komarova, 2010. Annual Review of Physiology, 72:463).

Generally, exosomes from different cell types have distinct receptors on their surface (derived from the plasma membrane of the exosome-producing cell). This may cause them to traffic distinctly in mice or humans and may cause them to be taken up by distinct ranges of cell types. They may also contain distinct profiles of RNA and lipid cargo.

It certain non-limiting embodiments, it may be possible for exosomes to be targeted to certain cells or tissues using targeting ligands added to the exosome surface chemically, covalently, or by adsorption. Receptors may also be added to the exosome surface by adding specific domains to receptors, causing them to be enriched in exosomes. Examples of such exosome targeting may be found in, for example, Ohno, Mol. Ther., 2013, 21:185 and Alvarez-Erviti, Nat. Biotech, 2011, 29:341-345, herein incorporated by reference in their entirety.

Exosomes package a highly selective subset of proteins and RNAs compared to the cells that produce them. For example, many miRNAs are virtually undetectable in exosomes despite their abundance in cells, and the inverse (Valadi, 2007, Nat Cell Biol, 9:654; Cheng, 2014, Journal of extracellular vesicles, 3: Collino, 2010, PLoS One, 5:e118093). Therefore, a major hurdle to using exosomes for drug delivery of nucleic acids is the development of a suitable method for packaging of gene silencing nucleic acids into exosomes in a manner that does not physically disrupt the biological structure and activity of exosomes.

There have been many attempts to identify strategies to enrich miRNA or other RNAs in exosomes. We previously discovered mechanisms regulating packaging of mRNA into exosomes (Gibbings, 2009, Nat Cell Biol, 11:1143), but this was not applicable to RNAi. Bioinformatics searches for sequence motifs enriched in exosomes discovered a few poorly enriched candidates (Batagov. 2011. BMC Genomics, 12(3):S18; Villarroya-Beltri, 2013, Nat Commun, 4:2980). The best sequence motif only enriched RNA 2-5-fold in exosomes in one cell type (Villarroya-Beltri, 2013, Nat Commun, 4:2980). Whether this modest effect is maintained in other cell types is unclear. Also, it would be challenging to retain targeting and efficacy of RNAi (21 nt) that relies on perfect complementarity with its targets, while also including a 6 nt motif for exosome enrichment. Electroporation putatively introduces RNAi therapeutics into exosomes (Alvarez-Erviti, 2011, Nat Biotechnol, 29:341). However, subsequent investigation demonstrated that the majority of RNAi therapeutics precipitated when electroporated using identical techniques (Kooijmans, 2013, J Control Release, 172:229). In addition, many doubts were raised that in bulk production of exosomes for clinical use one could consistently generate holes of 5-10 nm (RNAi~5 nm) in the membrane of 100 nm exosomes and consistently retain their biological functions. In sum, no widely applicable and robust mechanism has been previously identified.

Analyzing the RNA content of exosomes across studies, it was realized herein that in several studies of exosomes from multiple cell types and sources, including plasma and serum (Cheng, 2014, Journal of extracellular vesicles, 3), mast cells (Valadi, 2007, Nat Cell Biol, 9:654), glioblastoma, B cells, cardiac progenitor cells, and MSC (Collino, 2010, PLoS One, 5:e11803), one notable miRNA is strongly enriched in exosomes (10-10000-fold). This miRNA is miR-451. Fascinatingly, this miR-451 has a unique biogenesis mechanism compared to all other miRNAs (see FIG. 2), miR-451 is the only known miRNA that is generated without cleavage by the RNAse III enzyme Dicer. Dicer cleaves the stem-loop structure of all other pre-miRNAs into a mature ~22 nt miRNA. In contrast, pre-miR-451 has a uniquely short stem-loop among miRNA precursors (51 nt vs. 70-120 nt), and binds directly to Ago2, a ubiquitous miRNA binding protein, rather than Dicer (Cheloufi, 2010, Nature, 465:584: Yang, 2012, RNA, 18:945). Ago2 itself cleaves pre-miR-451, which, with subsequent trimming by other ubiquitous enzymes generates mature miR-451. Without wishing to be bound by theory, it may be the stem-loop structure of pre-miR-451 which provides for its unique biogenesis. Studies demonstrated that one could substitute virtually any mature miRNA sequence into the backbone of the pre-miR-451 stem-loop and it would be processed in the same way (Yang et al., 2010, PNAS, 107(34):15163-15168; Cheloufi, 2010. Nature, 465:584; Yang, 2012, RNA. 18:945).

U.S. Pat. No. 8,273,871 outlines some examples of nucleotides and secondary structures in the pre-miR-451 backbone which affect miR-451 biogenesis, as well as Cheloufi, 2010, Nature, 465:584 and Yang, 2012, RNA, 18:945, the disclosures of which is herein incorporated by reference in their entirety.

Examples of suitable nucleic acid constructs for packaging gene silencing nucleic acids in exosomes are described herein in detail. Furthermore, it will be understood that other suitable nucleic acid constructs for packaging gene silencing nucleic acids into exosomes may be identified using methods as provided herein. By way of example, constructs may be transfected into MEF and/or another candidate cell for clinical production of exosomes. Absolute levels of RNAi in cells and exosomes may then be measured by digital PCR. Tested nucleic acid constructs that make significant changes in exosome abundance of gene silencing nucleic acids may be further tested using Northern blot to test for changes in gene silencing nucleic acid excision and maturation from the nucleic acid construct. These studies may be used to identify nucleic acid constructs that are suitable for packaging siRNA/RNAi, or other gene silencing nucleic acids, or other nucleic acid sequences of interest, into exosomes. In certain embodiments, vectors may be inserted in safe loci in candidate cells using Crispr/Cas9 for study.

It will be understood that exosomes may carry nucleic acid sequences internally, externally, or both. Exosomes may carry nucleic acids externally via external attachment or adsorption, for example. As such, it will be understood by the person of skill in the art that, in certain non-limiting embodiments, references herein to exosomes enriched with, comprising, or packaged with a particular nucleic acid sequence may refer to exosomes carrying the nucleic acid sequence internally, externally, or a combination thereof.

Example 1: Nucleic Acid Constructs for Exosomal Packaging of Gene Silencing Nucleic Acids In certain embodiments, there is provided herein nucleic acid constructs comprising a gene silencing nucleic acid incorporated within a pre-miR-451 structural mimic. In the figures, miR-155, miR-106 and miR-199 have been substituted into such a nucleic acid construct, allowing for packaging of the gene silencing nucleic acids within exosomes.

Indeed, data is provided herein demonstrating that any of five different miRNAs may be enriched by up to 1000-fold in exosomes by inserting them into a pre-miR-451 structural mimic. Moreover, this enrichment occurs in at least two distinct cell types, suggesting it may be applicable to a wide variety of different cells.

Exosomes from breast epithelial cell line (MDA-MB-231) or mouse embryonic fibroblasts (MEF) were purified and multiple techniques were used to confirm the identity and purity of exosome preparations (see FIG. 1A-D). Dynamic light scattering and Nanosight particle tracking was used to ensure that exosomes purified were highly pure populations of particles with diameter of 100 nm, as expected for exosomes. Western blot was used to demonstrate the enrichment of these preparations of 100 nm vesicles in established markers of exosomes (see FIG. 1D,E). RNA was isolated from these exosomes and the cells that produced them, and RT-qPCR was used to characterize the relative abundance of miRNAs.

Figure 3:
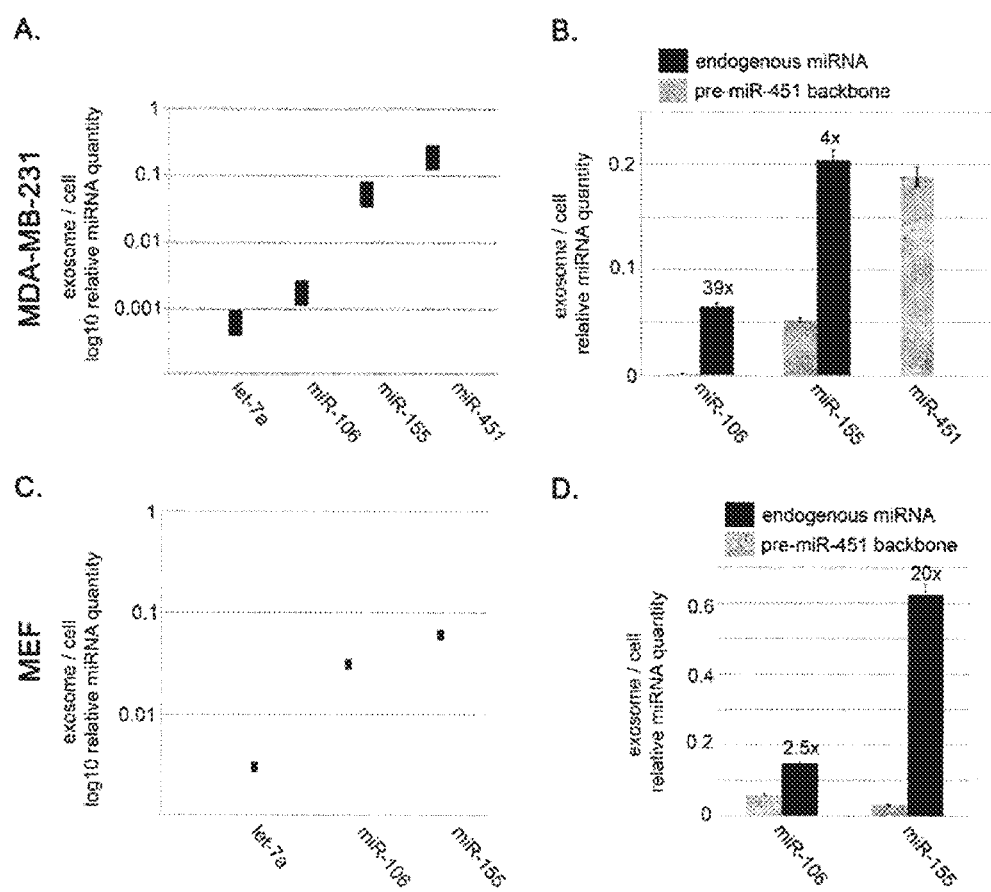
FIG. 3 shows that insertion in pre-mIR-451 backbone causes miRNAs to be strongly enriched in exosomes. (A) The ratio of endogenous miRNAs (let-7a, miR-106, miR-155, miR-451) was measured in exosomes and exosome-producing cells (MDA-MB-231) by RT-qPCR, y-axis is log 10, miR-451 is highly enriched in exosomes. (B) Insertion of miR-106 or miR-155 in the pre-miR-451 backbone causes them to be enriched in exosomes from MDA-MB-231 cells to a level comparable with miR-451. (C) The ratio of endogenous miRNAs (let-7a, miR-106, miR-155) was measured in exosomes and exosome-producing cells (MEF, mouse embryonic fibroblasts) by RT-qPCR. y-axis is log 10. miR-451 is not endogenously expressed in these cells. (D) Insertion of miR-106 or miR-155 in the pre-miR-451 backbone causes them to be highly enriched in exosomes from MEF cells.

In breast epithelial cells (MDA-MB-231) the degree of enrichment of four different miRNA in exosomes varied over several logs, miR-451 was the miRNA most highly enriched in exosomes compared to cells (see FIG. 3A). Other miRNA were much less enriched in exosomes (e.g. let-7a 308-fold less, miR-106 114-fold less). Indeed, compared to other miRNA, miR-451 was enriched up to 308-fold in exosomes compared to its levels in cells (see FIG. 3A), confirming that miR-451 is highly enriched in exosomes.

Figure 4:
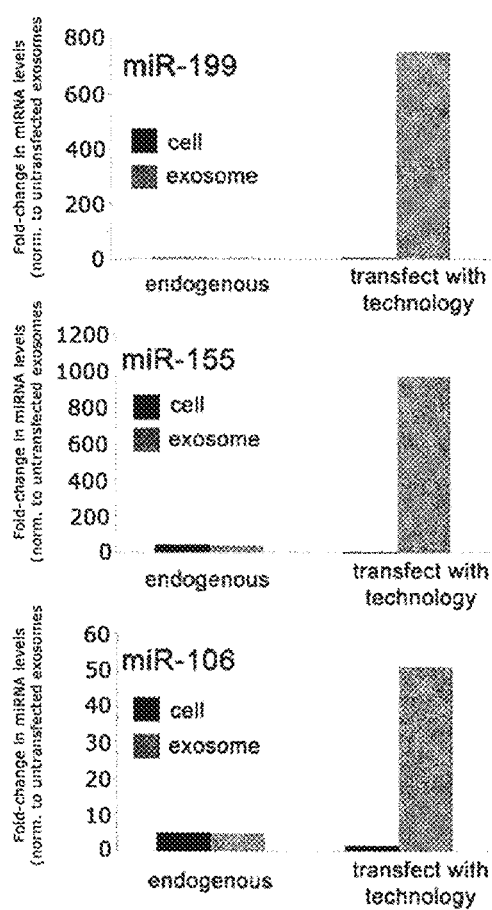
FIG. 4 shows that in certain conditions, insertion of miRNA into the pre-miR-451 backbone may cause enrichment of miRNA up to 1000-fold in exosomes. MEF cells were transfected with pre-miR-451 expressing plasmids ("technology") containing miR-199, miR-155 or miR-106, and exosomes were purified and RT-qPCR was performed on exosomes and cells. Pre-miR-451 had neglible effects on levels of inserted miRNA in cells, but caused 100-1000-fold increases in miRNA in exosomes.

Plasmids expressing pre-miR-451, or pre-miR-451 structural mimics including the sequences of other miRNA, were transfected into the two cell types. Expressing miR-106 or miR-155 in the pre-miR-451 structural mimic caused them to be enriched up to 39-fold in exosomes produced by either MEF or breast cancer cells (see FIG. 3B,D). Under certain conditions tested, results demonstrate that the pre-miR-451 structural mimic can enrich miRNA in exosomes up to 1000-fold, leaving very little extra miRNA in the cell (see FIG. 4). In MEF cells, endogenous miR-451 was undetectable in either cells or exosomes (see FIG. 3C). Nonetheless, expression of miR-106 or miR-155 from the pre-miR-451 structural mimic resulted in their enrichment in up to 20-fold in exosomes. These results indicate that pre-miR-451 structural mimics may be used to robustly package RNAi/siRNA or miRNA therapeutics in exosomes from different cell types, different species, and even in the absence of endogenous miR-451 (MEF).

In these experiments, pre-miR-451 structural mimics comprising the targeting sequence of miR-155, miR-106, and miR-199 were prepared and studied.

The pre-miR-451 structural mimic comprising the miR-155 targeting sequence had a primary sequence as follows:

5'-CUUGGGAAUGGCAAGG<u>UUAAUGCUAAUCGUGAUA</u>GGGGUAUCACGAU
UAGCAUUACUCUUGCUAUACCCAGA-3' (SEQ ID NO: 6; miR-
155 targeting sequence shown in underline; loop
shown in bold).

The pre-miR-451 structural mimic comprising the miR-106 targeting sequence had a primary sequence as follows:

5'-CUUGGGAAUGGCAAGG<u>AAAAGUGCUUACAGUGCA</u>GGUAUGCACUGUA
AGCACUUUCUCUUGCUAUACCCAGA-3' (SEQ ID NO: 7; miR-
106 targeting sequence shown in underline; loop
shown in bold).

The pre-miR-451 structural mimic comprising the miR-199 targeting sequence had a primary sequence as follows:

5'-CUUGGGAAUGGCAAGG<u>ACAGUAGUCUGCACAUU</u>GGUUAAUGUGCAGA
CUACUGUCUCUUGCUAUACCCAGA-3' (SEQ ID NO: 8; miR-
199 targeting sequence shown in underline; loop
shown in bold).

Other publications in the field have identified a 6 nucleotide motif that can modestly enrich miRNAs in exosomes in one tested cell type, or as expected that over-expressing a miRNA increases its levels in exosomes. In many cases it may be difficult to include a specific 6 nucleotide motif in a 21-22 nucleotide silencing RNA and still retain its specificity and activity. Moreover, the effects of this motif on sorting into exosomes are relatively modest (2-8-fold). As discussed in detail herein, there is provided herein a specific nucleotide secondary structure that results in strong enrichment of a given silencing RNA in exosomes. Moreover, this technology has been demonstrated in two independent cell types, providing evidence that it may be more broadly applicable. Therefore, there is provided herein a technology which may provide a larger effect and may be more applicable to diverse exosome-producing cell types and silencing RNAs.

Example 2: Identification of Cell Lines for Production of Exosomes Containing Gene Silencing Nucleic Acids It is demonstrated herein that in breast cancer cells and MEFs, insertion in a pre-miR-451 structural mimic causes miRNAs to be robustly packaged into exosomes. These results indicate that prc-miR-451 backbone may be used to robustly package RNAi or miRNA therapeutics in exosomes from different cell types, different species, and even in the absence of endogenous miR-451 (MEF). For clinical production of exosomes, which may require large-scale production, it may be of interest to use a cell line which is particularly well-suited for production of exosomes containing gene silencing nucleic acids. In this regard, relevant cell line characteristics may include: (1) abundant exosome production (2) minimal risk of immunogenic and oncogenic factors, or favorably immunogenic factors, and (3) reproducible, mass culture in xeno-free media. Exosomes from several cell types may meet these criteria, and they may exhibit distinct in vivo distribution, allowing treatment of unique diseases. Furthermore, exosome-producing cells may be stably genetically engineered for bulk production, rather than produced anew for each patient, reducing the inherent variability associated therewith. If, for example, primary dendritic cells were used, this may require taking blood from different donors, and differentiating cells for each new batch of exosomes. With ESC or MSC cells, it may be possible to continuously use the same cells and culture them in highly controlled conditions to reduce such variability, if desired.

Data indicates that RNAi/siRNA and miRNA are processed similarly from the pre-miR-451 structural mimic. Therefore, whether the silencing RNA inserted in the miR-451 structural mimic is perfectly complementary or not to its target RNA does not appear to affect its use for the technology.

Human embryonic stem cells (ES), mesenchymal stem cells (MSC), and primary immature dendritic cells derived from autologous blood monocytes were selected as three candidate cell types of interest. Data shows that specific ES clones and MSC, but not iPS cells, produce abundant exosomes (see FIG. 5). Primary dendritic cells have previously been used as a source of exosomes for clinical trials (Vlaud, 2011, J Immunother, 34:65).

Figure 5:
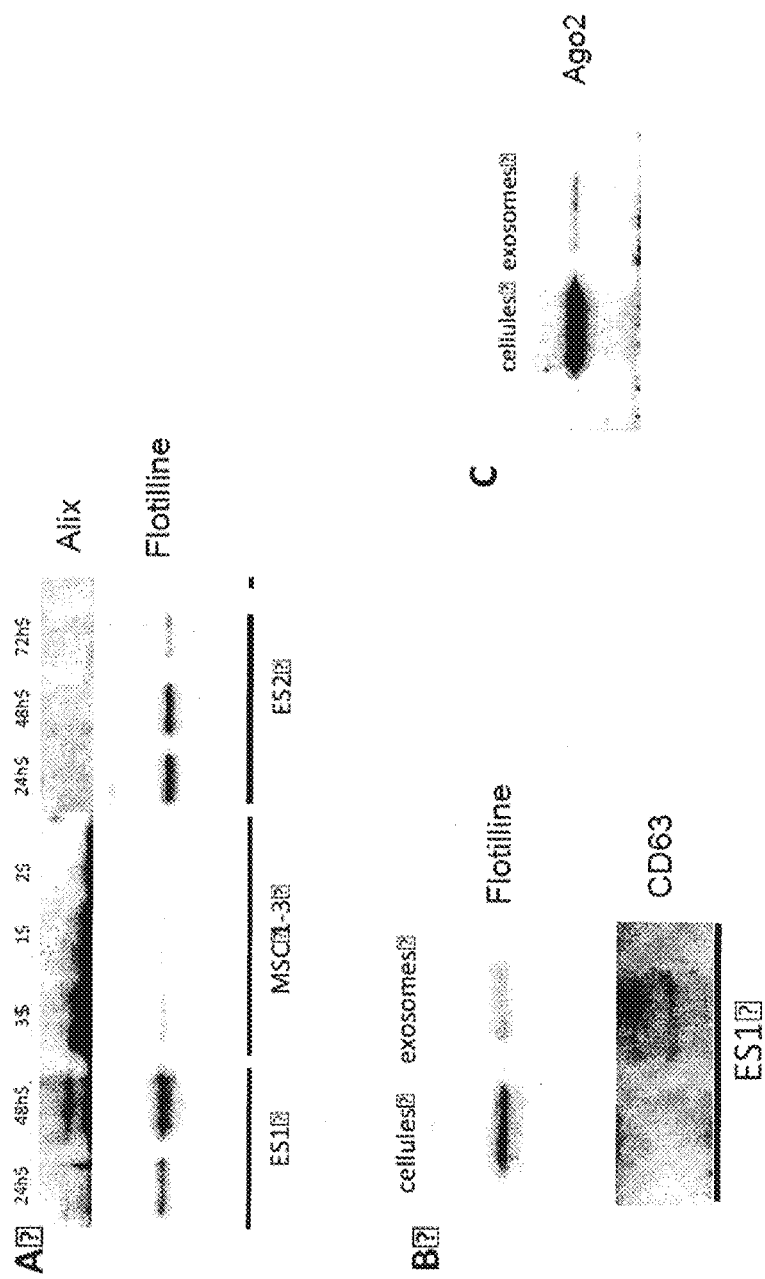
FIG. 5 shows that embryonic stem cells (ES) produce abundant exosomes. (A,B) Western blot of exosome preparations from human embryonic stem cells with exosome markers Alix, Flotillin2 and CD63. ES1 is human ES cell line H1. ES2 is human ES cell line ES2. MSC1-3 are three preparations of mesenchymal stem cells obtained from Wharton's jelly. According to literature MSC produce more exosomes than many cell types. ES cells appear to release a large amount of exosomes and may be very useful for bulk production of exosomes as therapeutics. (C) Exosomes from FS cells also contain Argonaute2 (AGO2), a protein involved in processing of pre-miR-451 into mature miR-451. Results indicate that ES cell exosomes may be a particularly interesting candidate for loading siRNA into using the pre-miR-451 backbone.

FIG. 5 shows that embryonic stem cells (ES) produce abundant exosomes. According to literature, MSC produce more exosomes than many cell types. ES cells appear to release a large amount of exosomes, suggesting that they may also be useful for bulk production of exosomes in therapeutic applications. Data also shows that exosomes from ES cells also contain Argonaute2 (AGO02), a protein involved in processing of pre-miR-451 into mature miR-451. Results indicate that ES cell exosomes may be an interesting candidate for loading a gene silencing nucleic acid into exosomes using a pre-miR-451 structural mimic.

Figure 6:
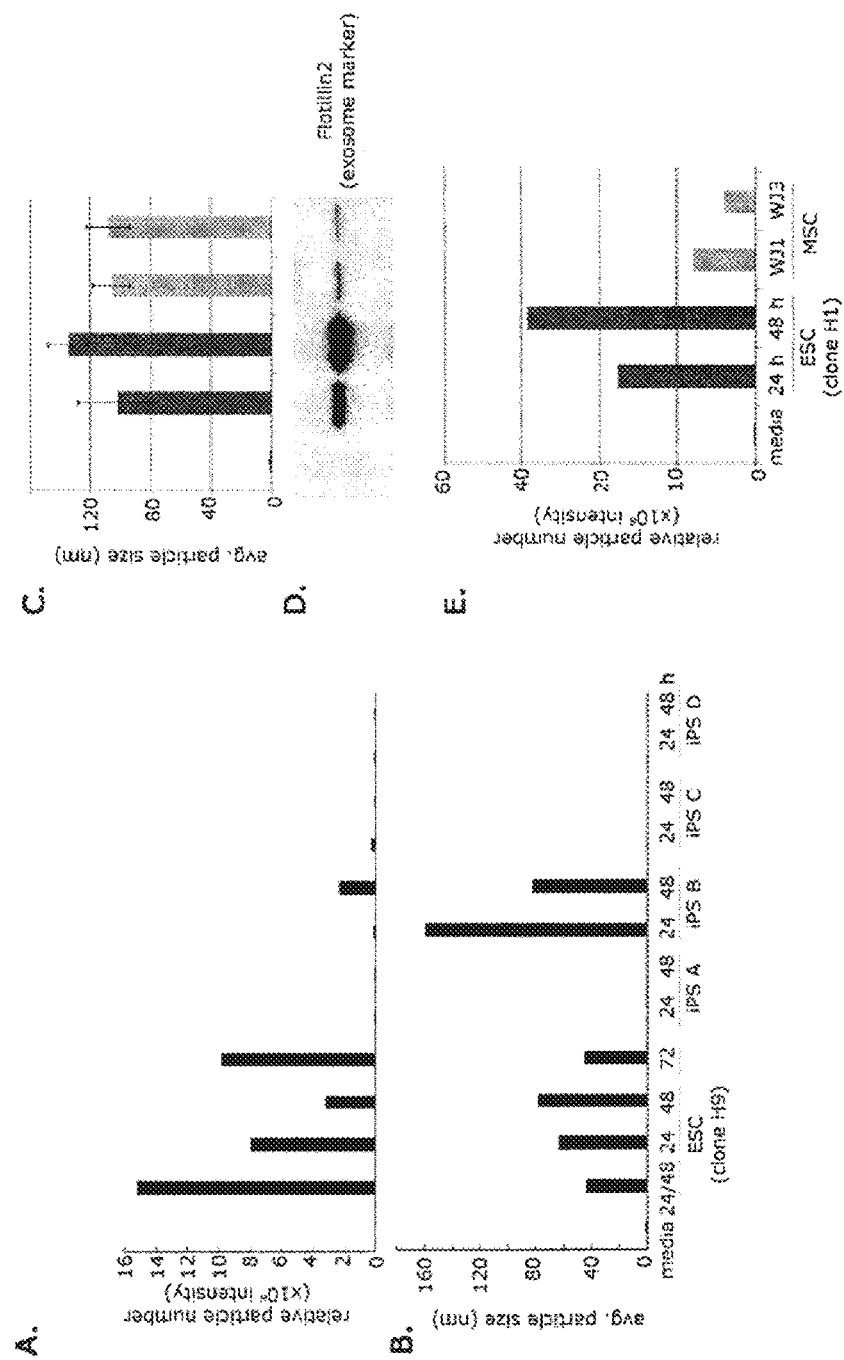
FIG. 6 shows selection of stem cells producing abundant exosomes. (A) Relative exosome quantity was measuring using dynamic light scattering intensity of exosome preparations prepared by differential centrifugation. Embryonic stem cell (ESC) clone H9 and one of four genetically distinct induced pluripotent cells (iPs) produced detectable levels of exosomes. (B) Exosome size was measured by dynamic light scattering for the same exosome preparations. Note that exosomes from ESC clone H9 produce exosomes that are small (60 nm), but within the normal range (40 nm-120 nm). (C) Exosome size measure by dynamic light scattering for ESC clone 11 and two batches of mesenchymal stem cells (MSC). (D) Western blot of the exosome marker Flotillin2 in exosome preparations from these cell types demonstrates presence and relative abundance of exosomes. (E) Relative exosome quantity was measured using dynamic light scattering intensity of exosome preparations from cells as in (D); Abundance by western blot and dynamic light scattering correlate closely. (E) Note that ESC clone H1 produces 10-fold more exosomes than clone H9, and several-fold more exosomes than MSC, widely regarded as producing large numbers of exosomes. ESC clone H1 and MSC may therefore be identified as lead candidates.

FIG. 6 shows a selection of stem cells producing abundant exosomes. Embyronic stem cell (ESC) clone H9 and one of four genetically distinct induced pluripotent cells (iPs) produced detectable levels of exosomes. ESC clone H1 produced 10-fold more exosomes than clone H9, and several-fold more exosomes than MSC, widely regarded as producing large numbers of exosomes. As such, lead candidates for clinical production of exosomes may include ESC clone H1, H9, and MSC. In certain non-limiting embodiments, ESC clone H9 may be a preferred cell line as it generally produces exosomes which are strongly enriched in miR-451 and may be particularly amenable to the technology described herein.

Figure 7:
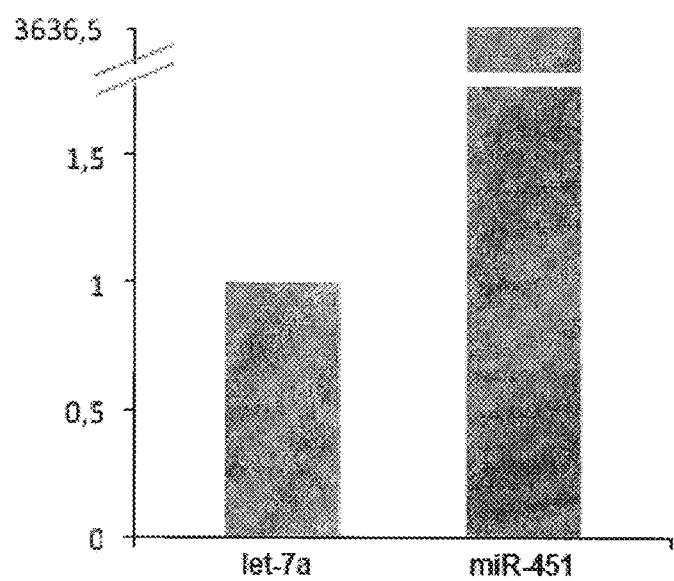
FIG. 7 shows that miR-451 is strongly enriched in exosomes from human embryonic stem cells (H9 line). This suggests that human embryonic stem cells, and in particular this cell line, may be particularly interesting for packaging siRNA into exosomes using a pre-miR-451 backbone.

FIG. 7 further shows that miR-451 is strongly enriched in exosomes from human embryonic stem cells (H9 line). This suggests that human embryonic stem cells, and in particular this cell line, may also be particularly interesting for packaging siRNA into exosomes using a pre-miR-451 structural mimic. As such, in certain non-limiting embodiments, the H9 cell line may be preferable for certain applications. Although the H9 cell line may, in some examples, produce slightly less exosomes than H1, versions of H9 are available that have been validated for GMP clinical use.

Example 3: Distribution of RNA-Loaded Exosomes in Mice

Achieving delivery of RNAi to any tissue other than liver may enable treatment of several diseases associated with that cell-type or tissue. Thus, exosomes produced from candidate cell types (for example, ES, MSC, and dendritic cells) may be tested for distribution in mice after intravenous or intraperitoneal injection. Exosome doses, determined by particle number (Nanosight) or protein quantity, may be tested using doses as used in other studies (Zhuang et al., Mol Ther 19, 1769 (2011), Alvarez-Erviti et al., Nat Biotechnol 29, 341 (2011)). By way of non-limiting example, cells may be generated which stably express firefly luciferase that is enriched in exosomes (e.g. tagged with a C1C2 domain, or cytoplasmic domain of LAMP2b) (Alvarez-Erviti et al., Nat Biotechnol 29, 341 (2011), Zeelenberg et al., Cancer Res 68, 1228 (2008)). This may enable imaging of exosome distribution throughout animals (CycLuc1 substrate for luciferase also allows imaging in brain) with high sensitivity and minimal background using IVIS technology. By way of non-limiting example, 3 mice/group may be used, and around a 4-fold increase in luc in some body regions may be expected ($\sigma=1$, $\alpha=0.05$, power=0.99).

Visualization of the distribution of exosomes outlined above may be performed, as well as visualization of the activity of exosome-delivered RNAi throughout mice, using a mouse developed for this purpose (Stevenson et al., Molecular therapy. Nucleic acids 2, e133 (2013)) having firefly luciferase constitutively repressed by the lac repressor in all tissues. RNAi targeting the lac repressor may be used to obtain results based on the appearance of luciferase wherever RNAi is active (Stevenson et al., Molecular therapy. Nucleic acids 2, e133 (2013)).

Cells (for example, ES, MSC and/or dendritic cells) stably expressing RNAi targeting lac repressor incorporated in pre-miR-451 or pre-miR-16 (control), or pre-miR-451 containing non-silencing RNAi may be studied, for example. As additional controls, mice may be imaged with the IVIS system before delivery of RNAi-loaded exosomes (for example, 4 mice/group, with an estimated 3-fold increase, $\sigma=1$, $\alpha=0.05$, power-0.99). The IVIS system may allow for mice to be imaged several times, allowing analysis of the pharmacokinetics of RNAi activity delivered by exosomes. RNAi molecules are long-lived in cells: over 5 days the only measurable affect on their abundance was dilution through cell division (Gantier et al., Nucleic Acids Res 39, 5692 (2011)) and chemical modification to prevent nuclease digestion may not alter this (Bartlett, Davis, Biotechnology and bioengineering 97, 909 (2007)). Therefore, the activity of a single dose of RNAi delivered by exosomes may persist for 5 days or more, and potentially up to 6-8 weeks like in animal studies of liposome-delivered RNAi (Coelho et al., N Engl J Med 369, 819 (2013). Bartlett, Davis, Biotechnology and bioengineering 97, 909 (2007)). Cell types receiving RNAi activity may be determined, and RNAi induced mRNA loss may be quantified. To enable linear quantification. RNAi targeting human SOD1 (ubiquitous mid-low expression in human wild-type SOD1 mouse) may be used in the pre-miR-451 backbone. Exosomes may be injected, and harvested tissues at time points guided by data from lac-repressor luciferase mice and exosome distribution (above) may be obtained. In sectioned formalin/paraffin tissues, SOD1 mRNA may be quantified using quantitative RNA FISH, and cell types may be identified based on morphology and antibodies to cell-specific markers.

In certain embodiments, it may be determined that exosomes may be taken up by immune cells at the root of many inflammatory diseases such as arthritis and lupus. Therefore, SOD1 mRNA (SmartFlares, Millipore) and protein (antibody, Cell Signalling) may be analyzed in blood T cells (TCR$\alpha$), T regulatory cells (CD25), B cells (CD19), monocytes (CD11b), NK cells (Nkp46) and granulocytes (Gr-1/Ly6G). SOD1 levels may be analyzed in blood from 5 animals treated with SOD1 RNAi or control (a 2-fold decrease in SOD1 in some cells may be expected, $\sigma=1$, $\alpha=0.05$, power=0.99). In tissues or blood where RNAi activity is identified in subsets of cells, these may be isolated using flow cytometry sorting on cell-specific markers to quantify mRNA and protein. These experiments may be used to identify in which tissues and cell-types exosomes effectively deliver RNAi, and to quantify RNAi-mediated knockdown.

RNAi activity may be assessed using a lac repressed-luciferase mouse model as described herein, where RNAi cleavage of lac repressor allows expression of luciferase. To ensure this effect is mediated by RNAi activity and quantify RNAi activity delivered by exosomes, loss of target mRNA (luciferase and SOD1 vs. 3 reference mRNAs) may be measured by RT-qPCR, and using quantitative RNA ISH on tissue sections. As further proof of RNAi activity in results in mice, 5'RACE may also be performed to semi-quantitatively identify the RNAi-specific cleaved mRNA.

Methods such as those described above may be used to determine the biodistribution of gene silencing nucleic acid-carrying exosomes, providing information as to which tissues may be targeted by the preparation and therefore which diseases may be therapeutically addressable.

Example 4: Testing Immunogenicity and Oncogenicity of Packaged Exosomes

Toxicity and immunogenicity of exosomes for clinical use may also be evaluated. For example, Illumina mRNA sequencing (polyA-selected libraries) and proteomics may be used to detect possible oncogenic factors. Exosomes may be incubated with peripheral blood mononuclear cells and supernatants may be assayed using a Luminex 29 cytokine/chemokine panel (Millipore).

Exosomes are normally produced by the body. Phase I trials with exosomes identified no toxicity issues (Viaud et al., J Immunother 34, 65 (2011)). Phase I trials demonstrated minimal immunogenicity of exosomes (when immunogenicity was the goal) and no oncogenicity (Viaud et al., J Immunother 34, 65 (2011)). Exosomes generated from ES and MSC sources may thus be minimally immunogenic. If detrimental effects of exosomes are noted, these may be abrogated by engineering RNAi for expression in source cells (e.g. MHC), or by including additional RNAi in exosomes.

Exosomes may contain other immune repressive or stimulatory molecules, and exosomes produced from non-autologous sources may risk being recognized as MHC incompatible. To address potential immunogenicity, exosomes may, in certain embodiments, be derived from stem cells that are among the most immune tolerant cells, and autologous patient-derived dendritic cells, which avoid MHC incompatibility. Although induced pluripotent stem cells may be made for each patient to produce autologous exosomes, the ability to produce large consistent batches of exosomes using, for example, ES or MSC cells, may be preferable in certain examples. Exosomes from MSC or immature dendritic cells show no immune response in literature or patients. If immunogenic responses are nonetheless detected, RNAi targeting critical immunogenic proteins in source cells may be added to limit or shape immunogenic response in certain embodiments. Non-transformed cells may be used to reduce risk of oncogenic properties of exosomes.

Exosomes, particularly from ES and MSC, may contain factors that promote stem-like properties, however these may be transiently present in patients in much lower doses than ES or MSC, and therefore the risk may accordingly be much less.

Example 5: Targeting Exosomes to Specific Tissues

Exosomes have endogenous targeting. For example Schwann and oligodendrocyte exosomes target neurons, neuron exosomes target astrocytes, mast cell exosomes target mast cells, macrophage exosomes target macrophage, and B cell exosomes target T cells. Based on this, exosomes from different cell types may traffic distinctly. Distribution may be altered by, for example, using alternate cell types, coupling ligands to the exosome after purification, or putting protein receptors on the surface of exosomes by coupling them to exosome-targeting cytoplasmic domains (LAMP2b, C1C2, myristoylation).

The use of receptors to target exosomes to new tissues has been shown in mouse (Ohno, Mol. Ther., 2013, 21:185; and Alvarez-Erviti, Nat. Biotech, 2011, 29:341-345, herein incorporated by reference in their entirety). Targeted exosomes may be engineered by, for example, using RVG peptides which may cause exosome to target to the brain (Alvarez-Erviti et al., Nat Biotechnol 29, 341 (2011)). RVD motif may target immune cells. Exosome distribution after injuries that mimic disease states (such as cerebral ischaemia or heart reperfusion) may also be tested, as these may change endothelial escape and tissue permeability (Kanasty, Dorkin, Vegas, Anderson, Nature materials 12, 967 (2013)).

In certain embodiments, it may be possible to modify the surface of exosomes with different receptors, such as RVG peptides, dopamine (to dopaminergic cells affected in Parkinson's disease), or heavy chain of botulinum toxin to target motor neurons. These may be adsorbed to the surface of exosomes, or covalently attached by generating versions with active chemical groups for coupling to proteins on the exosome surface.

Example 6: Additional Nucleic Acid Construct Designs for Exosomal Packaging of Gene Silencing Nucleic Acids In certain embodiments, there are provided herein nucleic acid constructs comprising a gene silencing nucleic acid or other nucleic acid sequence of interest incorporated within a pre-miR-451 structural mimic. As will be understood, pre-miR-451 structural mimics may include any of a variety of suitable nucleic acid constructs which may vary from pre-miR-451 in terms of sequence, length, and/or secondary structure, or other characteristic(s), so long as exosomal packaging is maintained.

In the following studies, various different aspects of pre-miR-451 structural mimic design were investigated. Parameters studied include overall stem length, loop length, and the presence of mismatch nucleotide(s) in the stem. Results indicate that a variety of modifications may be made while still providing for exosomal enrichment.

In the following experiments, pre-miR-451 constructs were designed with 10 mutations/modifications testing various properties of the pre-miR-451 backbone. Importantly, these studies indicate that several changes in the backbone structure may be accommodated while still providing for robust packaging into exosomes. Expansion in backbone loop-length, and extension of the overall length of the stem-loop portion, were both tolerated. While some modifications tested were somewhat less efficiently packaged under the experimental conditions used than WT pre-miR-451 constructs, exosomal fold enrichments were still in the range of about 200-fold in many cases. In some examples, fold-enrichment exceeding that of WT was observed (FIG. 8).

Figure 8:
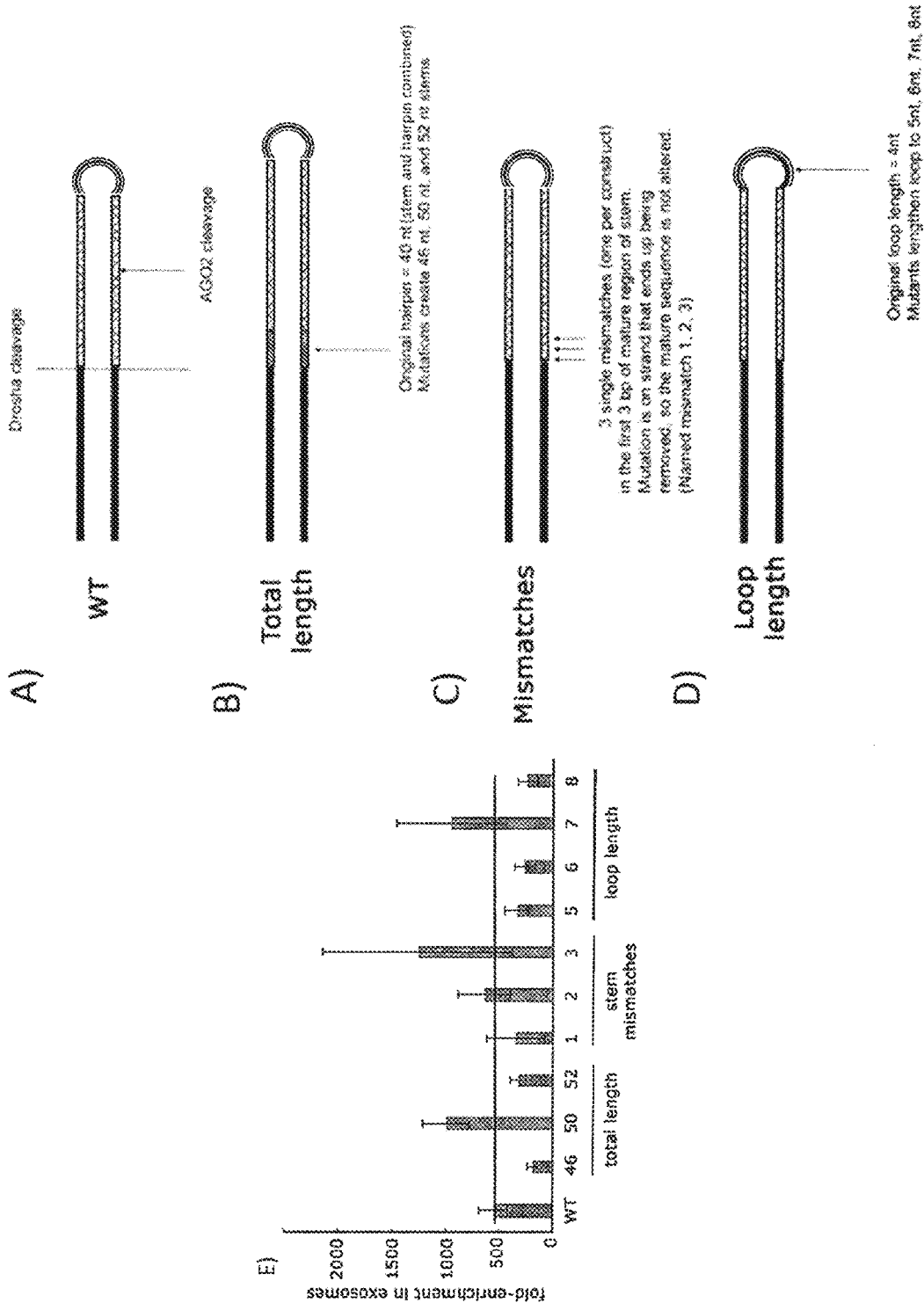
FIG. 8 shows the nucleic acid stem-loop backbone may be altered in total length, stem base-pairing, and/or loop length while still allowing for enrichment of a nucleic acid of interest (in this example, siRNA) in exosomes under the conditions tested. Plasmids encoding pre-miR-451 stem-loop backbone with inserted GFP siRNA were mutated from wild type (WT) (shown in A) to lengthen the stem (B), the loop (D), and to interrupt base-pairing in the stem (C), as shown. These plasmids were transfected into cells, and exosomes were purified two to three days later and RT-qPCR was performed. Abundance of GFP siRNA normalized to miR-16 and let-7a in exosomes was quantified (fold-enrichment), results are shown in (E)

The constructs tested, and exosomal fold-enrichments obtained therefrom, are shown in FIG. 8. The WT construct is graphically depicted in FIG. 8(A).

Overall Length of the Stem (FIG. 8(B)):

The stem portion of the WT structure was extended to provide an overall length of 46, 50, or 52 nt (WT was 40 nt, stem and loop combined). As shown FIG. 8(E), these stem extension constructs showed similar enrichment of inserted siRNA as the WT miR-451 construct. Under the conditions tested, the 46 and 52 nt stem extension constructs provided less enrichment than WT, but still produced robust exosomal enrichment. The 50 nt stem extension construct provided exosomal enrichment which was great than WT under the conditions tested.

Length of the Loop (FIG. 8(D):

The loop section of the WT construct was expanded from 4 nt in the WT up to 8 nt (i.e. 4 nt, 5 nt, 6 nt, 7 nt, and 8 nt loop lengths were tested). As shown in FIG. 8(E), these loop extension constructs showed similar enrichment of inserted siRNA as the WT miR-451 construct. Under the conditions tested, 5 nt, 6 nt, and 8 nt loop extensions provided somewhat less enrichment than WT, but still produced robust exosomal enrichment. The 7 nt loop extension results suggest that this construct provided comparable or perhaps better exosomal enrichment versus WT under the conditions tested. Together, these results indicate that extension of the loop up to at least 8 nt still results in excellent exosomal packaging.

Mismatched Nucleotides in the Stemloop (FIG. 8(C)):

The stem loop section of the WT construct was modified to include 3 different base pair mismatches in the stem portion of the WT miR-451 construct. Three different constructs were developed, each including a single bp mismatch in one of the first 3 basepairs (labeled as positions "1", "2", and "3") of the mature region of the stem as shown. The mutations were positioned on the strand which is removed following AGO2 cleavage, such that the mature targeting sequence was not altered by the designs. As shown in FIG. 8(E), these mismatch constructs showed similar enrichment of inserted siRNA as the WT miR-451 construct. Under the conditions tested, the mismatch at positions "2" and "3" provided comparable, or perhaps better, exosomal enrichment versus WT, and the mismatch at "1" still provided strong enrichment under the conditions tested.

Example 7: Further Structural Modification of Nucleic Acid Constructs for Exosomal Packaging In certain embodiments, there are provided herein nucleic acid constructs comprising a gene silencing nucleic acid or other nucleic acid sequence of interest incorporated within a pre-miR-451 structural mimic. As will be understood, pre-miR-451 structural mimics may include any of a variety of suitable nucleic acid constructs which may vary from pre-miR-451 in terms of sequence, length, and/or secondary structure, or other characteristic(s), so long as exosomal packaging is maintained.

Without wishing to be bound by theory, formation of mature miR-451 is believed to involve Drosha cleavage, Ago2 cleavage, and cleavage by exonucleases removing the final nucleotides from the 3' end. Experiments were thus performed to further investigate exosomal packaging of constructs mimicking various stages of these processing events, and in particular to determine whether exosomal enrichment is dependent on AGO2 binding and/or cleavage. Results obtained indicate that exosomal enrichment may be independent of AGO2, as it can still be observed in Ago2 knockout cells.

Figure 9:
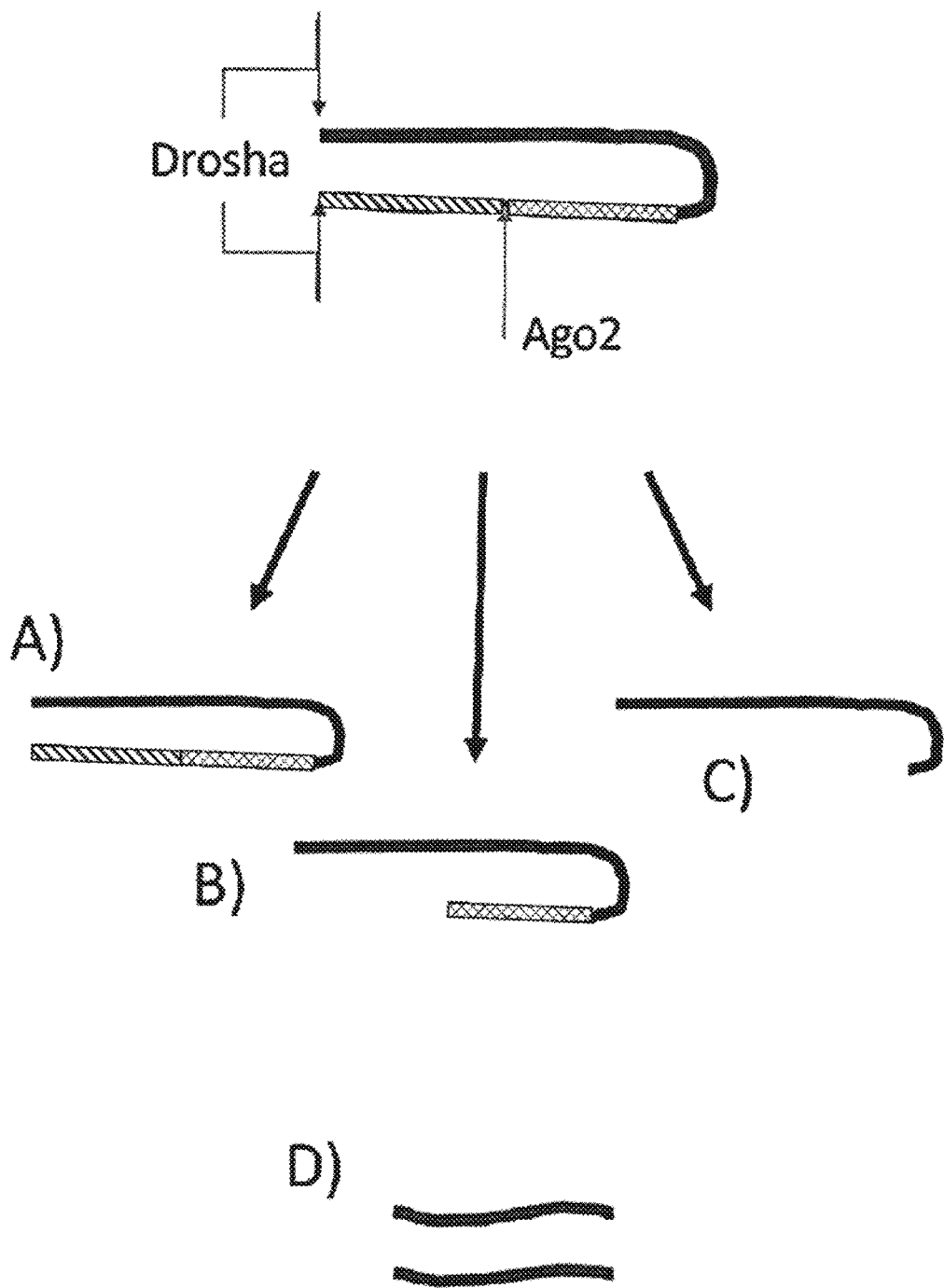
FIG. 9 shows that RNA derivatives of miR-451, mimicking various processing stages, may provide for enrichment of integrated nucleic acid of interest (in this example, siRNA) in exosomes more efficiently than traditional double stranded siRNA with 3' overhangs. Synthetic RNA constructs mimicking WT pre-miR-451 at various processing stages were tested for exosomal enrichment. Constructs were transfected into cells, and exosome enrichment was measured by RT-qPCR after exosome purification by differential centrifugation. miR-451 derived mature siRNA was normalized to levels of let-7a and miR-16 in exosomes vs. cells. Constructs tested include WT pre-mIR-451 construct following Drosha processing (A), an Ago2-cleaved version of the construct (B), and a mature 22 nt miR-451 (post exonuclease activity, having a 5' targeting portion including a portion of the loop region) (C). For comparison, a standard 21 nt dsRNA siRNA with 3' overhangs (D) was also tested. Exosomal enrichment results are shown in (E)
Figure 9:
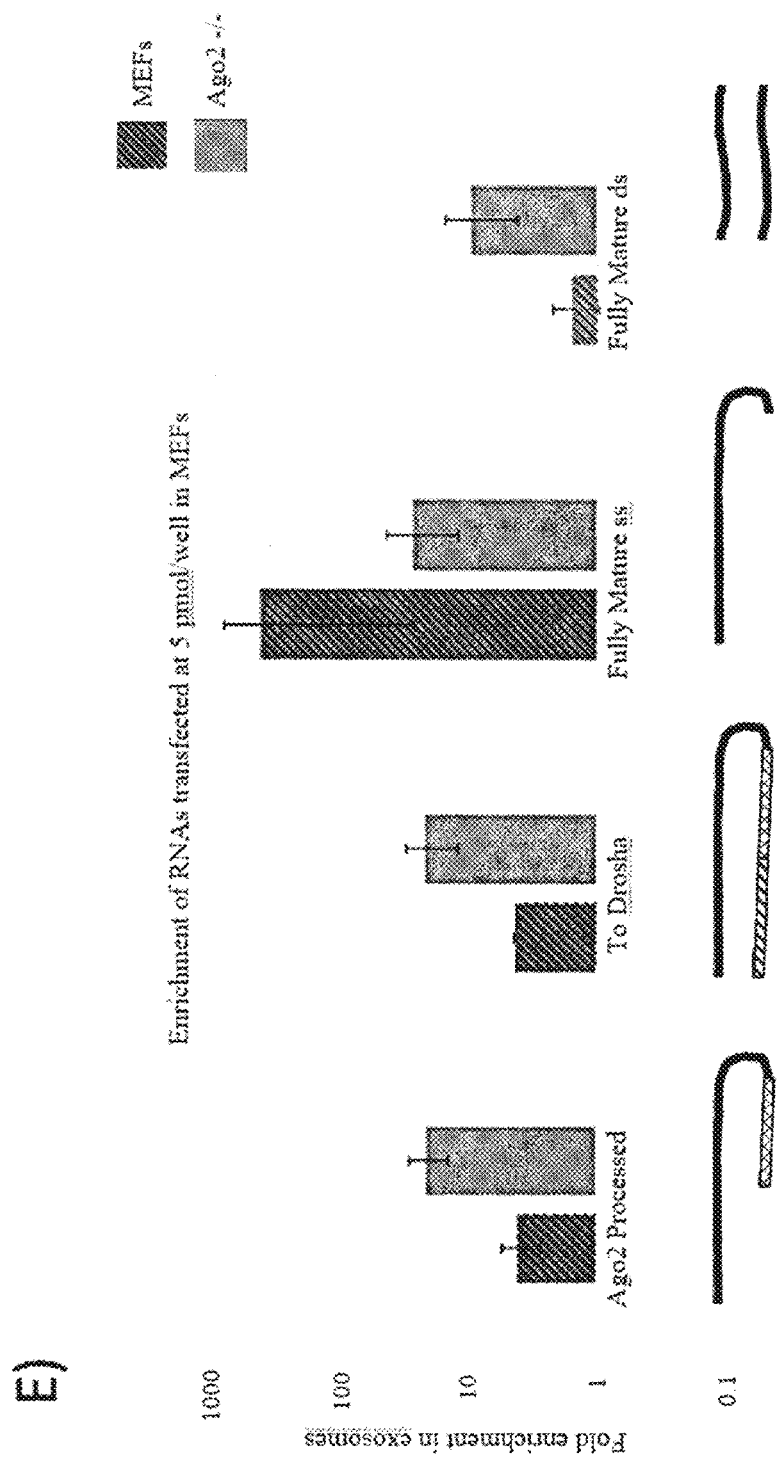

Constructs were accordingly designed which mimic WT pre-miR-451 at various processing stages, and tested for exosomal enrichment. Constructs tested are graphically depicted in FIG. 9. A WT pre-mIR-451 construct following Drosha processing is shown in FIG. 9(A), an Ago2-cleaved version of the construct is shown in FIG. 9(B), and a mature 22 nt miR-451 (post exonuclease activity, having a 5' targeting portion including a portion of the loop region) is shown in FIG. 9(C). For comparison, a standard 21 nt dsRNA siRNA with 3' overhangs (FIG. 9(D)) was also tested. Exosomal enrichment results are shown in FIG. 9(E).

The results indicate that, under the conditions tested, RNA nucleic acids resembling the mature stage (FIG. 9(C)), in which loop-derived sequence is remaining on a single stranded RNA of 22 nt (labelled fully mature ss in FIG. 8(E)), was the most strongly exosome-enriched construct. Notably, the enrichment of ssRNA with loop (FIG. 9(C) construct) was higher than dsRNA resembling classical siRNA with 3' overhangs. These results suggest that single-stranded RNAs may be favored for packaging into exosomes, particularly with slightly longer lengths (i.e. 22-35 nt, vs. 19-21 nt, for example). Further, results suggest that the presence of base-pairing on the 3' end of ssRNA may favor packaging into exosomes. Without wishing to be bound by theory, such base-pairing on the 3' end may facilitate packaging into exosomes by blocking binding of complementary RNA to the targeting RNA sequence. This complementary nucleic acid could be a target mRNA, or any other complementary nucleic acid such as the passenger strand of classical siRNA.

Example 8: Further Cell Lines for Production of Exosomes Containing Nucleic Acids of Interest Studies were conducted to identify further examples of cell types in which pre-miR-451 based constructs may be used to provide exosomes enriched with a nucleic acid of interest. Cell types were tested for their ability to enrich siRNA in exosomes using a pre-miR-451 structural mimic construct using two methods.

Firstly, enrichment of endogenously expressed miR-451 in exosomes was compared to other endogenously expressed microRNAs (miR-16, let-7a). In all testing performed, cell lines identified as demonstrating miR-451 enrichment in exosomes also demonstrated exosomal enrichment of pre-miR-451 structural mimic constructs carrying a nucleic acid of interest. These results suggest that cell lines which produce miR-451 enriched exosomes may serve as exosome-producing cells for the purpose of producing exosome or exosome-like vesicles enriched with a nucleic acid sequence of interest using methods as described herein.

Secondly, a foreign siRNA (typically targeting GFP or SOD1) was inserted into a pre-miR-451 structural mimic, and ability to enrich in exosomes was tested and compared to the same siRNA inserted in a pre-miR-16 structural mimic for comparison.

Results indicate that a wide variety of primary cells and cell lines work to enrich siRNA in exosomes using methods as described herein. The cell lines tested for miR-451 enrichment in exosomes include: primary human mesenchymal stem cells, primary mouse macrophages, human breast cancer cell line (MDA-MB-231), mouse and human neuronal cell lines (Neuro2a, SHSY), mouse astrocyte cell lines (C8 Da, SIM), mouse microglia cell lines (BV2), mouse motor neuron cell lines (NSC-34, MN-1), HeLa, mouse embryonic fibroblasts, and mouse dendritic cells (JAWS II). In each cell line tested, if miR-451 was enriched endogenously in exosomes, then siRNAs inserted in a pre-miR-451 structural mimic construct also resulted in exosomal enrichment. These results indicate that enrichment of endogenous miR-451 in exosomes may be a diagnostic or indicator of a candidate cell line effective for enriching siRNA in exosomes using methods as described herein.

All cell types tested, with the exception of human embryonic stem cells, produced strong exosomal enrichment. Results are provided in Table I below.

TABLE 1

Exosomal enrichment of miR-451 in various cell types.
Exosomes from the indicated cell lines grown in
exosome-depleted media or in serum-free media were
purified and miR-451, miR-16, and let-7a were
quantified by RT-qPCR in exosomes and
exosome-producing cells.

| Cell type | Enrichment of miR-451 in exosomes/cell (vs. miR-16 and let-7a) |
|---|---|
| MEF | 68800 |
| JAWSII | 23642 |
| MDA | 5600 |
| MSC Line | 5293 |
| Primary MSC | 702 |
| ESC | 3 |
| N2A | 4119 |
| Macrophage | 1280 |
| BV2 | 1887 |
| MN1 | 44 |
| NSC34 | 73 |
| C8D1A | 40 |
| C8S | 383 |
| C8D30 | 22 |

Example 9: Cellular Factors Affecting Exosomal Enrichment

A variety of cellular factors which may affect nucleic acid construct packaging in exosomes using methods as described herein were studied. Specifically, effects of overexpression of mutant Ras, mutant Myc, wild-type Ago2, and siRNA depletion of Translin were studied. In the results obtained, none of these factors had a significant effect on construct (in this example, an siRNA-containing construct) enrichment in exosomes, suggesting that the system does not rely on oncogenic factors. The effect of several drugs was also tested, such as mTOR inhibitors and lysosomal/autophagy inhibitors which are clinically used. Results indicated that mTOR inhibitors had no effect on miR-451 enrichment in exosomes, while lysosomal/autophagy inhibitors increased exosome number, suggesting that such inhibitors may be used to enhance manufacturing of exosomes for drug delivery. Lysosomal/autophagy inhibitors tested include Bafilomycin A1, concanamycin, and NAADP-AM.

Testing of the effect of Ago2 on enrichment of siRNA-containing constructs in exosomes using pre-miR-451 structural mimics as described herein was also performed. Results indicate that siRNA targeting TetR inserted in a pre-miR-451 structural mimic was still enriched in exosomes in Ago2 knockout mouse embryonic fibroblasts (compared to wild-type cells, or Ago2 knockout cells rescued with wild-type Ago2 or catalytically dead Ago2). In addition, results indicate that constructs were further enriched in exosomes when Ago2 was depleted, or catalytically inactivated. These results suggest that exosomal packaging methods as described herein may be enhanced by inhibition of expression or activity of Ago2, and/or by utilizing exosome-producing cells with less or less-active Ago2.

Figure 10:
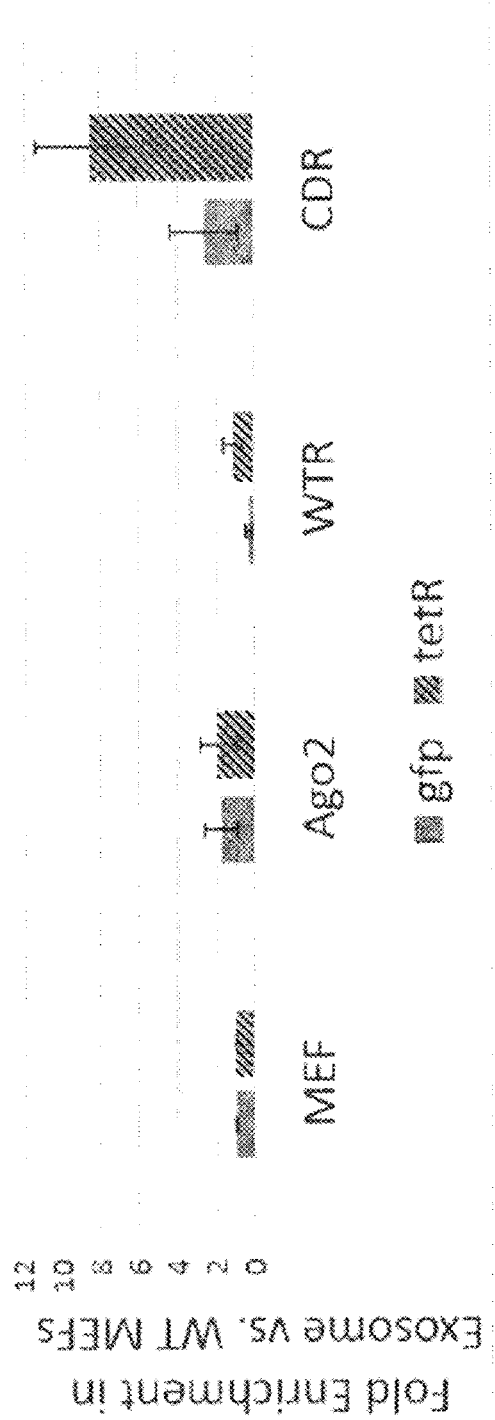
FIG. 10 shows that Ago2 inhibits, to an extent, packaging of siRNA-containing constructs based on pre-mIR-451 structural mimics into exosomes. In these experiments, plasmids including siRNA sequences targeting GFP or TctR integrated in a pre-miR-451 structural mimic were transfected into cells, and the levels of GFP or TetR siRNA in exosomes vs cells (vs. let-7a and miR-16 in exosomes/cells) was measured by qRT-PCR two to three days later. Enrichment of miR-451 derived sequences in exosomes was normalized to 1 for wild-type exosomes. X-axis shows cell types tested (MEF [mouse embryonic fibroblasts], Ago2 knockout MEF, WTR [Ago2 knockout MEF rescued with wild-type Ago2], and CDR (Ago2 knockout MEF rescued with catalytically dead Ago2)

Experimental results of this testing are shown in FIG. 10. This data suggests that Ago2 may, to an extent, inhibit packaging of siRNA-containing constructs based on pre-miR-451 structural mimics into exosomes. In these experiments, plasmids including siRNA sequences targeting GFP or TetR integrated in a pre-miR-451 structural mimic were transfected into cells, and the levels of GFP or TetR siRNA in exosomes vs cells (vs. let-7a and miR-16 in exosomes/cells) was measured by qRT-PCR two to three days later. Enrichment of miR-451 derived sequences in exosomes was normalized to 1 for wild-type exosomes. X-axis shows cell types tested (MEF [mouse embryonic fibroblasts], Ago2 knockout MEF, WTR [Ago2 knockout MEF rescued with wild-type Ago2], and CDR (Ago2 knockout MEF rescued with catalytically dead Ago2).

Example 10: Exosomal Enrichment of a Variety of Different Nucleic Acid Sequences of Interest In studies described herein, a variety of different siRNAs targeting GFP, SOD1, and Tet Repressor (each having different sequences unrelated to miR-451) have been incorporated into pre-miR-451 structural mimics and subsequently enriched in exosomes using methods as described herein. These results, in addition to previous testing using multiple independent microRNAs incorporated into pre-miR-451 structural mimics including miR-106, miR-199-5p, and miR-155 (previously described hereinabove) demonstrate that the methods and constructs as described herein are highly tolerant toward sequence variation, and indicate that these constructs and methods may be used to accommodate a wide variety of nucleic acid sequences of interest.

Example 11: Expression Vectors for Pre-miR-451 Structural Mimics

Results provided herein demonstrate that pre-miR-451 structural mimic constructs may be delivered to, or expressed in, cells using a variety of different techniques while still providing enriched exosomal packaging.

In certain examples, pre-miR-451 structural mimic constructs may be expressed in cells using expression vectors. In this regard, a variety of different promoters and vectors (i.e. Chicken beta-actin enhancer-CMV [CAG], CMV, U6, IRES, plasmid or lentiviral constructs) have been tested. Testing was also performed to investigate whether nucleic acid sequences of interest (in this example, siRNAs) were are enriched in exosomes when the pre-miR-451 structural mimic construct was delivered as a RNA rather than DNA expression vector (see above). Moreover, testing of RNA mimics (and presumably DNA expression constructs) that produce derivatives of pre-miR-451 including a long RNA including a pre-miR-451-like sequence, Drosha processed, Ago2 processed or mature miR-451-like sequences with small amounts of base-pairing or stem structures in the 3' end, or slightly longer than normal siRNA (22-35 nt), suggests that such constructs are all packaged robustly into exosomes under the conditions tested. These findings suggest that pre-miR-451 structural mimic constructs, or its derivatives, may be expressed or delivered in a wide variety of contexts while still providing for enrichment of inserted nucleic acid sequences of interest into exosomes.

Example 12: Gene Silencing in Mouse Brain by Exosomes Loaded with SOD1 Silencing RNA Generated Using a Pre-miR-451 Structural Mimic Exosomes loaded with SOD1 silencing RNA generated using a pre-miR-451 structural mimic according to methods as described herein were used to silence expression of SOD1 in an in vivo mouse system. In these experiments, under the conditions tested, SOD1 silencing RNA-loaded exosomes were observed to reduce expression of SOD1 in the mouse brain by about 30-50% in some cases, as measured by RT-qPCR or quantitative FISH.

Figure 11:
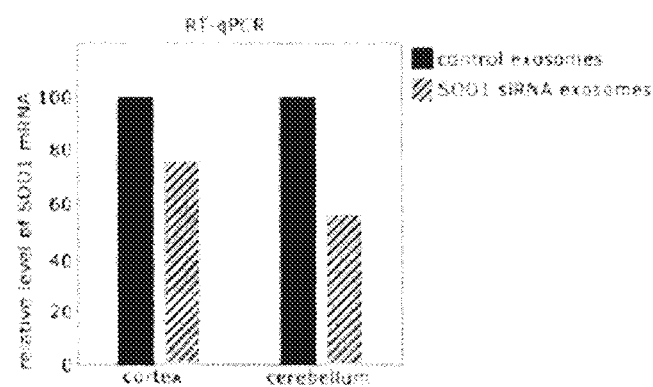
FIG. 11 shows gene silencing in mouse brain by exosomes loaded with SOD1 silencing RNA generated using a pre-miR-451 structural mimic. NSC-34 mouse motor neuron cell lines was transduced with lentiviral vectors expressing SOD1 silencing RNA incorporated in a pre-miR-451 backbone. 5 µg of exosomes were injected into the intracerebroventicular space of human G93A SOD1 transgenic mice and two days later mice were euthanized. Tissues were flash frozen and processed for RT-qPCR and FISH. (A) RT-qPCR analysis using Taqman probes to quantify SOD relative to controls (β-actin and TBP) in cortex and cerebellum. (B) Cortical tissues from mice were processed for FISH analysis of SOD1 siRNA (Exiqon microRNA ISH, GADPH mRNA (Stellaris probe Quasar 670), human SOD1 mRNA (Stellaris probe Quasar 570). Representative epifluorescence images are shown. (C) Quantification of SOD1 mRNA signal intensity relative to GAPDH signal intensity over 4-8 images of cortex from mice injected with exosomes packaged with silencing RNA targeting SOD1.
Figure 11:
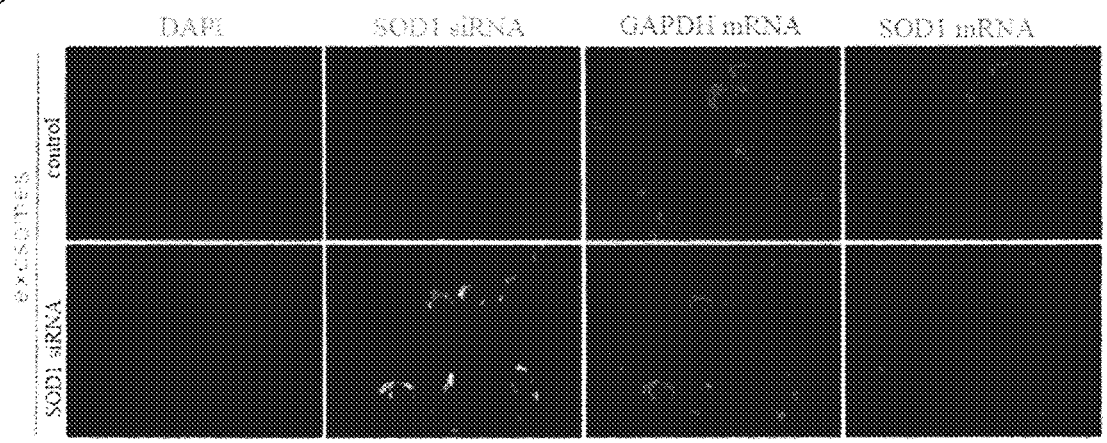
Figure 11:
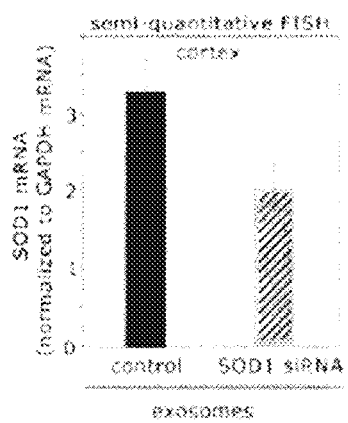

Results of these studies are provided in FIG. 11. NSC-34 mouse motor neuron cell lines was transduced with lentiviral vectors expressing SOD1 silencing RNA incorporated in a pre-miR-451 backbone. 5 μg of exosomes were injected into the intracerebroventicular space of human G93A SOD1 transgenic mice and two days later mice were euthanized. Tissues were flash frozen and processed for RT-qPCR and FISH.

FIG. 11(A) shows RT-qPCR analysis using Taqman probes to quantify SOD1 relative to controls (β-actin and TBP) in cortex and cerebellum. In both the cortex and cerebellum, a reduction in SOD1 mRNA levels was observed using the SOD1 silencing RNA-loaded exosomes as compared to control exosomes.

In FIG. 11(B), cortical tissues from mice were processed for FISH analysis of SOD1 siRNA (Exiqon microRNA ISH, GADPH mRNA (Stellaris probe Quasar 670), human SOD1 mRNA (Stellaris probe Quasar 570). Represenative epifluorescence images are shown in FIG. 11(B). DAPI (blue) is shown in the $1^{st}$ column, SOD1 siRNA (green) is shown in the second column, GAPDH mRNA (purple) is shown in the $3^{rd}$ column, and SOD1 mRNA (red) is shown in the $4^{th}$ column.

FIG. 11(C) provides quantification of SOD1 mRNA signal intensity relative to GAPDH signal intensity over 4-8 images of cortex from mice injected with exosomes packaged with silencing RNA targeting SOD1. As shown, a reduction in SOD1 mRNA levels was observed using the SOD silencing RNA-loaded exosomes as compared to control exosomes.

The sequence of the pre-miR-451 structural mimic targeting SOD1 was:

```
                                        (SEQ ID NO: 17)
5'-CUUGGGAAUGGCAAGGUUCAGUCAGUCCUUUAAUGCUUUUUAAAGG
ACUGACUGACUCUUGCUAUACCCAGA-3'
```

These sequences include the sequence of pre-mir-451 up to the drosha cleavage site. They were inserted into the GIPZ vector in place of the shRNA downstream of the IRES. The GIPZ sequence is shown in FIG. 13 as SEQ ID NO: 18. The pGIPZ sequence is:

```
>pGIPZ
tggaagggctaattcactcccaaagaagacaagatatccttgatctgtgg atctaccacacacaaggctacttccctgattagcagaactacacaccagg gccagggctcagatatccactgacctttggatggtgctacaagctagtac cagttgagccagataaggtagaagaggccaataaaggagagaacaccagc ttgttacaccctgtgagcctgcatgggatggatgacccgagagagaagt gttagagtggaggtttgacagccgcctagcatttcatcacgtggcccgag agctgcatccggagtacttcaagaactgctgatatcgagcttgctacaag ggactttccgctggggactttccaggggaggcgtggcctgggcgggactgg ggagtggcgagccctcagatcctgcatataagcagctgcttttttgcctgt actgggtctctctggttagaccagatctgagcctgggagctctctggcta actagggaacccactgcttaagcctcaataaagcttgccttgagtgcttc aagtagtgtgtgcccgtctgttgtgtgactctggtaactagagatccctc
```

-continued
```
agaccctttagtcagtgtggaaaatctctagcagtggcgcccgaacagg gacttgaaagcgaaagggaaaccagaggagctctctcgacgcaggactcg gcttgctgaagcgcgcacggcaagaggcgaggggcggcgactggtgagta cgccaaaaattttgactagcggaggctagaaggagagagatgggtgcgag agcgtcagtattaagcgggggagaattagatcgcgatgggaaaaaattcg gttaaggccaggggaaagaaaaaatataaattaaaacatatagtatggg caagcagggagctagaacgattcgcagttaatcctggcctgttagaaaca tcagaaggctgtagacaaatactgggacagctacaaccatcccttcagac aggatcagaagaacttagatcattatataatacagtagcaaccctctatt gtgtgcatcaaaggatagagataaaagacaccaaggaagctttagacaag atagaggaagagcaaaacaaaagtaagaccaccgcacagcaagcggccgg ccgctgatcttcagacctggaggaggagatatgagggacaattggagaag tgaattatataaatataaagtagtaaaaattgaaccattagaagtagcac ccaccaaggcaaagagaagagtggtgcagagagaaaaaagagcagtggga ataggagctttgttccttgggttcttgggagcagcaggaagcactatggg cgcagcgtcaatgacgctgacggtacaggccagacaattattgtctggta tagtgcagcagcagaacaatttgctgagggctattgaggcgcaacagcat ctgttgcaactcacagtctggggcatcaagcagctccaggcaagaatcct ggctgtggaaagataccctaaaggatcaacagctcctggggatttggggtt gctctggaaaactcatttgcaccactgctgtgccttggaatgctagttgg agtaataaatctctggaacagatttggaatcacacgacctggatggagtg ggacagagaaattaacaattacacaagcttaatacactccttaattgaag aatcgcaaaaccagcaagaaaagaatgaacaagaattattggaattagat aaatgggcaagtttgtggaattggtttaacataacaaattggctgtggta tataaaattattcataatgatagtaggaggcttggtaggtttaagaatag tttttgctgtactttctatagtgaatagagttaggcagggatattcacca ttatcgtttcagacccacctcccaaccccgaggggacccgacaggcccga aggaatagaagaagaaggtggagagagagacagagacagatccattcgat tagtgaacggatcggcactgcgtgcgccaattctgcagacaaatggcagt attcatccacaattttaaaagaaaaggggggattgggggtacagtgcag gggaaagaatagtagacataatagcaacagacatacaaactaaagaatta caaaaacaaattacaaaaattcaaaattttcgggtttattacagggacag cagagatccagtttggttagtaccgggcccgctctagtccggaatcagtc ctgctcctcggccacgaagtgcacgcagttgccggccgggtcgcgcaggg cgaactcccgcccccacggctgctcgccgatctcggtcatggccggcccg gaggcgtcccggaagttcgtggacacgacctccgaccactcggcgtacag ctcgtccaggccgcgcacccacacccaggccagggtgttgtccggcacca cctggtcctggaccgcgctgatgaacagggtcacgtcgtcccggaccaca ccggcgaagtcgtcctccacgaagtcccgggagaacccgagccggtcgt ccagaactcgaccgctccggcgacgtcgcgcgcggtgagcaccggaacgg cactggtcaacttggccatggtggccctcctatagtgagtcgtattatac
```

-continued tatgccgatatactatgccgatgattaattgtcaacacgtgctgcaggtc
cgaggttctagacgtattaccgccatgcattagttattaatagtaatcaa
ttacggggtcattagttcatagcccatatatggagttccgcgttacataa
cttacggtaaatggcccgcctggctgaccgccaacgaccccgcccatt
gacgtcaataatgacgtatgttcccatagtaacgccaatagggactttcc
attgacgtcaatgggtggagtatttacggtaaactgcccacttggcagta
catcaagtgtatcatatgccaagtacgccccctattgacgtcaatgacgg
taaatggcccgcctggcattatgcccagtacatgaccttatgggactttc
ctacttggcagtacatctacgtattagtcatcgctattaccatggtgatg
cggttttggcagtacatcaatgggcgtggatagcggtttgactcacgggg
atttccaagtctccaccccattgacgtcaatgggagtttgttttggcacc
aaaatcaacgggactttccaaaatgtcgtaacaactccgccccattgacg
caaatgggcggtaggcgtgtacggtgggaggtctatataagcagagctcg
tttagtgaaccgtcagatcgcctggagacgccatccacgctgttttgacc
tccatagaagacaccgactctactagaggatctgccaccatggagagcga
cgagagcggcctgcccgccatggagatcgagtccgcatcaccggcaccc
tgaacggcgtggagttcgagctggtgggcggcggagagggcacccccgag
cagggccgcatgaccaacaagatgaagagcaccaaaggcgccctgacctt
cagcccctacctgctgagccacgtgatgggctacggcttctaccacttcg
gcacctaccccagcggctacgagaaccccttcctgcacgccatcaacaac
ggcggctacaccaacacccgcatcgagaagtacgaggacggcggcgtgct
gcacgtgagcttcagctaccgctacgaggccggccgcgtgatcggcgact
tcaaggtgatgggcaccggcttccccgaggacagcgtgatcttcaccgac
aagatcatccgcagcaacgccaccgtggagcacctgcaccccatgggcga
taacgatctggatggcagcttcacccgcaccttcagcctgcgcgacggcg
gctactacagctccgtggtggacagccacatgcacttcaagagcgccatc
caccccagcatcctgcagaacgggggccccatgttcgccttccgccgcgt
ggaggaggatcacagcaacaccgagctgggcatcgtggagtaccagcacg
ccttcaagacccccgatgcagatgccggtgaagaataatgtacaagtagc
ggccgcaaattccgcccctctccctccccccccctaacgttactggccg
aagccgcttggaataaggccggtgtgcgtttgtctatatgttattttcca
ccatattgccgtcttttggcaatgtgagggcccggaaacctggccctgtc
ttcttgacgagcattcctaggggtcttcccctctcgccaaaggaatgca
aggtctgttgaatgtcgtgaaggaagcagttcctctggaagcttcttgaa
gacaaacaacgtctgtagcgacccctttgcaggcagcggaacccccacct
ggcgacaggtgcctctgcggccaaaagccacgtgtataagatacacctgc
aaaggcggcacaaccccagtgccacgttgtgagttggatagttgtggaaa
gagtcaaatggctctcctcaagcgtattcaacaaggggctgaaggatgcc
cagaaggtaccccattgtatggatctgatctggggcctcggtgcacatg
ctttacatgtgtttagtcgaggttaaaaaaacgtctaggccccccgaacc -continued acggggacgtggttttcctttgaaaaacacgataataccatggccaccga
gtacaagcccacggtgcgcctcgccaccgcgacgacgtccccggggccg
tacgcaccctcgccgccgcgttcgccgactaccccgccacgcgccacacc
gtcgacccggaccgccacatcgagcgggtcaccgagctgcaagaactctt
cctcacgcgcgtcgggctcgacatcggcaaggtgtgggtcgcggacgacg
gcgccgcggtggcggtctggaccacgccggagagcgtcgaagcgggggcg
gtgttcgccgagatcggctcgcgcatggccgagttgagcggttcccggct
ggccgcgcagcaacagatggaaggcctcctggccgccgcaccggcccaagg
agcccgcgtggttcctggccaccgtcggcgtctcgcccgaccaccagggc
aagggtctgggcagcgccgtcgtgctccccggagtggaggcggccgagcg
cgctggggtgcccgccttcctggagacctccgcgccccgcaacctcccct
tctacgagcggctcggcttcaccgtcaccgccgacgtcgaggtgcccgaa
ggaccgcgcacctggtgcatgacccgcaagcccggtgcctgagtttgttt
gaatgaggcttcagtactttacagaatcgttgcctgcacatcttggaaac
acttgctgggattacttcttcaggttaacccaacagaaggctcgaggtaa
ccggatcctgatcagaattcaaggggctactttaggagcaattatcttgt
ttactaaaactgaataccttgctatctctttgatacatttttacaaagct
gaattaaaatggtataaattaaatcacttttttcaattggaagactaatg
cggccggccattactccgtctcgtgtcttgttgcatatgtctgctggttt
gtttgatgttgtttgcgggcgggccctatagtgagtcgtattacctagga
cgcgtctggaacaatcaacctctggattacaaaatttgtgaaagattgac
tggtattcttaactatgttgctccttttacgctatgtggatacgctgctt
taatgcctttgtatcatgctattgcttcccgtatggctttcattttctcc
tccttgtataaatcctggttgctgtctctttatgaggagttgtggcccgt
tgtcaggcaacgtggcgtggtgtgcactgtgtttgctgacgcaacccca
ctggttggggcattgccaccacctgtcagctcctttccgggactttcgct
ttccccctccctattgccacggcggaactcatcgccgcctgccttgcccg
ctgctggacaggggctcggctgttgggcactgacaattccgtggtgttgt
cggggaagctgacgtccttttccatggctgctcgcctgtgttgccacctgg
attctgcgcgggacgtccttctgctacgtcccttcggccctcaatccagc
ggaccttccttcccgcggcctgctgccggctctgcggcctcttccgcgtc
ttcgccttcgccctcagacgagtcggatctccctttgggccgcctccccg
cctggaattaattctgcagtcgagacctagaaaaacatggagcaatcaca
agtagcaatacagcagctaccaatgctgattgtgcctggctagaagcaca
agaggaggaggaggtgggttttccagtcacacctcaggtacctttaagac
caatgacttacaaggcagctgtagatcttagccacttttaaaagaaaag
aggggactggaagggctaattcactcccaacgaagacaagatctgctttt
tgcttgtactgggtctctctggttagaccagatctgagcctgggagctct
ctggctaactagggaacccactgcttaagcctcaataaagcttgccttga
gtgcttcaagtagtgtgtgcccgtctgttgtgtgactctggtaactagag
atccctcagaccctttagtcagtgtggaaaatctctagcagtagtagtt -continued catgtcatcttattattcagtatttataacttgcaaagaaatgaatatca
gagagtgagaggccttgacattgtttaaacccgctgatcagcctcgactg
tgccttctagttgccagccatctgttgtttgcccctcccccgtgccttcc
ttgaccctggaaggtgccactcccactgtcctttcctaataaaatgagga
aattgcatcgcattgtctgagtaggtgtcattctattctgggggggtgggg
tggggcaggacagcaaggggaggattgggaagacaatagcaggcatgct
ggggatgcggtgggctctatggcttctgaggcggaaagaaccagctgggg
ctctaggggtatccccacgcgccctgtagcggcgcattaagcgcggcgg
gtgtggtggttacgcgcagcgtgaccgctacacttgccagcgccctagcg
cccgctcctttcgctttcttcccttcctttctcgccacgttcgccggctt
tccccgtcaagctctaaatcgggggctccctttagggttccgatttagtg
ctttacggcacctcgacccaaaaaacttgattagggtgatggttcacgt
agtgggccatcgccctgatagacggttttcgccctttgacgttggagtc
cacgttctttaatagtggactcttgttccaaactggaacaacactcaacc
ctatctcggtctattcttttgatttataagggattttgccgatttcggcc
tattggttaaaaaatgagctgatttaacaaaaatttaacgcgaattaatt
ctgtggaatgtgtgtcagttaggggtgtggaaagtccccaggctcccagc
aggcagaagtatgcaaagcatgcatctcaattagtcagcaaccaggtgtg
gaaagtccccaggctccccagcaggcagaagtatgcaaagcatgcatctc
aattagtcagcaaccatagtcccgcccctaactccgcccatcccgcccct
aactccgcccagttccgcccattctccgcccatggctgactaattttttt
ttatttatgcagaggccgaggccgcctctgcctctgagctattccagaag
tagtgaggaggcttttttggaggcctaggcttttgcaaaaagctcccggg
agcttgtatatccattttcggatctgatcagcacgtgatgaaaaagcctg
aactcaccgcgacgtctgtcgagaagtttctgatcgaaaagttcgacagc
gtctccgacctgatgcagctctcggasggcgaagaatctcgtgctttcag
cttcgatgtaggagggcgtggatatgtcctgcgggtaaatagctgcgccg
atggtttctacaaagatcgttatgtttatcggcactttgcatcggccgcg
ctcccgattccggaagtgcttgacattggggaattcagcgagagcctgac
ctattgcatctcccgccgtgcacagggtgtcacgttgcaagacctgcctg
aaaccgaactgcccgctgttctgcagccggtcgcggaggccatggatgcg
atcgctgcggccgatcttagccagacgagcgggttcggcccattcggacc
gcaaggaatcggtcaatacactacatggcgtgatttcatatgcgcgattg
ctgatccccatgtgtatcactggcaaactgtgatggacgacaccgtcagt
gcgtccgtcgcgcaggctctcgatgagctgatgctttgggccgaggactg
ccccgaagtccggcacctcgtgcacgcggatttcggctccaacaatgtcc
tgacggacaatggccgcataacagcggtcattgactggagcgaggcgatg
ttcggggattcccaatacgaggtcgccaacatcttcttctggaggccgtg
gttggcttgtatggagcagcagacgcgctacttcgagcggaggcatccgg
agcttgcaggatcgccgcggctccgggcgtatatgctccgcattggtctt -continued gaccaactctatcagagctggttgacggcaatttcgatgatgcagcttg
ggcgcagggtcgatgcgacgcaatcgtccgatccggagccgggactgtcg
ggcgtacacaaatcgcccgcagaagcgcggccgtctggaccgatggctgt
gtagaagtactcgccgatagtggaaaccgacgccccagcactcgtccgag
ggcaaaggaatagcacgtgctacgagatttcgattccaccgccgccttct
atgaaaggttgggcttcggaatcgttttccgggacgccggctggatgatc
ctccagcgcggggatctcatgctggagttcttcgcccaccccaacttgtt
tattgcagcttataatggttacaaataaagcaatagcatcacaaatttca
caaataaagcatttttttcactgcattctagttgtggtttgtccaaactc
atcaatgtatcttatcatgtctgtataccgtcgacctctagctagagctt
ggcgtaatcatggtcatagctgtttcctgtgtgaaattgttatccgctca
caattccacacaacatacgagccggaagcataaagtgtaaagcctgggt
gcctaatgagtgagctaactcacattaattgcgttgcgctcactgcccgc
tttccagtcgggaaacctgtcgtgccagctgcattaatgaatcggccaac
gcgcggggagaggcggtttgcgtattgggcgctcttccgcttcctcgctc
actgactcgctgcgctcggtcgttcggctgcggcgagcggtatcagctca
ctcaaaggcggtaatacggttatccacagaatcaggggataacgcaggaa
agaacatgtgagcaaaaggccagcaaaaggccaggaaccgtaaaaaggcc
gcgttgctggcgtttttccataggctccgcccccctgacgagcatcacaa
aaatcgacgctcaagtcagaggtggcgaaacccgacaggactataaagat
accaggcgtttccccctggaagctccctcgtgcgctctcctgttccgacc
ctgccgcttaccggatacctgtccgcctttctcccttcgggaagcgtggc
gctttctcatagctcacgctgtaggtatctcagttcggtgtaggtcgttc
gctccaagctgggctgtgtgcacgaaccccccgttcagcccgaccgctgc
gccttatccggtaactatcgtcttaagtccaacccggtaagacacgactt
atcgccactggcagcagccactggtaacaggattagcagagcgaggtatg
taggcggtgctacagagttcttgaagtggtggcctaactacggctacact
agaagaacagtatttggtatctgcgctctgctgaagccagttaccttcgg
aaaaagagttggtagctcttgatccggcaaacaaaccaccgctggtagcg
gtggtttttttgtttgcaagcagcagattacgcgcagaaaaaaaggatct
caagaagatcctttgatcttttctacggggtctgacgctcagtggaacga
aaactcacgttaagggattttggtcatgagattatcaaaaaggatcttca
cctagatccttttaaattaaaaatgaagttttaaatcaatctaaagtata
tatgagtaaacttggtctgacagttaccaatgcttaatcagtgaggcacc
tatctcagcgatctgtctatttcgttcatccatagttgcctgactccccg
tcgtgtagataactacgatacgggagggcttaccatctggccccagtgct
gcaatgataccgcgagacccacgctcaccggctccagatttatcagcaat
aaaccagccagccggaagggccgagcgcagaagtggtcctgcaactttat
ccgcctccatccagtctattaattgttaccgggaagctagagtaagtagt
tcgccagttaatagtttgcgcaacgttgttgccattgctacaggcatcgt
ggtgtcacgctcgtcgtttggtatggcttcattcagctccggttcccaac -continued gatcaaggcgagttacatgatcccccatgttgtgcaaaaaagcggttagc tccttcggtcctccgatcgttgtcagaagtaagttggccgcagtgttatc actcatggttatggcagcactgcataattctcttactgtcatgccatccg taagatgcttttctgtgactggtgagtactcaaccaaatcattctgagaa tagtgtatgcggcgaccgagttgctcttgcccggcgtcaatacgggataa taccgcgccacatagcagaactttaaaagtgctcatcattggaaaacgtt cttcggggcgaaaactctcaaggatcttaccgctgttgagatccagttcg atgtaacccactcgtgcacccaactgatcttcagcatcttttactttcac cagcgtttctgggtgagcaaaaacaggaaggcaaaatgccgcaaaaaagg gaataagggcgacacggaaatgttgaatactcatactcttccttttcaa tattattgaagcatttatcagggttattgtctcatgagcggatacatatt tgaatgtatttagaaaaataaacaaatagggggttccgcgcacatttcccc gaaaagtgccacctgacgtcgacggatcgggagatcaacttgtttattgc agcttataatggttacaaataaagcaatagcatcacaaatttcacaaata aagcatttttttcactgcattctagttgtggtttgtccaaactcatcaat gtatcttatcatgtctggatcaactggataactcaagctaaccaaaatca tcccaaacttcccaccccatccctattaccactgccaattacctgtggt ttcatttactctaaacctgtgattcctctgaattattttcatttaaaga aattgtatttgttaaatatgtactacaaacttagtagt Example 13: Gene Silencing in Select Target Cell Culture Models by Exosomes Loaded with GFP-Targeting siRNA Generated Using a Pre-mIR-451 Structural Mimic Exosomes loaded with GFP-targeting siRNA generated using a pre-mIR-451 structural mimic according to methods as described herein were used to silence GFP gene expression in select target cells. In these experiments, under the conditions tested, GFP-targeting siRNA-loaded exosomes produced from multiple different exosome-producing donor cells were observed to reduce expression of GFP in HeLa cells.

Figure 12:
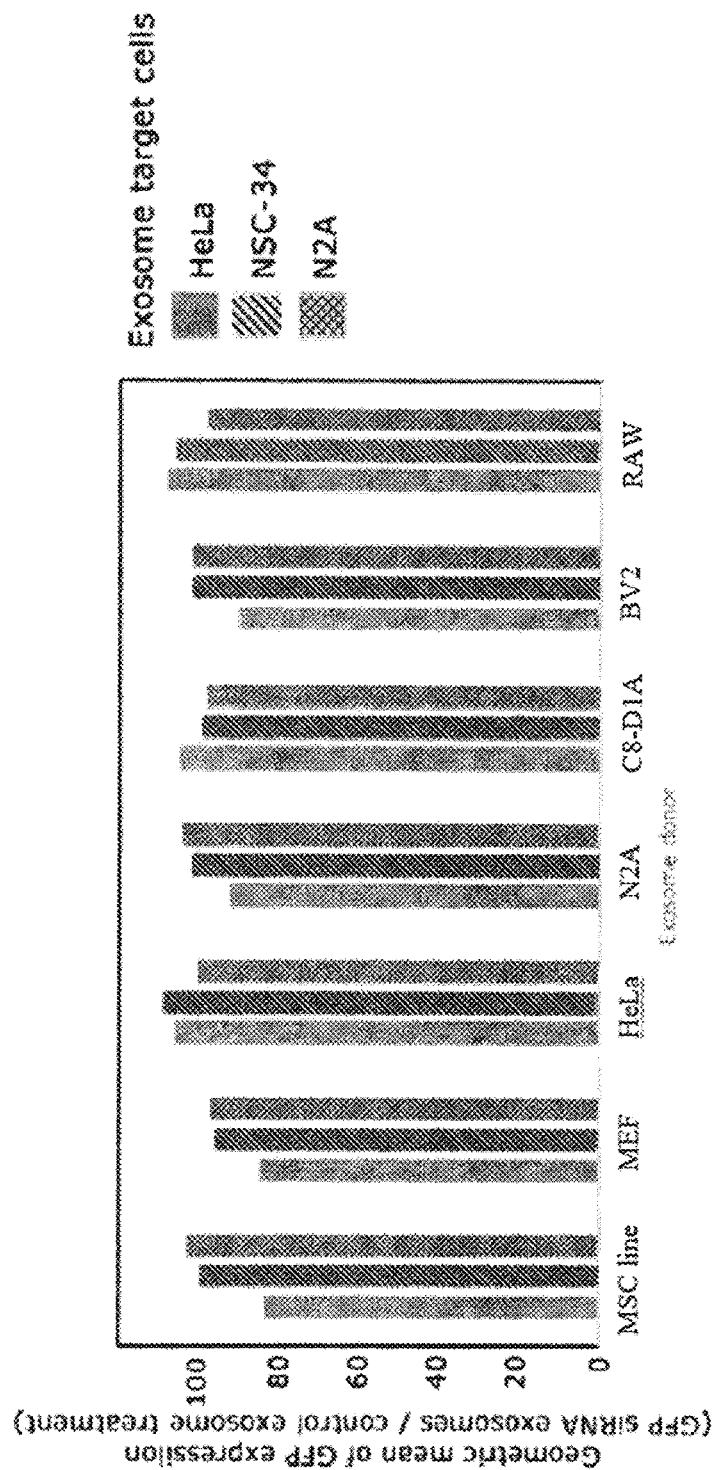
FIG. 12 shows data wherein exosomes loaded with GFP-targeting siRNA generated using a pre-mIR-451 structural mimic reduced expression of GFP in select target cells. Exosomes from exosome-producing donor cells transfected or transduced with constructs expressing GFP siRNA incorporated in a pre-miR-451 structural mimic were incubated with GFP expressing exosome target cells (HeLa, NSC-34 or Neuro2a [N2A]) for 48 h, and GFP expression was analyzed by flow cytometry. GFP expression was reduced in HeLa cells by exosomes containing GFP siRNA produced from multiple different exosome donor cells.

Results of these studies are provided in FIG. 12. Exosomes from exosome-producing donor cells transfected or transduced with constructs expressing GFP siRNA incorporated in a pre-mIR-451 structural mimic were incubated with GFP expressing exosome target cells (HeLa cells, blue, left columns; NSC-34 cells, orange, middle columns; or Neuro2a [N2A] cells, grey, right columns) for 48 h. and GFP expression was analyzed by flow cytometry. As shown, GFP expression was reduced in HeLa cells by exosomes containing GFP targeting siRNA produced from multiple different exosome donor cells. Results suggest that certain of the exosomes tested in these experiments were at least partially selective for HeLa target cells.

The sequence of the pre-miR-451 structural mimic targeting eGFP was:

(SEQ ID NO: 19)
5'-CUUGGGAAUGGCAAGGAUGAACUUCAGGGUCAGCUUGCGCUGACCCU
GAAGUUCAUUCUUGCUAUACCCAGA

The sequence of the pre-miR-451 structural mimic targeting TetR was:

(SEQ ID NO: 20)
5'-CUUGGGAAUGGCAAGGUCUUGAUCUUCCAAUACGCAACCGUAUUGGA
AGAUCAAGAUCUUGCUAUACCCAGA

Primers for measuring miRNA levels by qPCR (note all qPCR reactions also use the "universal" primer in the miScript kit (Qiagen)):

eGFP primer:
(SEQ ID NO: 21)
5'-atgaacttcagggtcagcttgc

TetR primer:
(SEQ ID NO: 22)
5'-tcttgatcttccaatacgcaac

SOD1 primer:
(SEQ ID NO: 23)
5'-ttcagtcagtcctttaatgctt

Experimental Methods

Nucleic Acid Design

Pre-miR-451 structural mimics incorporating miR-155, miR-106, or miR-199 gene silencing guide strand sequence were used in certain of the studies described herein. These nucleic acids were made by the lab of Eric Lai, as published in Yang et al., PNAS, 2010, 107(34):15163-15168, which is herein incorporated by reference in its entirety.

Introduction/Expression of Pre-miR-451 Structural Mimics in Cells

Cells were transfected with plasmids using Lipofectamine 2000 according to the manufacturer's instructions. After four hours cells were washed in PBS and incubated with DMEM containing 10% FBS depleted of exosomes by ultracentrifugation according to Thery et al. (2006). After 24 h media was harvested and exosomes were purified by differential ultracentrifugation. RNA was purified from exosomes and exosome-producing cells using Trizol according to the manufacturer's instructions.

The plasmids used were generated as per Yang et al., PNAS, 2010, 107(34):15163-15168, which is herein incorporated by reference in its entirety.

Exosome Enrichment

Exosomes were enriched by differential centrifugation as previously described (Thery, 2006, Curr Protoc Cell Biol, Chapter 3, Unit 3 22). Briefly, MEF or MDA-MB-231 cells were cultured in media containing FBS depleted of exosomes by centrifugation at 100 000 g for 16 h (Thery, 2006, Curr Protoc Cell Biol, Chapter 3, Unit 3 22). To purify exosomes supernatant from cell cultures was centrifuged at 400 g (7 min), 2000 g (10 min) and 10 000 g (30 min, SW32 rotor). At each step the supernatant was recovered. After centrifugation at 100 000 g (1 h 10 min, SW32 rotor) the supernatant was removed and the pellet was resuspended. The pellet was washed in PBS by a final centrifugation at 100 000 g (20 min, TLA100.3 rotor). The exosome-enriched pellet was re-suspended in PBS for further analyses.

Dynamic Light Scattering

Preparations of enriched exosomes were analyzed by dynamic light scattering on a Protein Solutions Dynapro Instrument using Dynamics V6 software. Data were acquired every 10 seconds at 4° C. and 10% laser power for at least 200 seconds per sample. The intensity (Cnt/s) and size (nm) were generated automatically by the instrument.

Nanosight Particle Tracking Analysis

Preparations of enriched exosomes were analyzed using a Nanosight LM10 instrument with Nanoparticle Tracking Analysis software Version 2.3. Measurement temperature was 22° C. and time setting was 90 seconds. The analysis conditions were set as: Blur 3×3, Detection Threshold 3, Min Track Length 9, and Min Expected Size 30 nm. The analysis reports containing the particle size (nm) and concentration (particles/ml) were generated automatically.

Electron Microscopy

Exosome preparations were fixed in situ with 0.1 M cacodylate buffer containing 2% glutaraldehyde until processing for embedding, post-fixed in 1% osmium tetroxide (EMS, PA, USA) in cacodylate buffer at 4° C. After washing in buffer, exosomes were dehydrated in graded ethanol, infiltrated and embedded in Epon 812 (MECALAB, Quebec, Canada), as described (Luft, 1961, The Journal of Biophysical and Biochemical Cytology, 9:409).

Sections were stained with uranyl acetate and examination was performed with a Philips CM 100 electron microscope.

RT-qPCR

RT-qPCR was performed with the MiScript II Reverse Transcriptase system (Qiagen) and GoTaq® qPCR Master Mix (Promega A6002) using primers allowing amplification of the DNA produced in the reverse transcriptase step. Results were normalized to the ubiquitous miRNA let-7a and miR-16.

Primers used were as follows:

```
miR-451:
                                    (SEQ ID NO: 9)
AAACCGTTACCATTACTGAGTT;

miR-155:
                                    (SEQ ID NO: 10)
ACCCCTATCACGATTAGCATTAA;

miR-199:
                                    (SEQ ID NO: 11)
TAACCAATGTGCAGACTACTGT;

miR-106a:
                                    (SEQ ID NO: 12)
CTACCTGCACTGTAAGCACTTTT;

let-7a:
                                    (SEQ ID NO: 13)
TGAGGTAGTAGGTTGTATAGTT;
and miR-16:
                                    (SEQ ID NO: 24)
tagcagcacgtaaatattggcg.
```

Intracerebroventricular Injection

Ten μg of exosomes purified by differential centrifugation from NSC-34 cells expressing human SOD1 targeting silencing RNA from the pre-miR-451 backbone or control exosomes were injected into the intracerebroventicular space of mice transgenic for human SOD1 G93A (Jackson Labs) in a volume of 5 μL. Forty-eight hours later mice were sacrificed and brains were flash frozen and divided for either fluorescence in situ hybridization (FISH) or RT-qPCR quantification of SOD1 mRNA levels.

Fluorescence In Situ Hybridization

Tissues were collected from mice and placed in 4% PFA in PBS for 48 h. PFA was replaced by PBS with 30% sucrose until the tissues sink at the bottom. Tissues were placed in OCT and frozen with liquid nitrogen. Tissue sections of 6 μm were collected on slides and placed at −80° C. Slides were heated to room temperature (RT) before staining. Slides were placed in 4% PFA in PBS for 10 min at RT. They were washed with PBS (RT) and placed at 37° C. for 20 min in permeabilisation buffer (10 μg/mL proteinase K, 0.2% Triton X-100 in PBS). Slides were washed in PBS (RT) and blocked 1 h with 1% BSA, 100 μg/mL salmon sperm DNA and 250 μg/mL yeast extract RNA in PBS (RT). Slides were washed with PBS (RT) and treated for autofluorescence reduction with NaBH4 0.1% in water (RT) for 1 h. Slides were washed with Stellaris wash A buffer (LGC Biosearch Technologies, Petaluma, Calif., USA) (RT) and Stellaris fluorescent mRNA probes (SOD1, GAPDH, beta-actin) and IDT DIG-coupled siRNA probes (siSOD1, negative control siRNA, Integrated DNA Technologies, Coralville, Iowa, USA) were placed in hybridization buffer (90% Stellaris Hybridization buffer, 10% formamide). Slides were incubated with the probes in the dark at 37° C. over night. Slides were washed with wash A buffer (RT) and incubated with a sheep anti-DIG (Enzo Life Sciences, Farmingdale, N.Y., USA) 1:100 in blocking solution at RT for 1 h. Slides were washed with wash A buffer (RT) and incubated with a donkey anti-sheep AlexaFluor488 (Life Technologies, Waltham, Mass., USA) 1:500 in blocking solution at RT for 1 h. Slides were washed with wash A buffer (RT) and incubated with DAPI (Life Technologies) 1:10000 in PBS 5 min at RT. A final wash at RT was performed with Stellaris wash B buffer and slides were mounted with Citifluor AF3 antifadent solution (Electron Microscopy Sciences, Hatfield, Pa., USA) and sealed with nail polish.

Image Analysis.

ImageJ analysis software (NIH Image, http://rsbweb.nih.gov/nih-image/) was used for FISH image analysis. Briefly, images were acquired by epifluorescent microscopy (Zeiss AxioImager.M2, Carl Zeiss, Oberkochen. Germany) with a 63× Plan-Apochromat 1.4 Oil lense (1000× magnification). Colors were added after acquisition (blue for DAPI, green for siRNA SOD1, red for SOD1 mRNA, purple for GAPDH mRNA). Contrast and threshold were adjusted on the control images and kept the same for experimental images. Mean intensity and colocalisation of the whole image and regions of interest were measured with the software. Mean intensity average and SEM were analyzed using Excel software (Microsoft. Redmond, Wash., USA).

RT-qPCR

RT-qPCR was performed with (Promega A6002) or Quantitect qPCR master mix (Qiagen) using primers allowing amplification of the DNA produced in the reverse transcriptase step using the following primers mir-451: aaaccgttaccattactgagtt (SEQ ID NO: 14), let-7a: tgaggtagtaggttgtatagtt (SEQ ID NO: 15), mir-16: tagcagcacgtaaatattggcg (SEQ ID NO: 16).

Plasmid Constructs and Lentiviral Vectors

GFP siRNA, SOD1 siRNA or TetR siRNA integrated into the pre-miR-451 backbone were expressed from the lentiviral pGIPZ vector. Similar RNAs inserted into the pre-miR-16 backbone were used in some experiments. Cell lines, including NSC-34, stably expressing GFP siRNA or SOD1 siRNA from the pre-miR-451 backbone were generated by selecting with puromycin.

Synthetic RNAs

RNAs corresponding to 42 nt pre-miR-451 with an inserted GFP siRNA, or the same construct up to the Ago2 cleavage site, or the fully mature form of miR-451 produced GFP siRNA (single-stranded 22 nt RNA), or double-stranded GFP siRNA with 2 nt 3' overhangs were synthesized by IDT. These were transfected into mouse embryonic fibroblast cells either wild-type, with Ago2 genetically deleted, with wild-type Ago2 stably re-expressed or with catalytically dead mutant Ago2 stably re-expressed with RNAiMax (ThermoFisher). Two days later exosomes were purified and levels of mature GFP siRNA in exosomes was quantified by RT-qPCR.

Ago2 Processed Mimic Sequence:

(SEQ ID NO: 25)
augaacuucagggucagcuugcgcugaccc

Drosha Processed Mimic Sequence:

(SEQ ID NO: 26)
AUGAACUUCAGGGUCAGCUUGCGCUGACCCUGAAGUUCAUUC

Fully Mature Mimic Sequence:

(SEQ ID NO: 27)
AUGAACUUCAGGGUCAGCUUGC

Complementary Strand Sequence to render fully mature mimic double stranded:

(SEQ ID NO: 28)
AAGCUGACCCUGAAGUUCAUUC

Exosome-Mediated Delivery of mIR-451 Derived siRNA in Cell Culture Models

Exosomes from several cell types (MSC. MEF, HeLa, N2A, C8-D1A, BV2 and RAW267) were purified by differential centrifugation. One µg of exosomes was added to each well of a 6 well plate containing HeLa, NSC-34 or N2A cells stably expressing GFP. After 48 hours cells were collected and GFP was quantified by flow cytometry. Cells were gated on FSC and SSC and the Geometric mean of GFP expression was obtained using Kaluza software. Geometric mean of GFP levels in cells treated with wild-type exosomes derived from the same cells was set to 100%.

One or more illustrative embodiments and examples have been described by way of non-limiting example. It will be understood to persons skilled in the art that a number of variations and modifications may be made without departing from the scope of the invention as defined in the claims.

REFERENCES

1. Kanasty, Dorkin, Vegas, Anderson. Nature materials 12, 967 (2013).
2. Whitehead. Langer, Anderson, Nat Rev Drug Discov 8, 129 (2009).
3. Coelho et al., N Engl J Med 369, 819 (2013).
4. Haussecker, Molecular therapy. Nucleic acids 1, e8 (2012).
5. Fabian, Sonenberg, Nat Struct Mol Biol 19, 586 (2012).
6. Kasinski, Slack, Nature reviews. Cancer 11, 849 (2011).
7. Emdc, Hornstcin, EMBO J 33, 1428 (2014).
8. Dahlman et al., Nature nanotechnology 9, 648 (2014).
9. Kanasty, Whitehead, Vegas, Anderson, Mol Ther 20, 513 (2012).
10. Kleinman et al., Nature 452, 591 (2008).
11. Raposo, Stoorvogel, J Cell Biol 200, 373 (2013).
12. Valadi et al., Nat Cell Biol 9, 654 (2007).
13. Zhuang et al., Mol Ther 19, 1769 (2011).
14. Alvarez-Erviti et al., Nat Biotechnol 29, 341 (2011).
15. S, Mager, Breakefield, Wood, Nat Rev Drug Discov 12, 347 (2013).
16. Fang et al., PLoS Biol 5, c158 (2007).
17. Zeelenberg et al., Cancer Res 68, 1228 (2008).
18. Ohno et al., Mol Ther 21, 185 (2013).
19. Lamparski et al., J Immunol Methods 270, 211 (2002).
20. Viaud et al., J Immunother 34, 65 (2011).
21. Cheng, Sharpies, Scicluna, Hill, Journal of extracellular vesicles 3, (2014).
22. Collino et al., PLoS One 5, e11803 (2010).
23. Gibbings, Ciaudo, Erhardt, Voinnet, Nat Cell Biol 11, 1143 (2009).
24. Batagov, Kuznetsov, Kurochkin, BMC Genomics 12 Suppl 3, S18 (2011).
25. Villarroya-Beltri et al., Nat Commun 4, 2980 (2013).
26. Kooijmans et al., J Control Release 172, 229 (2013).
27. Cheloufi, Dos Santos, Chong, Hannon, Nature 465, 584 (2010).
28. Yang, Maurin, Lai, RNA 18, 945 (2012).
29. Thery, Amigorena, Raposo, Clayton, Curr Protoc Cell Biol Chapter 3, Unit 3 22 (2006).
30. Stevenson et al., Molecular therapy. Nucleic acids 2, e133 (2013).
31. Gantier et al., Nucleic Acids Res 39, 5692 (2011).
32. Bartlett, Davis, Biotechnology and bioengineering 97, 909 (2007).
33. Fabian, M. R., Sonenberg, N. & Filipowicz, W. Regulation of mRNA translation and stability by microRNAs. Annu Rev Biochem 79, 351-379, (2010).
34. Pencheva, N. & Tavazoie, S. F. Control of metastatic progression by microRNA regulatory networks. Nat Cell Biol 15, 546-554, (2013).
35. Croce, C. M. Causes and consequences of microRNA dysregulation in cancer. Nat Rev Genet 10, 704-714, (2009).
36. Abe, M. & Bonini, N. M. MicroRNAs and neurodegeneration: role and impact. Trends Cell Biol 23, 30-36. (2013).
37. Coelho, T. et al. Safety and efficacy of RNAi therapy for transthyretin amyloidosis. N Engl J Med 369, 819-829, (2013).
38. Kanasty, R., Dorkin, J. R., Vegas, A. & Anderson, D. Delivery materials for siRNA therapeutics. Nature materials 12, 967-977, (2013).
39. Whitehead, K. A., Langer, R. & Anderson, D. G. Knocking down barriers: advances in siRNA delivery. Nat Rev Drug Discov 8, 129-138, (2009).
40. Zimmermann, T. S. et al. RNAi-mediated gene silencing in non-human primates. Nature 441, 111-114, (2006).
41. Haussecker, D. The Business of RNAi Therapeutics in 2012. Molecular therapy. Nucleic acids 1, e8, (2012).
42. Raposo, G. & Stoorvogel, W. Extracellular vesicles: exosomes, microvesicles, and friends. J Cell Biol 200, 373-383, (2013).
43. Valadi, H. et al. Exosome-mediated transfer of mRNAs and microRNAs is a novel mechanism of genetic exchange between cells. Nat Cell Biol 9, 654-659, (2007).
44. Zhuang, X. et al. Treatment of brain inflammatory diseases by delivering exosome encapsulated anti-inflammatory drugs from the nasal region to the brain. Mol Ther 19, 1769-1779. (2011).
45. Alvarez-Erviti, L. et al. Delivery of siRNA to the mouse brain by systemic injection of targeted exosomes. Nat Biotechnol 29, 341-345, (2011).

46. Colombo, M., Raposo. G. & Thery, C. Biogenesis, secretion, and intercellular interactions of exosomes and other extracellular vesicles. Annu Rev Cell Dev Biol 30, 255-289, (2014).
47. Batagov. A. O., Kuznetsov. V. A. & Kurochkin, I. V. Identification of nucleotide patterns enriched in secreted RNAs as putative cis-acting elements targeting them to exosome nano-vesicles. BMC Genomics 12 Suppl 3, S18, (2011).
48. Villarroya-Beltri, C. et al. Sumoylated hnRNPA2B1 controls the sorting of miRNAs into exosomes through binding to specific motifs. Nat Commun 4, 2980, (2013).
49. Kooijmans, S. A. et al. Electroporation-induced siRNA precipitation obscures the efficiency of siRNA loading into extracellular vesicles. J Control Release 172, 229-238, (2013).
50. Cheng, L., Sharples, R. A., Scicluna, B. J. & Hill, A. F. Exosomes provide a protective and enriched source of miRNA for biomarker profiling compared to intracellular and cell-free blood.
Journal of extracellular vesicles 3, (2014).
51. Collino, F. et al. Microvesicles derived from adult human bone marrow and tissue specific mesenchymal stem cells shuttle selected pattern of miRNAs. PLoS One 5, e11803, (2010).
52. Bach, F. H. & Sachs, D. H. Current concepts: immunology. Transplantation immunology. N Engl J Med 317, 489-492, (1987).
53. Lai, R. C. et al. Exosome secreted by MSC reduces myocardial ischemia/reperfusion injury.
Stem Cell Res 4, 214-222, (2010).
54. Takahashi, Y. et al. Visualization and in vivo tracking of the exosomes of murine melanoma B16-BL6 cells in mice after intravenous injection. J Biotechnol 165, 77-84, (2013).
55. Wiklander, O. P. et al. Extracellular vesicle in vivo biodistribution is determined by cell source, route of administration and targeting. Journal of extracellular vesicles 4, 26316, (2015).
56. Komarova, Y. & Malik, A. B. Regulation of endothelial permeability via paracellular and transcellular transport pathways. Annual review of physiology 72, 463-493, (2010).
57. Thery, C., Amigorena, S., Raposo, G. & Clayton, A. Isolation and characterization of exosomes from cell culture supernatants and biological fluids. Curr Protoc Cell Biol Chapter 3, Unit 3 22, (2006).
58. Luft, J. H. Improvements in epoxy resin embedding methods. The Journal of biophysical and biochemical cytology 9, 409-414, (1961).

All references cited in this section and elsewhere in the specification are hereby incorporated by reference in their entirety.

---

What is claimed is:

1. A method for producing exosomes or exosome-like vesicles comprising a gene silencing nucleic acid, a nucleic acid of interest, or a precursor thereof, said method comprising:
   introducing into an exosome-producing cell, or expressing in an exosome-producing cell, a nucleic acid construct comprising the gene silencing nucleic acid, nucleic acid of interest, or a precursor thereof, incorporated within a pre-miR-451 structural mimic;
   treating the exosome-producing cell with a lysosomal or autophagy inhibitor;
   producing exosomes or exosome-like vesicles from the cell; and
   collecting or enriching the produced exosomes or exosome-like vesicles.

2. The method according to claim 1, wherein the pre-miR-451 structural mimic comprises a stem-loop secondary structure having a blunt end, a 5' overhang, a 3' overhang, or 5' and 3' loose ends, and having an overall length of about 25-54 nucleotides (nt).

3. The method according to claim 1, wherein the pre-miR-451 structural mimic comprises a stem-loop secondary structure having an overall loop length of about 4-8 nt.

4. The method according to claim 1, wherein the pre-miR-451 structural mimic comprises a stem-loop secondary structure having at least one base pair mismatch in the stem.

5. The method according to claim 1, wherein the pre-miR-451 structural mimic comprises a stem-loop secondary structure with a 3' end which extends to, or before, or after an Ago2 cleavage position, such that the pre-miR-451 structural mimic includes a 5' overhang portion and a 3' base-paired portion.

6. The method according to claim 1, wherein the pre-miR-451 structural mimic comprises a single-stranded structure including a 3' portion, mimicking mature miR-451.

7. The method according to claim 6, wherein the pre-miR-451 structural mimic is about 22-35 nt in length.

8. The method according to claim 1, wherein the cell is an embryonic stem cell (ESC) clone H1 or H9 cell, a mesenchymal stem cell (MSC), a cell having low Ago2 expression or activity levels, a primary human mesenchymal stem cell, a primary mouse macrophage, a human breast cancer cell line, a mouse or human neuronal cell line, a mouse astrocyte cell line, a mouse microglia cell line, a mouse motor neuron cell line, a HeLa cell, a mouse embryonic fibroblast, or a mouse dendritic cell.

9. The method according to claim 1, wherein the gene silencing nucleic acid is, or is derived from, a miRNA, shRNA, Crispr guide RNA, or siRNA.

10. The method according to claim 1, wherein the cell is cultured in serum-free media, or in exosome-depleted serum media, while producing the exosomes or exosome-like vesicles.

11. The method according to claim 2, wherein the pre-miR-451 structural mimic further comprises an overall length of 40, 41, 42, 43, 44, 45, 46, 47, 48, 49, 50, 51, or 52 nt.

12. A method for producing exosomes or exosome-like vesicles comprising a gene silencing nucleic acid, a nucleic acid of interest, or a precursor thereof, said method comprising:
   introducing into an exosome-producing cell, or expressing in an exosome-producing cell, a nucleic acid construct comprising the gene silencing nucleic acid, nucleic acid of interest, or a precursor thereof, incorporated within a pre-miR-451 structural mimic;
   producing exosomes or exosome-like vesicles from the cell; and
   collecting or enriching the produced exosomes or exosome-like vesicles,
   wherein the pre-miR-451 structural mimic comprises a stem-loop secondary structure having at least one base pair mismatch in the stem, and wherein at least one base pair mismatch in the stem is positioned within the first three base pairs adjacent to a Drosha cleavage site.

13. A method for producing exosomes or exosome-like vesicles comprising a gene silencing nucleic acid, a nucleic acid of interest, or a precursor thereof, said method comprising:
   introducing into an exosome-producing cell, or expressing in an exosome-producing cell, a nucleic acid construct comprising the gene silencing nucleic acid, nucleic acid of interest, or a precursor thereof, incorporated within a pre-miR-451 structural mimic;
   producing exosomes or exosome-like vesicles from the cell; and
   collecting or enriching the produced exosomes or exosome-like vesicles,
   wherein the pre-miR-451 structural mimic comprises a single-stranded structure including a 3' portion, which is a loop-derived sequence, mimicking mature miR-451.

14. A method for producing exosomes or exosome-like vesicles comprising a gene silencing nucleic acid, a nucleic acid of interest, or a precursor thereof, said method comprising:
   introducing into an exosome-producing cell, or expressing in an exosome-producing cell, a nucleic acid construct comprising the gene silencing nucleic acid, nucleic acid of interest, or a precursor thereof, incorporated within a pre-miR-451 structural mimic;
   producing exosomes or exosome-like vesicles from the cell; and
   collecting or enriching the produced exosomes or exosome-like vesicles,
   wherein the pre-miR-451 structural mimic comprises a single-stranded structure including a 3' portion, mimicking mature miR-451, and wherein the pre-miR-451 structural mimic is about 23-24 nt in length.

15. The method according to claim 8, wherein the cell is a human breast cancer cell line MDA-MB-231, a mouse or human neuronal cell line Neuro2a or SHSY, a mouse astrocyte cell line C8 Da or SIM, a mouse microglia cell line BV2, a mouse motor neuron cell line NSC-34 or MN-1, a HeLa cell, a mouse embryonic fibroblast, or a mouse dendritic cell line JAWS II.

* * * * *